United States Patent
Shin

(10) Patent No.: US 11,875,881 B2
(45) Date of Patent: *Jan. 16, 2024

(54) METHOD OF MANAGING EXTERNAL DEVICES, METHOD OF OPERATING EXTERNAL DEVICE, HOST DEVICE, MANAGEMENT SERVER, AND EXTERNAL DEVICE

(71) Applicant: SAMSUNG ELECTRONICS CO., LTD., Suwon-si (KR)

(72) Inventor: Hang-sik Shin, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 58 days.

This patent is subject to a terminal disclaimer.

(21) Appl. No.: 17/342,860

(22) Filed: Jun. 9, 2021

(65) Prior Publication Data
US 2021/0295993 A1 Sep. 23, 2021

Related U.S. Application Data

(63) Continuation of application No. 16/654,266, filed on Oct. 16, 2019, now Pat. No. 11,056,234, which is a
(Continued)

(30) Foreign Application Priority Data

Dec. 17, 2012 (KR) ........................ 10-2012-0147725
May 9, 2013 (KR) ........................ 10-2013-0052754

(51) Int. Cl.
*G16H 40/67* (2018.01)
*G16H 40/40* (2018.01)
(Continued)

(52) U.S. Cl.
CPC ............... *G16H 40/67* (2018.01); *G06F 8/65* (2013.01); *G16H 40/40* (2018.01); *H04L 41/24* (2013.01);
(Continued)

(58) Field of Classification Search
CPC ........ G16H 40/67; G16H 40/40; G16H 50/20; H04L 67/06; H04L 41/24; G06F 8/65;
(Continued)

(56) References Cited

U.S. PATENT DOCUMENTS 6,645,142 B2    11/2003  Braig
6,924,727 B2    8/2005   Nagaoka et al.
(Continued)

FOREIGN PATENT DOCUMENTS

CN    1393092 A    1/2003
CN    1255972 C    5/2006
(Continued)

OTHER PUBLICATIONS

"Medical Devices/Equipment Management Policy"—Health Service Executive, Mar. 11, 2010 https://www.hse.ie/eng/services/publications/corporate/medicaldevicesequipment.pdf (Year: 2010).*
(Continued)

*Primary Examiner* — Randy A Scott
(74) *Attorney, Agent, or Firm* — Sughrue Mion, PLLC

(57) ABSTRACT

Provided is a method of a host device managing at least one external device connected to the host device through a management server. The method includes: obtaining measurement information measured by the at least one external device; requesting authorization by the management server; transmitting the obtained measurement information to the management server when the authentication succeeds; receiving management information for managing the at least one external device, where the management information is
(Continued)

generated based on the measurement information by the management server; and managing the at least one external device based on the received management information.

21 Claims, 49 Drawing Sheets

Related U.S. Application Data continuation of application No. 14/556,768, filed on Dec. 1, 2014, now Pat. No. 10,459,712, which is a continuation of application No. 14/109,293, filed on Dec. 17, 2013, now Pat. No. 9,740,470.

(51) Int. Cl.

| | | |
|---|---|---|
| G06F 8/65 | (2018.01) | |
| H04L 29/08 | (2006.01) | |
| H04L 12/24 | (2006.01) | |
| H04L 41/00 | (2022.01) | |
| H04L 67/06 | (2022.01) | |
| G16H 20/40 | (2018.01) | |
| G16H 20/30 | (2018.01) | |
| G16H 10/60 | (2018.01) | |
| G16H 50/20 | (2018.01) | |
| G16H 20/00 | (2018.01) | |
| G16H 20/10 | (2018.01) | |
| G16H 20/60 | (2018.01) | |

(52) U.S. Cl.
CPC ............. *H04L 67/06* (2013.01); *G16H 10/60* (2018.01); *G16H 20/00* (2018.01); *G16H 20/10* (2018.01); *G16H 20/30* (2018.01); *G16H 20/40* (2018.01); *G16H 20/60* (2018.01); *G16H 50/20* (2018.01)

(58) Field of Classification Search
CPC ..... G06F 3/04883; H04Q 9/00; A61B 5/0205; A61B 5/681; A61B 5/7435
See application file for complete search history.

(56) References Cited

U.S. PATENT DOCUMENTS

| | | | |
|---|---|---|---|
| 7,643,895 B2 | 1/2010 | Gupta et al. | |
| 7,791,467 B2 | 9/2010 | Mazar et al. | |
| 7,822,635 B1 | 10/2010 | Brown et al. | |
| 8,002,700 B2 | 8/2011 | Ferek-Petric et al. | |
| 8,253,586 B1 | 8/2012 | Matak | |
| 8,475,367 B1* | 7/2013 | Yuen .................... | G16H 50/30 |
| | | | 177/4 |
| 8,726,266 B2 | 5/2014 | Kiaie et al. | |
| 8,909,731 B2 | 12/2014 | Takeuchi | |
| 9,317,660 B2 | 4/2016 | Burich | |
| 9,656,092 B2 | 5/2017 | Golden | |
| 2001/0031998 A1 | 10/2001 | Nelson et al. | |
| 2002/0033753 A1 | 3/2002 | Imbo | |
| 2002/0055892 A1 | 5/2002 | Brown et al. | |
| 2002/0180579 A1 | 12/2002 | Nagaoka et al. | |
| 2003/0095648 A1* | 5/2003 | Kaib .................... | A61B 5/0006 |
| | | | 379/106.02 |
| 2004/0117204 A1 | 6/2004 | Mazar et al. | |
| 2005/0027807 A1* | 2/2005 | Fengler ................. | G06F 8/60 |
| | | | 719/321 |
| 2005/0249486 A1 | 11/2005 | Murray | |
| 2006/0036555 A1 | 2/2006 | Beck et al. | |
| 2008/0270188 A1 | 10/2008 | Garg et al. | |
| 2009/0063187 A1 | 3/2009 | Johnson et al. | |
| 2009/0171170 A1 | 7/2009 | Li et al. | |
| 2010/0292556 A1 | 11/2010 | Golden | |
| 2010/0292600 A1 | 11/2010 | DiBenedetto | |
| 2010/0331145 A1 | 12/2010 | Lakovic et al. | |
| 2011/0006876 A1 | 1/2011 | Moberg et al. | |
| 2011/0087137 A1 | 4/2011 | Hanoun | |
| 2011/0161111 A1 | 6/2011 | Dicks et al. | |
| 2011/0234409 A1 | 9/2011 | Soliman | |
| 2011/0289497 A1 | 11/2011 | Kiaie et al. | |
| 2012/0062571 A1 | 3/2012 | Malek | |
| 2012/0065993 A1 | 3/2012 | Arimitsu | |
| 2012/0139720 A1 | 6/2012 | Mazar et al. | |
| 2012/0159142 A1 | 6/2012 | Jibbe | |
| 2012/0166538 A1 | 6/2012 | Son et al. | |
| 2012/0182939 A1 | 7/2012 | Rajan | |
| 2013/0002435 A1 | 1/2013 | Utter et al. | |
| 2013/0090565 A1 | 4/2013 | Quy | |
| 2013/0231711 A1* | 9/2013 | Kaib ..................... | G16H 40/63 |
| | | | 607/5 |
| 2014/0125493 A1 | 5/2014 | Utter | |

FOREIGN PATENT DOCUMENTS

| | | |
|---|---|---|
| CN | 102438512 A | 5/2012 |
| EP | 1 862 112 A1 | 12/2007 |
| EP | 2 433 554 A1 | 3/2012 |
| JP | 10-3452 A | 1/1998 |
| JP | 2000-316820 A | 11/2000 |
| JP | 2008-149146 A | 7/2008 |
| JP | 2011-060232 A | 3/2011 |
| JP | 2012-221386 A | 11/2012 |
| JP | 2012-230521 A | 11/2012 |
| KR | 10-2012-0072022 A | 7/2012 |
| KR | 10-2012-0082041 A | 7/2012 |
| RU | 116662 U1 | 5/2012 |

OTHER PUBLICATIONS

"Updating Peripheral Device Firmware via a Portable Device"—Ruster et al, SCISPACE, Feb. 27, 2012 https://typeset.io/papers/updating-peripheral-device-firmware-via-a-portable-device-2i66mqlm2g (Year: 2012).*

Communication dated Dec. 9, 2022, issued by China National Intellectual Property Administration in Chinese Application No. 201910011233.4.

Communication dated Jan. 16, 2023, issued by the European Patent Office in European Application No. 19208989.4.

Communication dated Nov. 18, 2016 issued by the Australian Patent Office in counterpart Australian Patent Application No. 2013364704.

Communication issued by the Japanese Patent Office dated Dec. 11, 2017 in counterpart Japanese Patent Application No. 2013-258972.

L1: Letter of reply of the applicant to ESOP (Ref: P213583EP / JPH), dated Mar. 1, 2018, 3 pages total.

International Search Report dated Mar. 21, 2014 issued in International Application No. PCT/KR2013/011565 (PCT/ISA/210/220).

Communication dated Jun. 28, 2017, from the State Intellectual Property Office of People's Republic of China in counterpart Application No. 201310693765.3.

Office Action dated Jul. 13, 2018 by the Japanese Patent Office in counterpart Japanese Patent Application No. 2013-258972.

Written Opinion dated Mar. 21, 2014 issued in International Application No. PCT/KR/2013/011565 (PCT/ISA/237).

Communication issued by the State Intellectual Property Office of P.R. China dated Jan. 17, 2018 in counterpart Chinese Patent Application No. 201310693765.3.

Communication dated Nov. 6, 2018, issued by the European Patent Office in counterpart European Application No. 13197690.4.

Communication dated Sep. 7, 2017, from the Russian Patent Office in counterpart application No. 2015129073/08.

Communication dated Mar. 20, 2017, issued by the Australian Patent Office in counterpart Australian Patent Application No. 2013364704.

Communication dated Sep. 5, 2017, from the European Patent Office in counterpart European Application No. 13197690.4.

"Medical Devices/Equipment Management Policy (Incorporating the Medical Devices Management Standard)"—Heath Service Executive, Mar. 2009 http://www.hse.ie.eng/services/publications/corporate/Medicaldevicesequipment.pdf.

(56) References Cited

OTHER PUBLICATIONS

"Wearable Sensor-Based Rehabilitation Exercise Assessment for Knee Osteoarthritis"—Chen et al, Department of Biomedical Engineering, National Yang-Ming University, Feb. 12, 2015 https://pdfs.semanticscholar.org/8897/45315e1f4a194c48a953d9c72b4835728c28.pdf (Year: 2015).

"Proposed Amendment"—II Nam Koh Jun. 18, 2019 (Year: 2019).

Communication dated Feb. 17, 2020 issued by the European Intellectual Property Office in counterpart European Application No. 19208989.4.

Communication dated Aug. 12, 2023, issued by China National Intellectual Property Administration in Chinese Patent Application No. 201910011233.4.

Communication dated Nov. 13, 2023 issued by China National Intellectual Property Administration in Chinese Application No. 20190011233.4.

\* cited by examiner

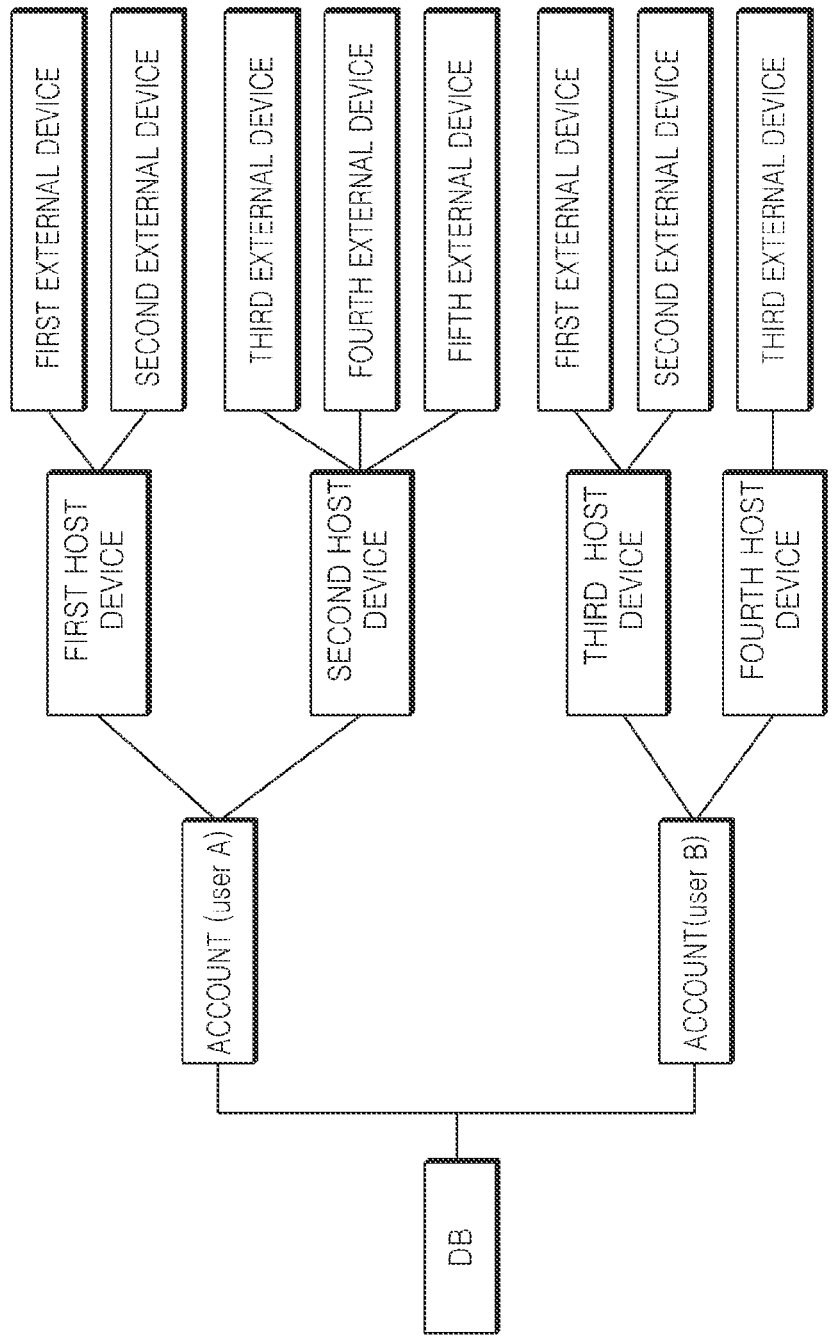

FIG. 9C

| ACCOUNT | ACCOUNT A (father) | | ACCOUNT B (mother) | | |
|---|---|---|---|---|---|
| HOST | DEVICE a | DEVICE a' | DEVICE b | DEVICE b' | DEVICE b" |
| EXTERNAL DEVICE | SCALE ▲<br>BLOOD SUGAR METER ▲<br>BLOOD PRESSURE GAUGE ▲<br>MEDICINE CONTAINER ▲<br>RUNNING MACHINE<br>DUMB-BELL<br>. . . | HUMIDIFIER ▲<br>THERMOMETER ▲<br>AIR CLEANER ▲<br>FAN HEATER ▲<br>REFRIGERATOR<br>. . . | SCALE ▲<br>BLOOD SUGAR METER<br>BLOOD PRESSURE GAUGE<br>MEDICINE CONTAINER ▲<br>RUNNING MACHINE ▲<br>HULA HOOP<br>BICYCLE<br>. . . | HUMIDIFIER<br>AIR CLEANER<br>FAN HEATER<br>REFRIGERATOR ▲<br>VACUUM CLEANER<br>. . . | TABLET ▲<br>MP3 PLAYER<br>AUDIO<br>DTV<br>. . . |

910

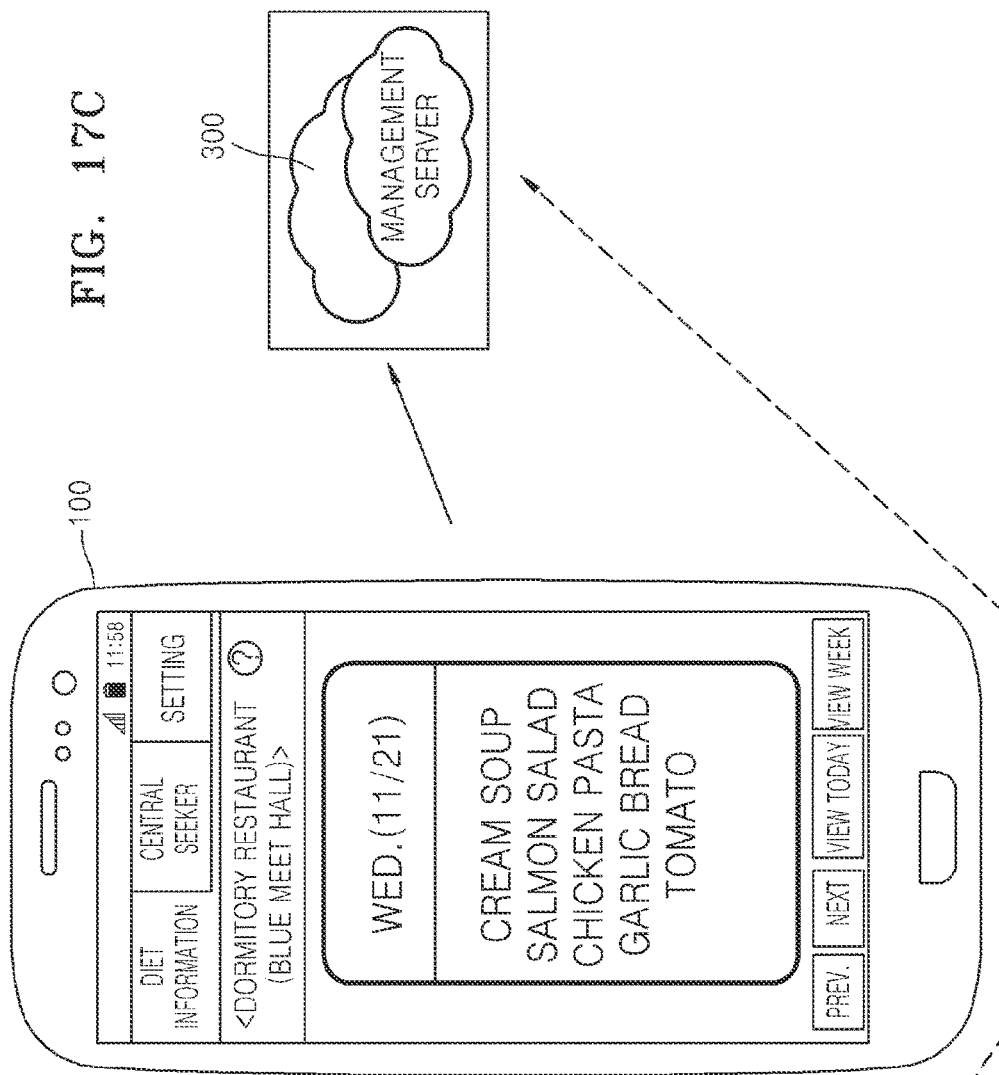
FIG. 17A
FIG. 17B
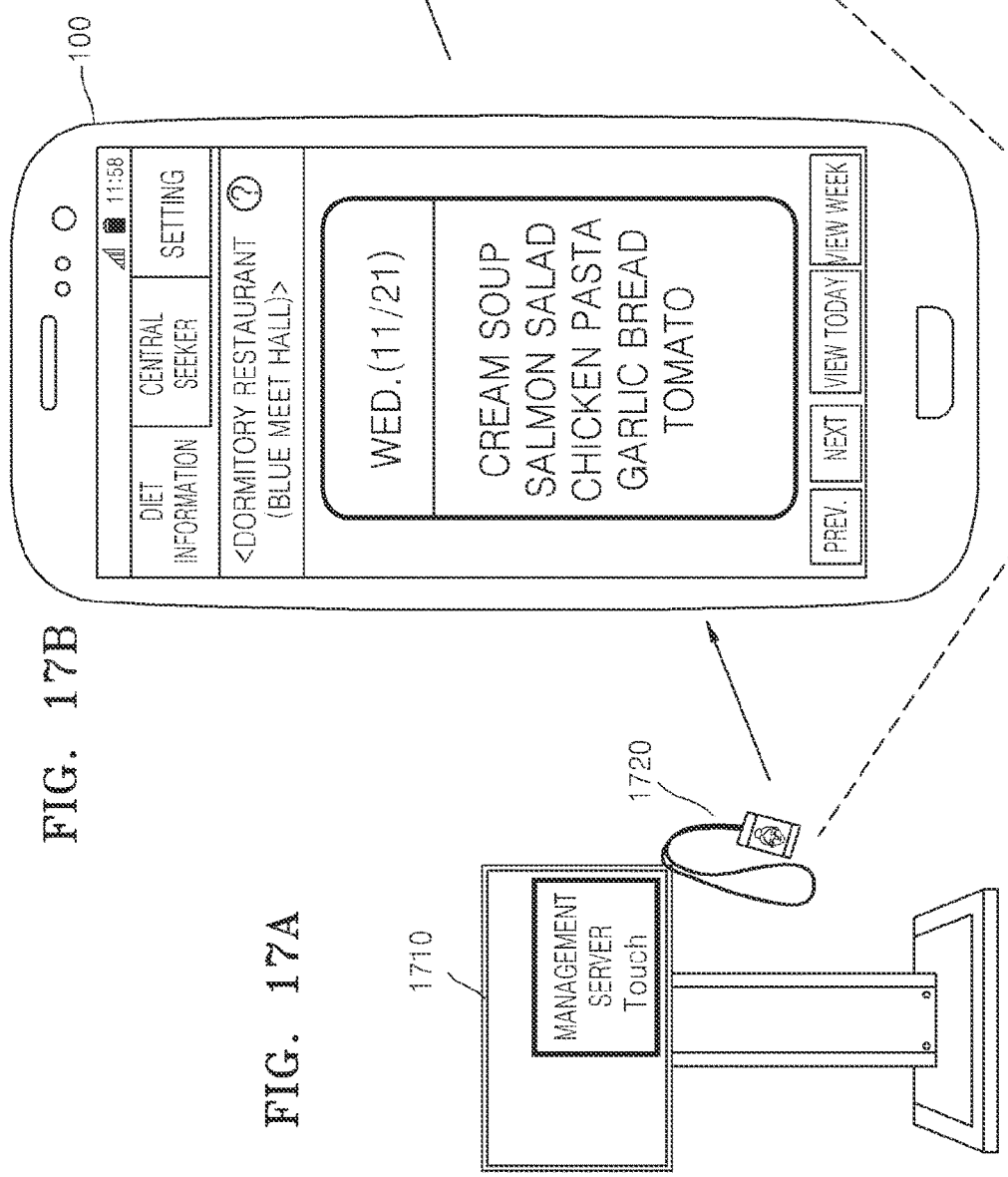
FIG. 17C

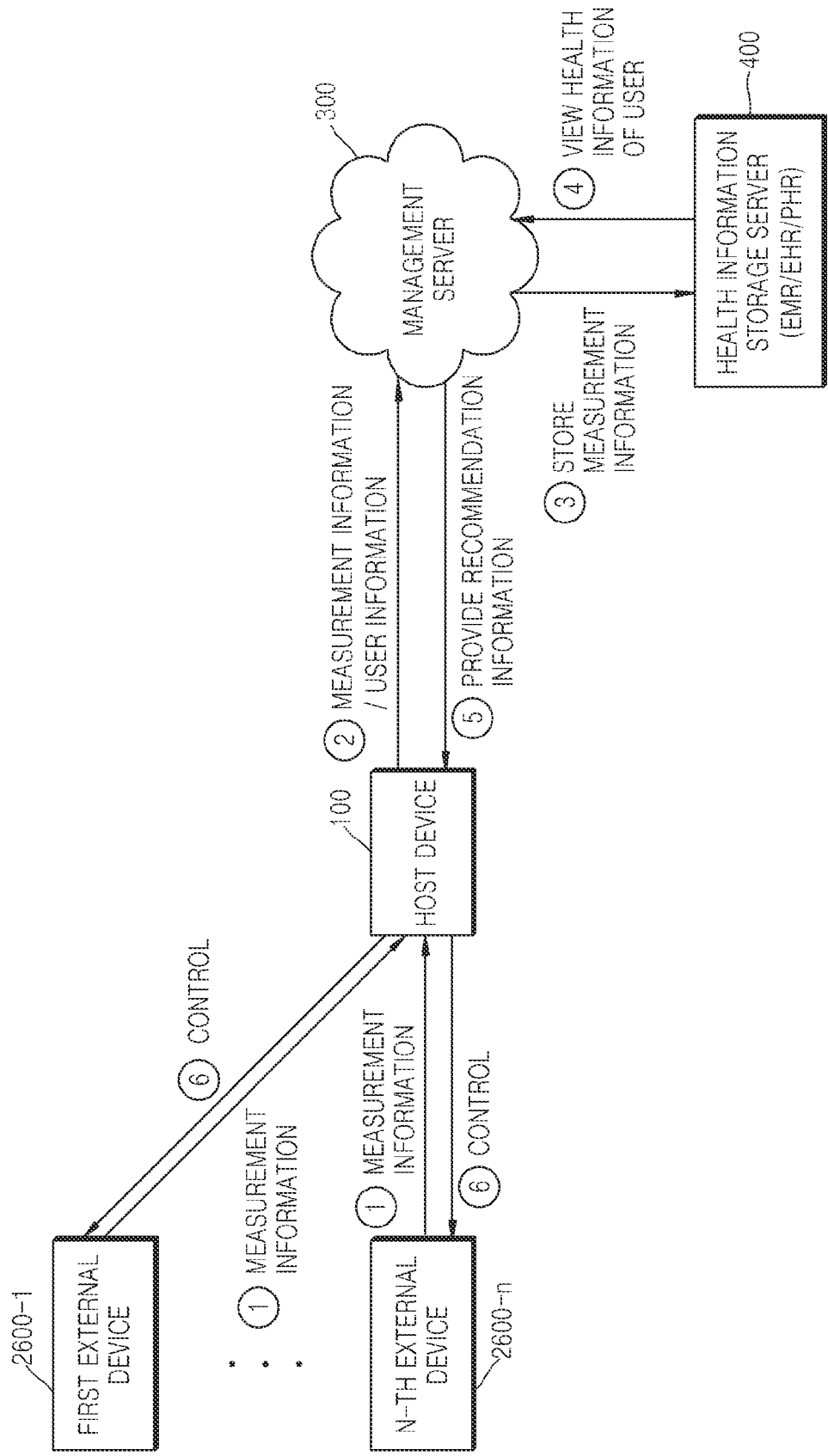

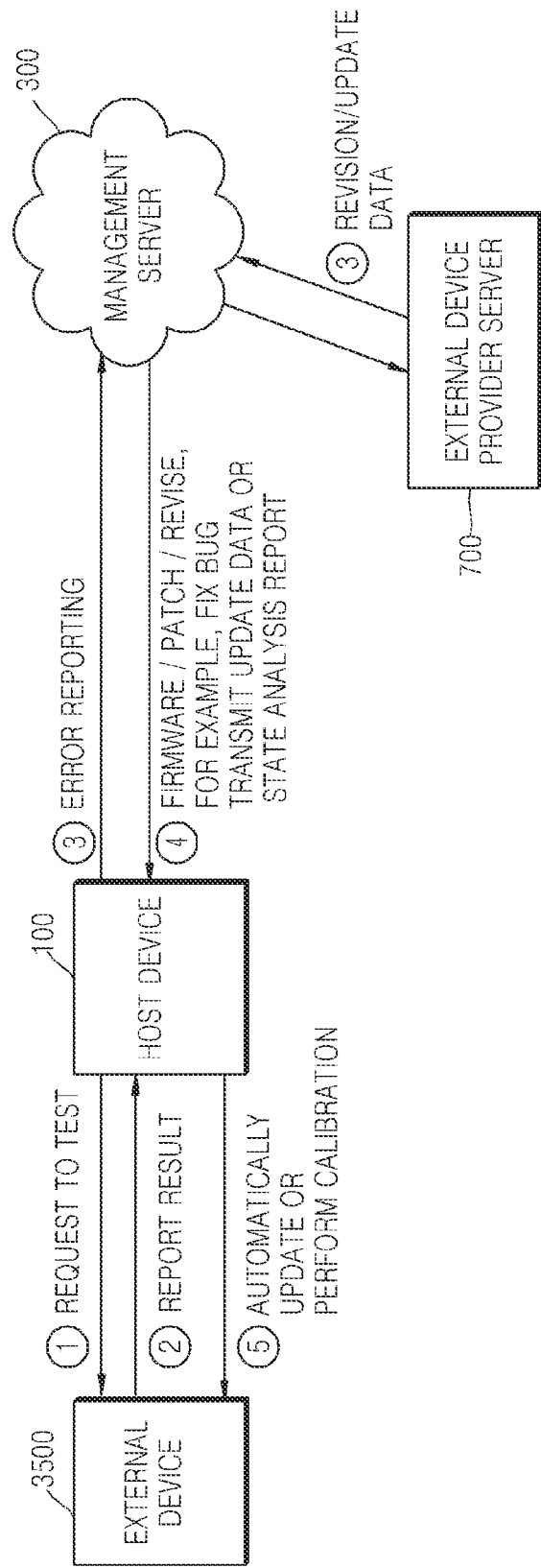

METHOD OF MANAGING EXTERNAL DEVICES, METHOD OF OPERATING EXTERNAL DEVICE, HOST DEVICE, MANAGEMENT SERVER, AND EXTERNAL DEVICE

CROSS REFERENCE TO RELATED APPLICATIONS

This application is a Continuation Application of U.S. patent application Ser. No. 16/654,266, filed on Oct. 16, 2019, which is a Continuation Application of U.S. patent application Ser. No. 14/556,768, filed on Dec. 1, 2014, which was issued as U.S. Pat. No. 10,459,712 on Oct. 29, 2019, which is a continuation of U.S. patent application Ser. No. 14/109,293, filed Dec. 17, 2013, which was issued as U.S. Pat. No. 9,740,470 on Aug. 22, 2017, which claims priority from of Korean Patent Application No. 10-2012-0147725, filed on Dec. 17, 2012, and Korean Patent Application No. 10-2013-0052754, filed on May 9, 2013, in the Korean Intellectual Property Office, the disclosures of which are incorporated herein in their entirety by reference.

BACKGROUND

1. Field

One or more exemplary embodiments relate to a method of managing an external device, which is performed by a host device for managing at least one external device connected to the host device through a management server, a method of managing an external device, which is performed by a management server, a method of operating an external device, a host device, a management server, and an external device.

2. Description of the Related Art

With the gradual development of communication technologies, a device may execute an application in connection with various peripheral devices, and may control the various peripheral devices through the application.

Also, with the increase in the development of peripheral devices which can be connected to a device through an application, a peripheral device managing system for integrally managing peripheral devices, providing bi-directional interaction between a device and a peripheral device, and remotely interacting with a peripheral device is desired.

SUMMARY

One or more exemplary embodiments may include a method of managing an external device, wherein at least one device connected to a host device is effectively managed through a management server, and a system for managing an external device.

Additional aspects will be set forth in part in the description which follows and, in part, will be apparent from the description, or may be learned by practice of the presented embodiments.

According to an aspect of an exemplary embodiment, a method of a host device managing at least one external device connected to the host device through a management server, includes: obtaining measurement information measured by the at least one external device; requesting authentication by the management server; transmitting the obtained measurement information to the management server when the authentication succeeds; receiving management information for managing the at least one external device, which is generated by the management server based on the measurement information; and managing the at least one external device based on the received management information.

The requesting authentication may include transmitting at least one of account information of the host device and identification information of the host device to the management server.

The obtaining of the measurement information may include obtaining health-related measurement information of a user.

The health-related measurement information may include at least one of physical information, administration information, environment information, meal information, and exercise information.

The obtaining of the measurement information may include obtaining information of a state of consumables used in the at least one external device.

The transmitting of the measurement information may include: extracting a part of the measurement information according to a predetermined standard; and transmitting the extracted part of the measurement information.

The extracting of the part may include extracting the part of the obtained measurement information based on whether the at least one external device that transmitted the measurement information is a medical device.

The extracting of the part may include extracting the part of the obtained measurement information based on a type of the obtained measurement information.

The extracting of the part may include: pre-selecting, based on a user input, a type of the measurement information to be transmitted to the management server; and comparing the type of the obtained measurement information and the pre-selected type of the measurement information.

The receiving of the management information may include receiving at least one of diagnosis information, prescription information, food recommendation information, exercise recommendation information, environment configuration information, alarm information, and update information for updating the at least one external device, which are generated based on the measurement information.

The managing of the at least one external device may include: generating a control command corresponding to the at least one external device, based on the management information; and transmitting the generated control command to the at least one external device.

The generating of the control command may include: changing the generated control command according to a control protocol of the at least one external device; and transmitting the changed control command.

The managing of the at least one external device may include controlling the at least one external device to output at least one of an alarm, a warning, and recommendation information.

The managing of the at least one external device may include changing a setting value of the at least one external device.

The managing of the at least one external device may include updating a program installed in the at least one external device.

The managing of the at least one external device may include displaying management information for managing the at least one external device on a screen of the host device.

The method may further include transmitting registration request information with respect to the at least one external device to the management server, wherein the registration request information includes at least one of identification information of the at least one external device, application information related to the at least one external device, connection information for a connection with the at least one external device, identification information of the host device, and account information.

According to an aspect of another exemplary embodiment, a method of a management server managing an external device, includes: a management server receiving an authentication request from a host device to which at least one external device is connected; authenticating the host device in response to the authentication request; receiving measurement information measured by the at least one external device from the authenticated host device; and managing the at least one external device based on the received measurement information.

The authenticating of the host device may include: receiving, from the host device, at least one of account information of the host device and identification information of the host device; and authenticating the host device based on at least one of the account information of the host device and the identification information of the host device.

The method may further include receiving, from the host device, registration request information with respect to the at least one external device; and registering the at least one external device based on the registration request information.

The registration request information may include at least one of identification information of the at least one external device, application information related to the at least one external device, connection information for a connection with the at least one external device, identification information of the host device, and account information.

The registering of the at least one external device may include mapping and storing in a memory at least one of account information of the host device and identification information of the host device, and identification information of the at least one external device.

The registering of the at least one external device may include installing an application related to the at least one external device, based on the registration request information.

The receiving of the measurement information may include classifying the received measurement information based on at least one of identification information of the host device, account information, and application information related to the at least one external device.

The managing of the at least one external device may include: generating management information for managing the at least one external device based on the received measurement information; and transmitting the generated management information to the host device.

The generating of the management information may include: determining a health state of a user by analyzing the received measurement information; and generating the management information for managing the at least one external device according to a result of the determining.

The managing of the at least one external device may include: generating a control command for controlling the at least one external device based on the received measurement information; and transmitting the generated control command to the at least one external device.

The transmitting of the generated control command may include transmitting the control command to the at least one external device through the host device.

The generating of the control command may include changing the control command according to a control protocol of the at least one external device.

The managing of the at least one external device may include: generating at least one of food recommendation information and exercise recommendation information based on the received measurement information; and transmitting at least one of the food recommendation information and the exercise recommendation information to the host device or the at least one external device.

The managing of the at least one external device may include: transmitting the received measurement information to a medical device connected to the management server; receiving diagnosis information corresponding to the measurement information from the medical device; and transmitting the received diagnosis information to the host device or the at least one external device.

The managing of the at least one external device may include, when consumables used in the at least one external device are insufficient or the at least one external device malfunctions, controlling the host device or the at least one external device to output an alarm signal.

The managing of the at least one external device may further include ordering the insufficient consumables from a sales server.

According to an aspect of another exemplary embodiment, a method of operating an external device, includes: requesting authorization by a management server, the requesting performed by at least one external server connected to a host device; when the authentication succeeds, transmitting measurement information measured by the at least one external device to the management server; receiving a control command, from the management server, generated based on the measurement information server; and performing the control command.

The requesting authentication may include: receiving authentication information from the host device; and transmitting the received authentication information to the management server.

The authentication information may include at least one of account information of the host device and identification information of the host device.

The receiving of the control command may include receiving the control command from the management server or the host device.

The performing of the control command may include outputting, from the at least one external device, at least one of an alarm, a warning, and recommendation information, changing a setting value, or updating a pre-installed program.

According to as aspect of another exemplary embodiment, a host device includes: a memory for storing at least one program; and a control unit for managing at least one external device by executing the at least one program, wherein the at least one program includes commands for: obtaining measurement information measured by the at least one external device; requesting authentication by the management server; transmitting the obtained measurement information to the management server when the authentication succeeds; receiving management information for managing the at least one external device, wherein the management information is generated based on the measurement information by the management server; and managing the at least one external device based on the received management information.

According to an aspect of another exemplary embodiment, a management server includes: an authentication unit for receiving an authentication request from a host device to which at least one external device is connected, and authenticating the host device in response to the authentication request; a communication unit for receiving measurement information measured by the at least one external device from the authenticated host device; and a control unit for managing the at least one external device based on the received measurement information.

According to an aspect of another exemplary embodiment, an external device includes: a memory for storing at least one program; and a control unit for performing a control command by executing the at least one program, wherein the at least one program includes commands for: requesting authentication by a management server; when the authentication succeeds, transmitting measurement information to the management server; receiving a control command generated based on the measurement information from the management server; and performing the control command.

According to an aspect of another exemplary embodiment, a computer-readable recording medium having recorded thereon a program for executing the method described above is included.

BRIEF DESCRIPTION OF THE DRAWINGS

These and/or other aspects will become apparent and more readily appreciated from the following description of the embodiments, taken in conjunction with the accompanying drawings in which:

FIGS. 9A through 9C are diagrams of a database of a management server, according to exemplary embodiments;

FIGS. 17A through 17C are diagrams for describing a management server collecting meal information of a user, according to an exemplary embodiment;

FIG. 26 is a diagram for describing a method of a management server providing exercise recommendation information, according to an exemplary embodiment;

FIG. 35 is a diagram for describing a method of a management server updating an external device, according to an exemplary embodiment;

DETAILED DESCRIPTION

Figure 1:
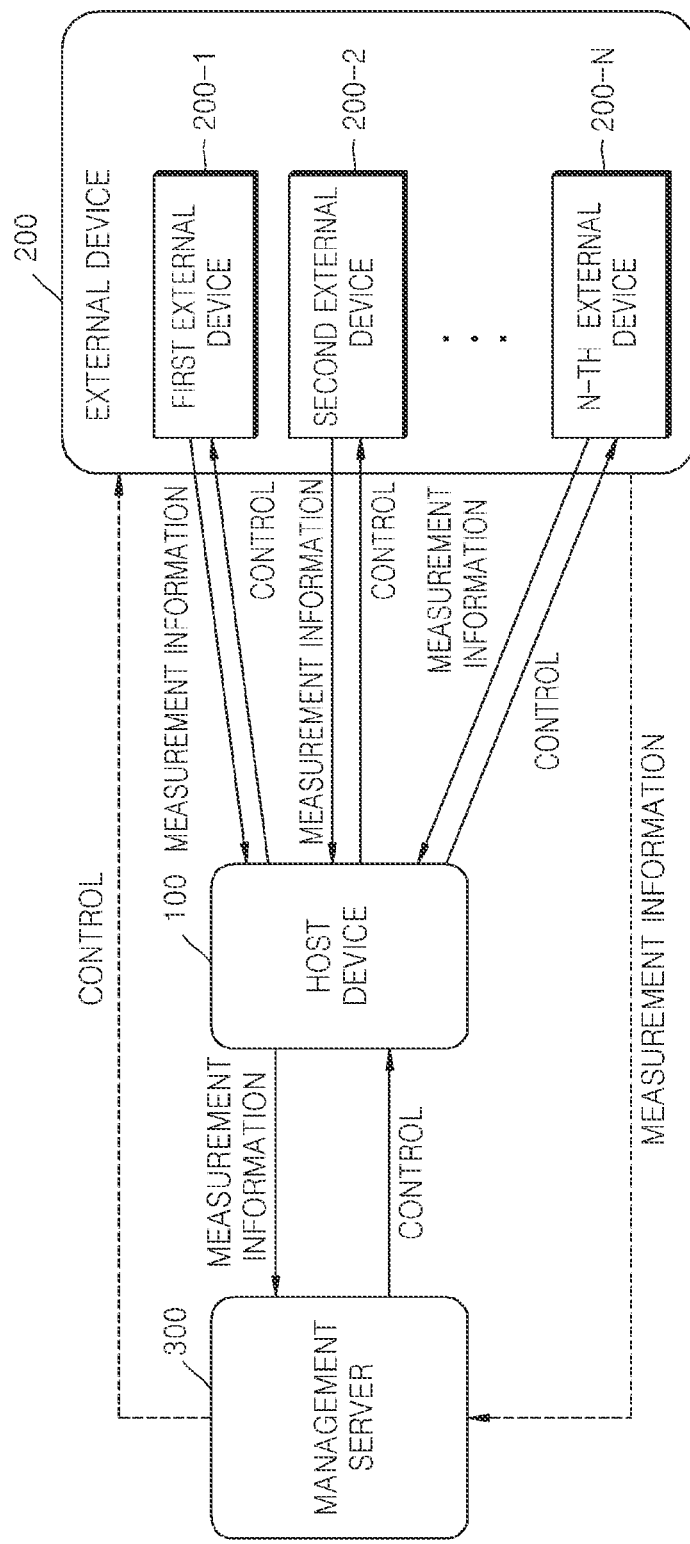
FIG. 1 is a block diagram of a system for managing an external device, according to an exemplary embodiment.

All terms including descriptive or technical terms which are used herein should be generally construed as having meanings that are obvious to one of ordinary skill in the art. However, the terms may be interpreted to have different meanings according to the intention of one of ordinary skill in the art, precedent cases, or the appearance of new technologies. Also, some terms may be arbitrarily defined by the applicant, and in this case, the meaning of the selected terms will be described in detail in the detailed description of the invention. Thus, the terms used herein should be defined based on the meaning of the terms together with the description throughout the specification.

Also, when a part "includes" or "comprises" an element, unless there is a particular description contrary thereto, the part may further include other elements. In the following description, terms such as "unit" and "module" indicate a unit for processing at least one function or operation, wherein the unit and the module may be embodied as hardware or software or may be embodied by combining hardware and software.

Throughout the specification, the term "application" means a group of computer programs designed to perform particular tasks. The applications described in the specification may be any of different types. For example, an application may be, but is not limited to, a game application, a musical instrument application, a moving picture reproduction application, a map application, a broadcasting application, an exercise support application, or a payment application.

Throughout the specification, the term "topology" means the arrangement of devices (or nodes). The topology may include physical topology and logical topology. That is, the topology may be defined according to physical or logical connections between the devices that belong to a topology structure. For example, different topologies may be defined by at least one of a cooperative relationship between the devices, a method of connecting the devices, a data transmission speed between the devices, a flow of data exchanged between the devices, a type of a signal exchanged between the devices, and a type of an application installed in each of the devices.

Also, throughout the specification, the definitions of a host terminal, a main external device, and a sub external device may be determined according to the position of devices, and an absolute or relative role of the devices within a topology structure. Thus, a device may operate as at least one of the host terminal, the main external device, and the sub external device in the topology structure.

One or more exemplary embodiments will now be described more fully with reference to the accompanying drawings. However, the one or more embodiments may be embodied in many different forms, and should not be construed as being limited to the descriptions set forth herein; rather, these descriptions are provided so that this disclosure will be thorough and complete, and will fully convey the concept of the one or more embodiments to those of ordinary skill in the art. In the following description, well-known functions or constructions are not described in detail since they would obscure the description of the one or more embodiments with unnecessary detail, and like reference numerals in the drawings denote like or similar elements throughout the specification.

As used herein, the term "and/or" includes any and all combinations of one or more of the associated listed items. Expressions such as "at least one of," when preceding a list of elements, modify the entire list of elements and do not modify the individual elements of the list.

FIG. 1 is a block diagram of a system for managing an external device, according to an exemplary embodiment.

As shown in FIG. 1, the system may include a host device 100, at least one external device 200, and a management server 300. However, components shown in FIG. 1 are not all essential, and the system may include more or fewer components.

For example, the system may further include at least one of a gateway for connecting the host device 100 to the at least one external device 200; a health information storage server such as an electronic medical record (EMR), an electronic health record (EHR), or a personal health record (PHR); a medical device such as a clinical decision system, a medical doctor device, or a hospital server; a caregiver server; and an external device server, as will be described in detail later.

The host device 100 may be connected to the at least one external device 200 via wires or wirelessly. In detail, according to an exemplary aspect, the host device 100 may be connected to the at least one external device 200 through short-range communication. Examples of short-range communication include a wireless local area network (WLAN) such as Wi-Fi, near field communication (NFC), Bluetooth, Bluetooth low energy (BLE), Zigbee, Wi-Fi direct (WFD), and an ultra wideband (UWB), but are not limited thereto.

The host device 100 may execute a predetermined application related to the external device 200 to control the external device 200. When a predetermined application is executed, the host device 100 may automatically search for and connect to the external device 200 related to the predetermined application. For example, the host device 100 may execute a healthcare application to control the external device 200.

The host device 100 may obtain measurement information measured by the external device 200 from the external device 200. Also, the host device 100 may generate a control command to be transmitted to the external device 200, according to a control protocol of the external device 200.

The host device 100 may communicate with the management server 300 via a wired or wireless network. Examples of a wired network include a LAN, a wide area network (WAN), and a value added network (VAN), and examples of a wireless network include a mobile communication network, a NFC network, and a satellite communication network.

The host device 100 may connect to the management server 300 by using account information, or identification (ID) information (such as a device ID, a serial number, or a media access control (MAC) address) of the host device 100. The host device 100 may transmit registration request information, for the external device 200 connected through a predetermined application, to the management server 300, or may transmit the measurement information obtained from the external device 200 to the management server 300. The host device 100 may receive a control command from the management server 300 and transmit the received control command to the external device 200.

The host device 100 may be any one of various devices. For example, the host device 100 described herein may be a mobile phone, a smart phone, a laptop, a tablet personal computer (PC), an electronic book terminal, a digital broadcasting terminal, a personal digital assistant (PDA), a portable multimedia player (PMP), a navigation system, a smart television (TV), or a consumer electronics (CE) device such as a refrigerator or air conditioner including a display panel, but is not limited thereto.

The external device 200 may be a device connected through an application executed by the host device 100. The number of external devices 200 may be one or more according to embodiments.

The external device 200 may be connected to the host device 100 through short-range communication. The external device 200 may transmit measurement information or input/output data to the host device 100 and receive a control command from the host device 100 through the short-range communication.

Herein, "measurement information" may denote results of the external device 200 measuring a user, an element or elements in the surroundings, or a surrounding environment. The external device 200 may measure the surrounding environment or a health state of the user by using various sensors.

Examples of the measurement information include health-related information of a user (such as blood sugar, blood pressure, a heart rate, a weight, meal information, exercise information, administration information, and sleep information), surroundings information (such as residual amounts of consumables, malfunctions, firmware version information, and updates), and surrounding environment information (such as a temperature, humidity, a weather, an air pollution level, and noise), but are not limited thereto.

The external device 200 may be directly connected to the management server 300, or indirectly connected to the management server 300 through the host device 100.

Accordingly, the external device 200 may transmit the measurement information directly to the management server 300 or indirectly to the management server 300 through the host device 100. Also, the external device 200 may receive a control command directly from the management server 300 or indirectly through the host device 100.

The external device 200 may vary. The external device 200 may include an input device, an output device, and a control device, and examples of the external device 200 include a medical device (for example a blood sugar meter or a blood pressure gauge), a sporting apparatus (for example, a bicycle, a treadmill, a hula hoop, a dumb-bell, or a smith machine), a CE device (for example, an air conditioner, an oven, a refrigerator, or a fan), a microphone, a speaker, a pedal, a joystick, a musical instrument (for example, a piano, an organ, an electronic keyboard, a guitar, a violin, or a cello), a game manipulation apparatus, or a doll.

The management server 300 is a server for managing the at least one external device 200 connected to the host device 100, and may be at least one of a cloud server, a personal server, and a medical institute server, but is not limited thereto.

The management server 300 may include an intelligent engine, and the management server 300 may analyze the measurement information measured by the external device 200 and provide information for controlling the external device 200 to the host device 100 through the intelligent engine. For example, when the external device 200 is a humidity measuring device, the management server 300 may control the external device 200 to measure humidity at one hour intervals when the user is at home, and to measure humidity at two hour intervals when the user is not at home.

When the management server 300 is a client server, the management server 300 may receive predetermined information from a separate service providing server or a device such as a medical institute server, a caregiver device, an external device provider server, an exercise information providing server, or a food recommendation server.

The management server 300 may authenticate the host device 100 and collect measurement information measured by the external device 200 through the authenticated host device 100. Also, the management server 300 may authenticate the external device 200 and receive the measurement information directly from the authenticated external device 200.

According to an aspect, the management server 300 may transmit management information for managing the external device 200 to the host device 100 such that the host device 100 manages the external device 200. According to another aspect, the management server 300 may directly manage the external device 200 based on the measurement information.

A method of the host device 100 registering and connecting the external device 200 will now be described with reference to FIG. 2.

Figure 2:
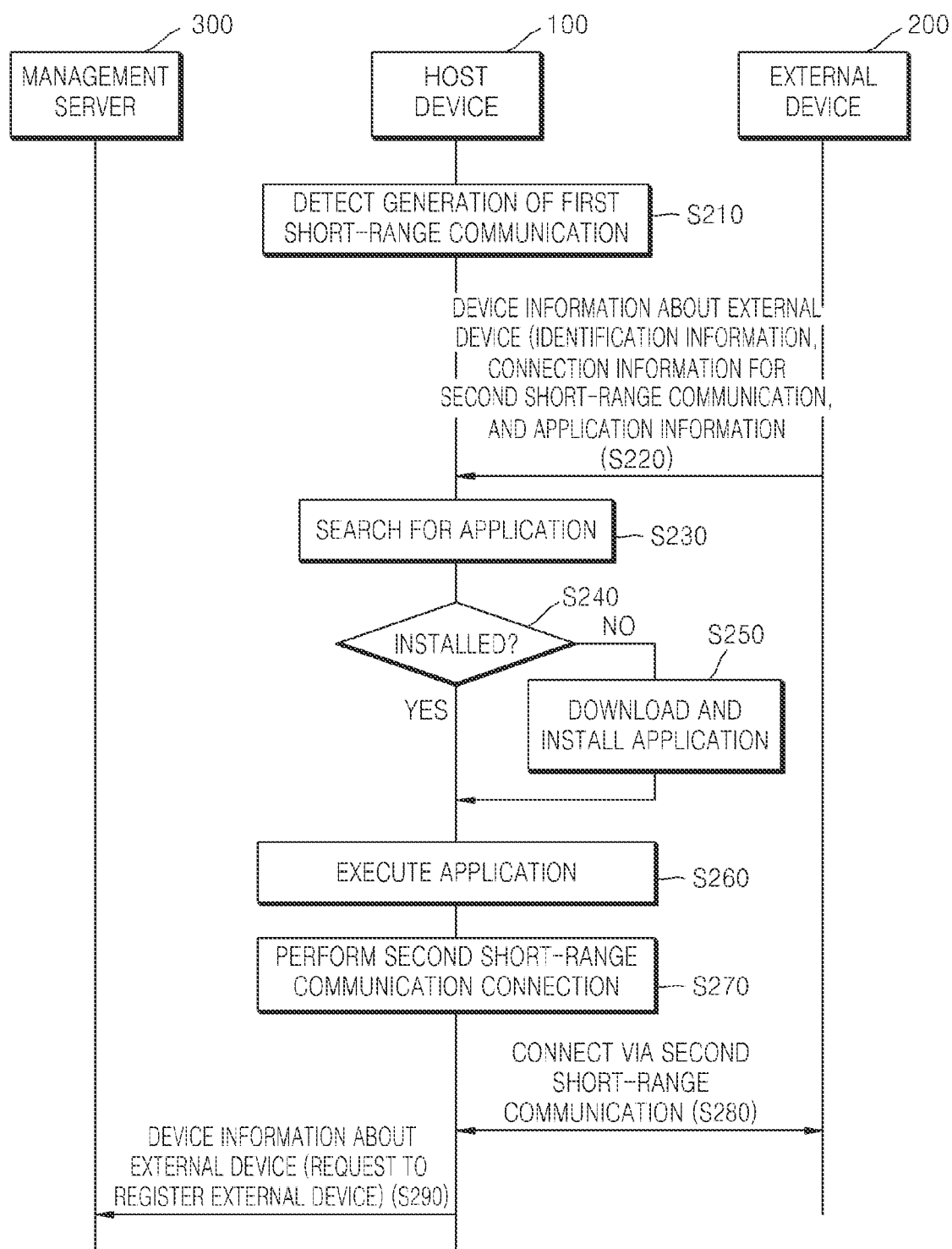
FIG. 2 is a flowchart illustrating a method of a host device registering and connecting an external device, according to an exemplary embodiment.

FIG. 2 is a flowchart illustrating a method of the host device 100 registering and connecting to the external device 200, according to an exemplary embodiment of the present invention.

In operation S210, the host device 100 may detect generation of first short-range communication. The first short-range communication may be NFC or BLE communication.

When the first short-range communication is NFC, the host device 100 may detect the generation of the first short-range communication if the external device 200 is within a radius of the NFC. When the first short-range communication is BLE communication, the host device 100 may detect the generation of the first short-range communication when the external device 200 receives a signal broadcasted based on Bluetooth communication.

In operation S220, the host device 100 may receive device information about the external device 200 through the first short-range communication. The device information about the external device 200 may include at least one of ID information of the external device 200, connection information for a second short-range communication, a type of the external device 200, capability provided by the external device 200, a category, and a protocol used to control the external device 200. Examples of the capability provided by the external device 200 include supportable communication capability, voice output capability, video output capability, voice recording capability, image capturing capability, and humidity detecting capability, but are not limited thereto.

The second short-range communication may be WLAN communication or Bluetooth communication, but is not limited thereto. WLAN (Wi-Fi) may include an infrastructure mode using an access point (AP), such as a wireless router, and an ad hoc mode for transmitting and receiving data in a peer to peer (P2P) manner without having to use an AP.

Accordingly, the connection information for the second short-range communication may include a communication method of the external device 200, connection information of the WLAN used by the external device 200 (for example, subsystem ID (SSID), an internet protocol (IP) address, a MAC address, a channel number, or a security key), a MAC address of the external device 200, a Bluetooth address of the external device 200, a product name of the external device 200, and profile information of the external device 200. Examples of the communication method include WLAN (an ad hoc mode or an infrastructure mode), Bluetooth, Zigbee, WFD, and UWB.

The device information about the external device 200 may further include application information. Examples of the application information include ID information of an application (for example, an application ID, an application name, and an application classification code), version information of an application, and link information of an application, but are not limited thereto.

In operation S230, the host device 100 may search for a pre-installed application related to the external device 200, based on the application information received from the external device 200. If it is determined that the application related to the external device 200 is not installed in operation S240, the host device 100 may download and install the application related to the external device 200 in operation S250.

The host device 100 may execute the application in operation S260. Also, in operation S270, the host device 100 may perform a second short-range communication connection. For example, when the second short-range communication is Bluetooth communication, the host device 100 may activate a Bluetooth communication module, and when the second short-range communication is WLAN communication, the host device 100 may activate a Wi-Fi module. Then, the host device 100 may request to be connected to the external device 200. In operation S280, when the external device 200 accepts the connection, the host device 100 and the external device 200 may be connected to each other via the second short-range communication.

In operation S290, the host device 100 may transmit the device information about the external device 200 to the management server 300 so as to register the external device 200 in the management server 300, as will be described in detail below with reference to FIG. 3.

Figure 3:
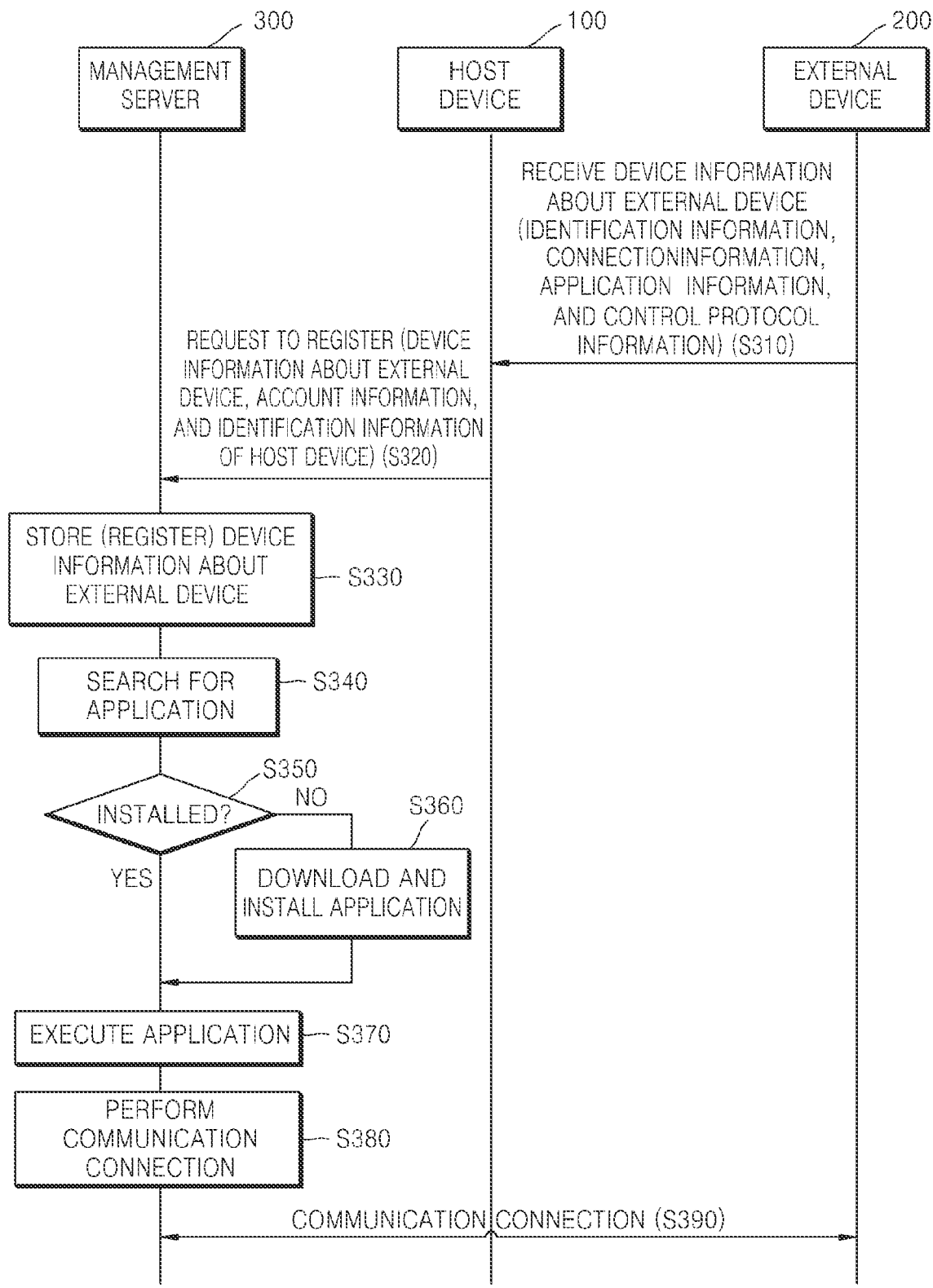
FIG. 3 is a flowchart illustrating a method of registering an external device in a management server, according to an exemplary embodiment.

FIG. 3 is a flowchart illustrating a method of registering the external device 200 in the management server 300, according to an exemplary embodiment.

In operation S310, the host device 100 may receive the device information about the external device 200 from the external device 200. The device information about the external device 200 may include ID information of the external device 200, connection information for connection to the external device 200, application information related to the external device 200, and control protocol information of the external device 200. Since operation S310 corresponds to operation S220 of FIG. 2, details thereof will not be repeated here.

In operation S320, the host device 100 transmits the device information about the external device 200 to the management server 300 while requesting that the management server 300 register the external device 200. Here, the host device 100 may transmit at least one of account information and ID information of the host device 100 to the management server 300.

In operation S330, the management server 300 may store the device information about the external device 200 in a list of registered external devices. Here, according to an embodiment, the management server 300 may map and manage at least one of the account information and the ID information of the host device 100, and ID information of the external device 200. A method of the management server 300 connecting to and registering an account of the external device 200 will be described in detail later with reference to FIG. 4.

In operation S340, the management server 300 may search for a pre-installed application related to the external device 200, based on the received application information. If it is determined that the application related to the external device 200 is not installed in operation S350, the management server 300 may download and install the application related to the external device 200 in operation S360.

In operation S370, the management server 300 may execute the application related to the external device 200. Then, in operation S380, the management server 300 may perform direct communication connection with the external device 200 based on the connection information. In other words, the management server 300 may request a communication connection with the external device 200, according to a communication method supported by the external device 200.

In operation S390, when the external device 200 accepts the communication connection, the management server 300 and the external device 200 may be directly connected to each other without having to use the host device 100. According to an embodiment, an order of operations S310 through S390 may be changed, or some operations may be skipped.

Figure 4:
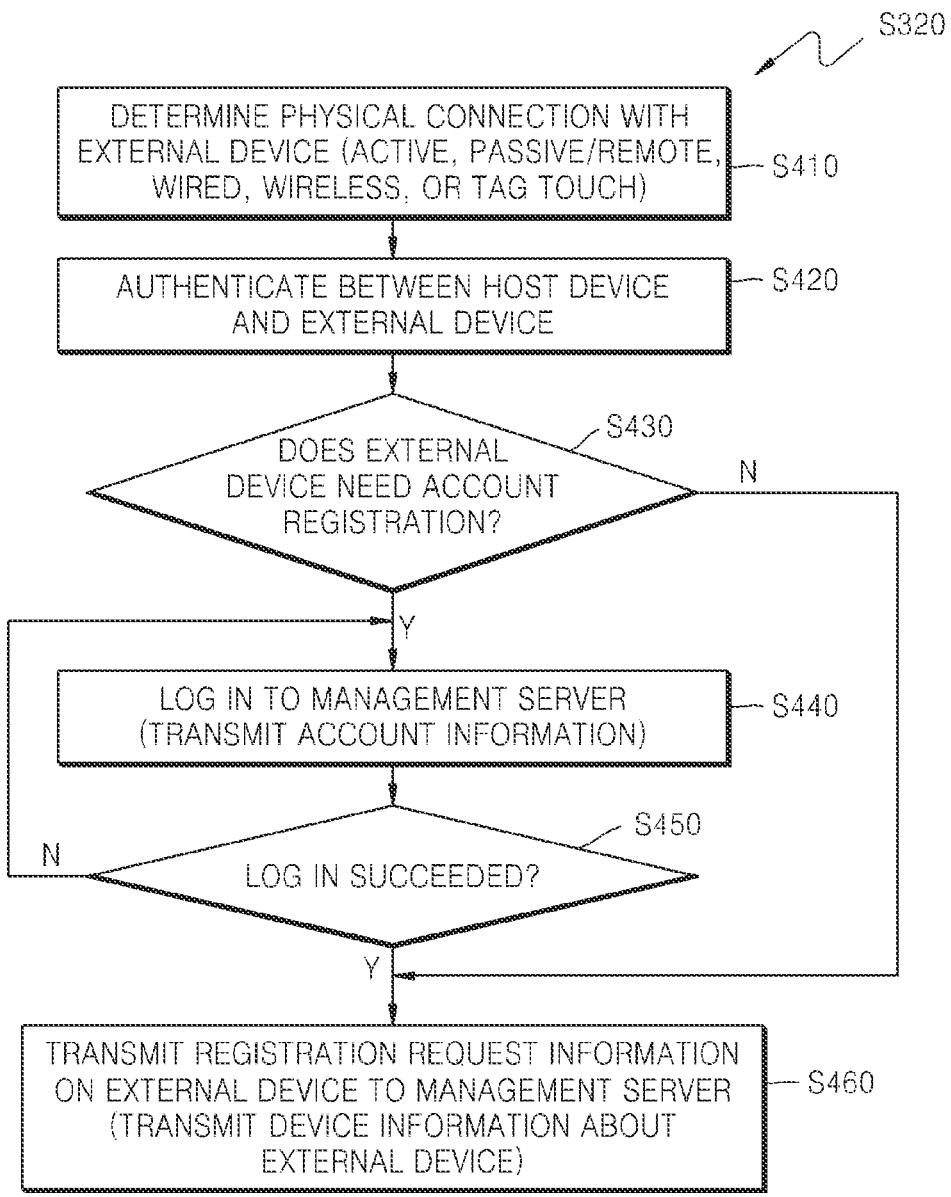
FIG. 4 is a flowchart illustrating a method of registering an external device in a management server by connecting the external device to an account, according to an exemplary embodiment.

FIG. 4 is a flowchart illustrating a method of registering the external device 200 in the management server 300 by connecting the external device 200 to an account, according to an exemplary embodiment.

In operation S410, the host device 100 may determine physical connection with the external device 200. The physical connection may be an active connection, a passive connection, a remote connection, a wired connection, a wireless connection, or a short-range communication connection.

In operation S420, the host device 100 may authenticate the external device 200. For example, the host device 100 may authenticate the external device 200 based on authentication information received from the external device 200.

The authentication information is used to authenticate whether the external device 200 is controllable by an application executed in the host device 100, or to authenticate whether the external device 200 is allowed to be connected to the host device 100. When the number of external devices 200 connectable to the host device 100 is N, the N external devices 200 may include the same number of pieces of authentication information.

The external device 200 may also authenticate the host device 100 based on authentication information received from the host device 100. The authentication information received from the host device 100 may be used to authenticate whether an application is installable in the host device 100 or to authenticate whether the host device 100 is allowed to receive measurement information measured by the external device 200.

In operation S430, the host device 100 may determine whether the external device 200 that is physically connected is an external device whose account needs to be registered. For example, when an account needs to be used for the external device 200 to synchronize measurement information with the management server 300, the host device 100 may determine that the external device is an external device whose account needs to be registered. Also, when an account registration request is received from an external device 200 that is physically connected, the host device 100 may determine that the external device 200 is an external device whose account needs to be registered.

When the external device 200 that is physically connected is an external device whose account needs to be registered, the host device 100 may log in to the management server 300 in operation S440. In other words, the host device 100 may transmit account information (for example, an ID and a password) to the management server 300.

If the login succeeds based on the account information of the host device 100 in operation S450, the host device 100 may transmit registration request information on the external device 200 to the management server 300 in operation S460. Here, the management server 300 may connect to and register the account information of the external device 200.

FIGS. 5A through 5D are diagrams of a user interface (UI) for automatically detecting the external device 200 and registering the external device 200 in the management server 300, according to an exemplary embodiment.

Figure 5A:
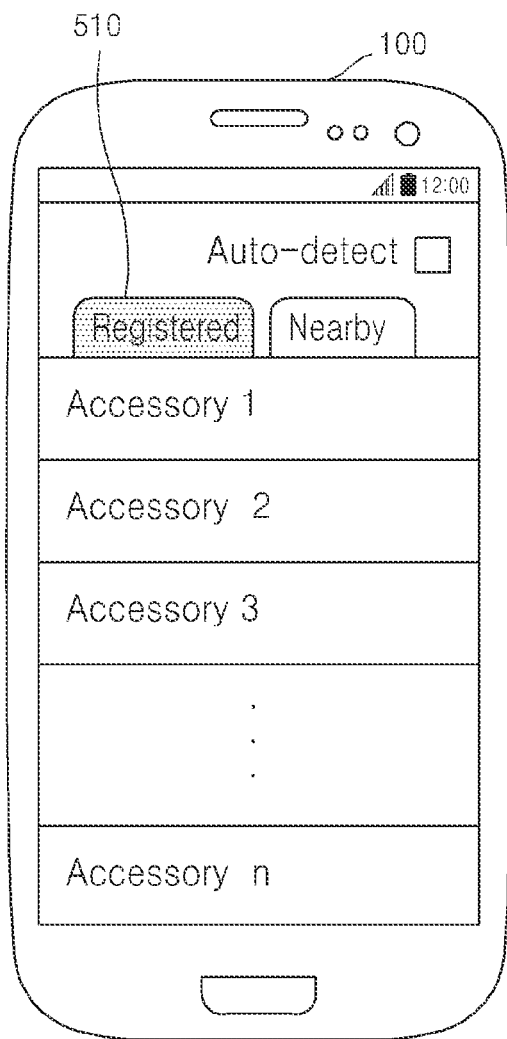
FIGS. 5A through 5D are diagrams of a user interface (UI) for automatically detecting an external device and registering the external device in a management server, according to an exemplary embodiment.

As shown in FIG. 5A, the host device 100 may provide a list 510 of external devices 200 registered in the management server 300 to a user. The user may determine whether information of his/her external device 200 is registered in the management server 300 through the list 510.

Figure 5B:
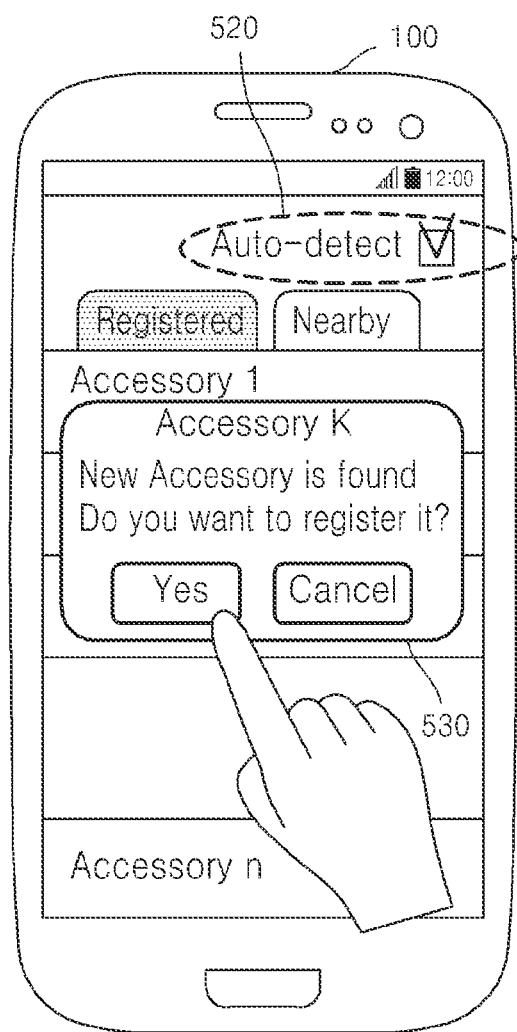

When "auto-detect" 520 is set as shown in FIG. 5B, the host device 100 may output a window 530 for inquiring whether to register the external device 200 (for example, Accessory K) in the management server 300 when the external device 200 is connected to the host device 100 via wires or wirelessly.

Figure 5C:
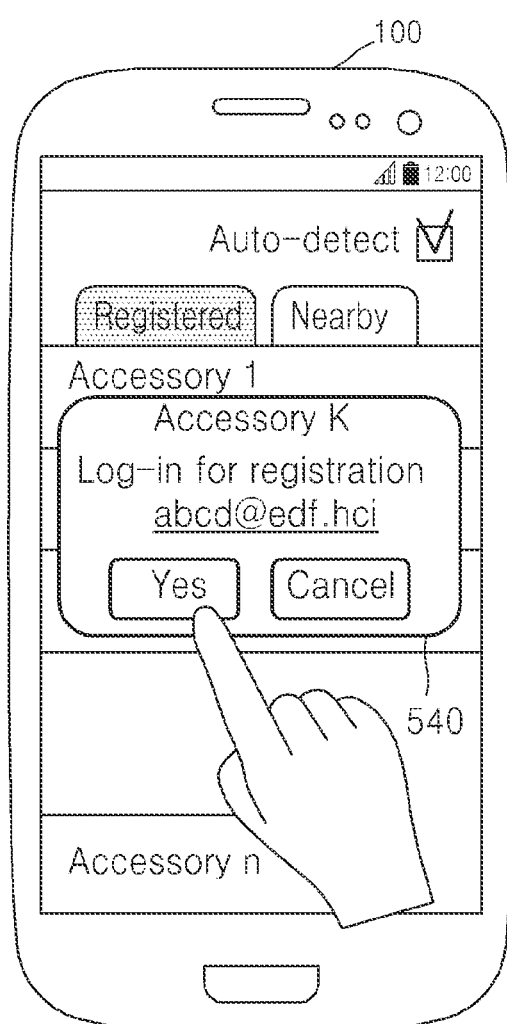

As shown in FIG. 5C, when the external device 200 (for example Accessory K) is a device whose account needs to be registered, the host device 100 may display a window 540 for the user to log in based on account information. The host device 100 may receive the account information (for example, ID: abcd@edf.hci, password: **) from the user and transmit the received account information to the management server 300, while requesting registration on the external device 200**.

Figure 5D:
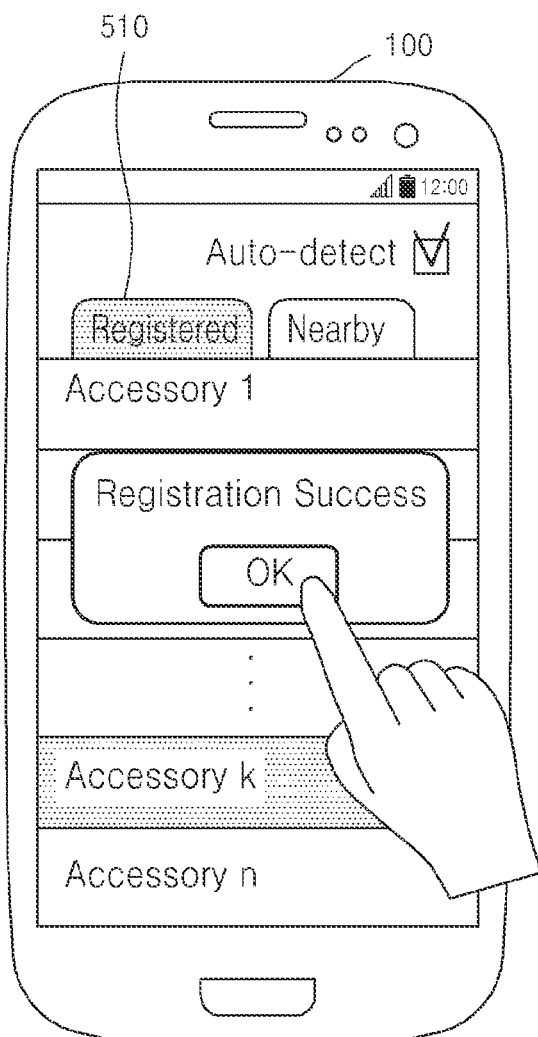

As shown in FIG. 5D, when the external device 200 (for example, Accessory K) is registered in the management server 300, the host device 100 may display the list 510 to which ID information (for example, 'Accessory K') of the newly registered external device 200 is added.

FIGS. 6A through 6D are diagrams of a UI for registering the external device 200 in the management server 300, according to an exemplary embodiment.

Figure 6A:
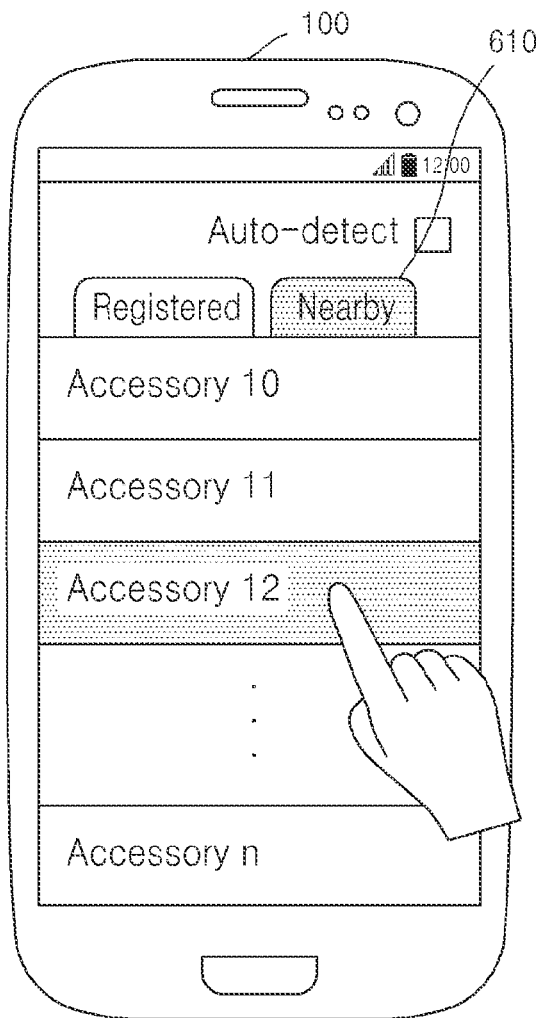
FIGS. 6A through 6D are diagrams of a UI for registering an external device in a management server, according to an exemplary embodiment.

As shown in FIG. 6A, when "auto-detect" is not set, the host device 100 may not output the "auto-detect" 520 even when the external device 200 is found in the vicinity of the host device 100, but may add and manage ID information of the external device 200 to a list 610 of external devices found nearby the host device 100. When a user gesture requesting for the list 610 is detected, the host device 100 may provide the list 610. Here, the user may select and register an external device, such as Accessory 12, from the list 610.

Figure 6B:
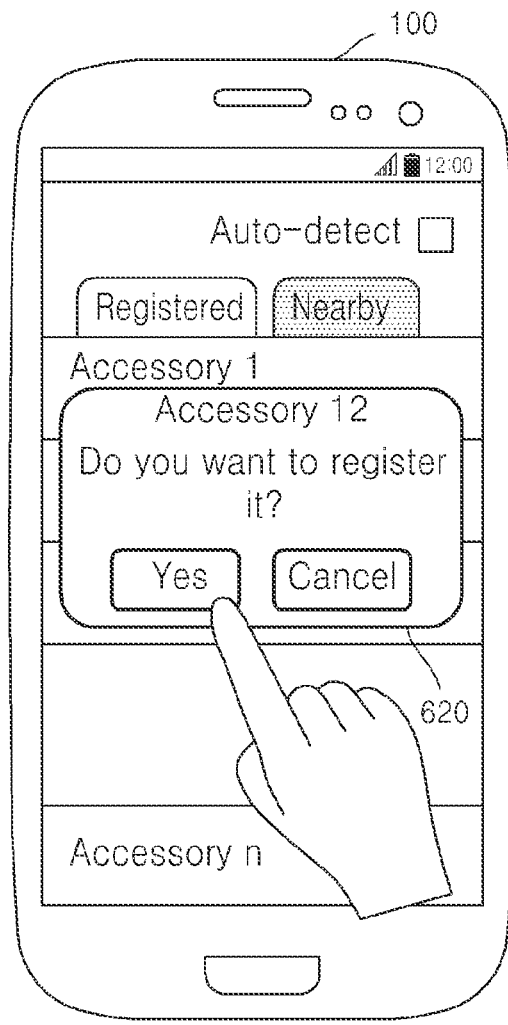

As shown in FIG. 6B, when a selection (for example, a tap gesture) of the user on the Accessory 12 from the list 610 is detected, the host device 100 may output a window 620 inquiring whether to register the Accessory 12 in the management server 300. Here, the host device 100 may receive a registration request of the user on the Accessory 12.

Figure 6C:
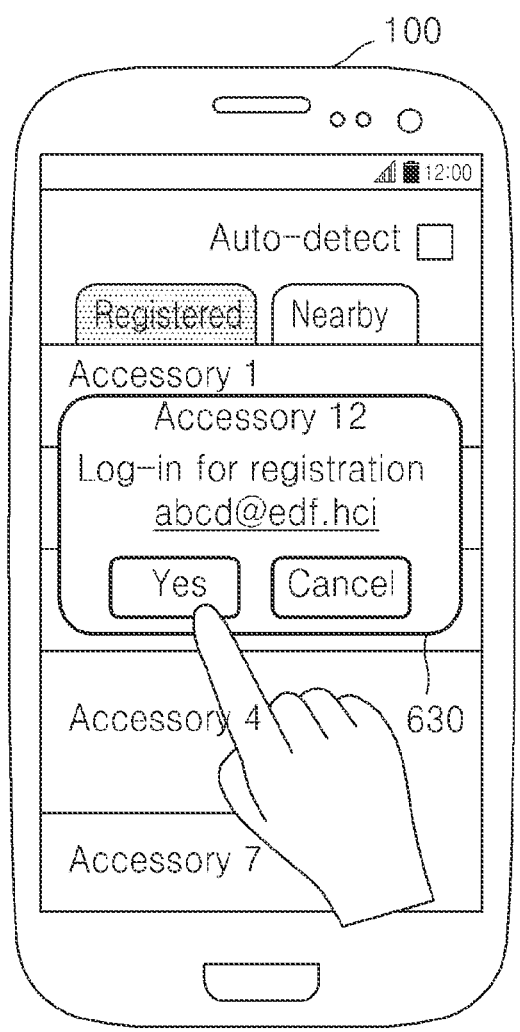

As shown in FIG. 6C, when the Accessory 12 is a device whose account needs to be registered, the host device 100 may display a window 630 for the user to input account information. The host device 100 may receive the account information (for example, ID: abcd@edf.hci, password: **) from the user and transmit the received account information to the management server 300**, while requesting to register the Accessory 12.

Figure 6D:
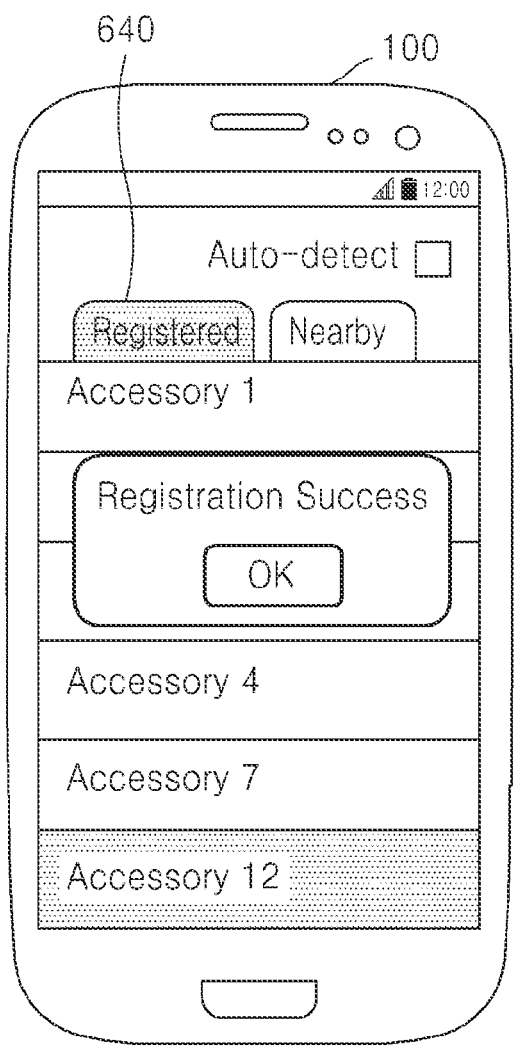

As shown in FIG. 6D, when the Accessory 12 is registered in the management server 300, the host device 100 may display a list 640 of external devices, to which ID information (for example, 'Accessory 12') of the newly registered external device, is added.

FIGS. 7A through 7D are diagrams of a UI for providing information about the external device 200, according to an exemplary embodiment.

Figure 7A:
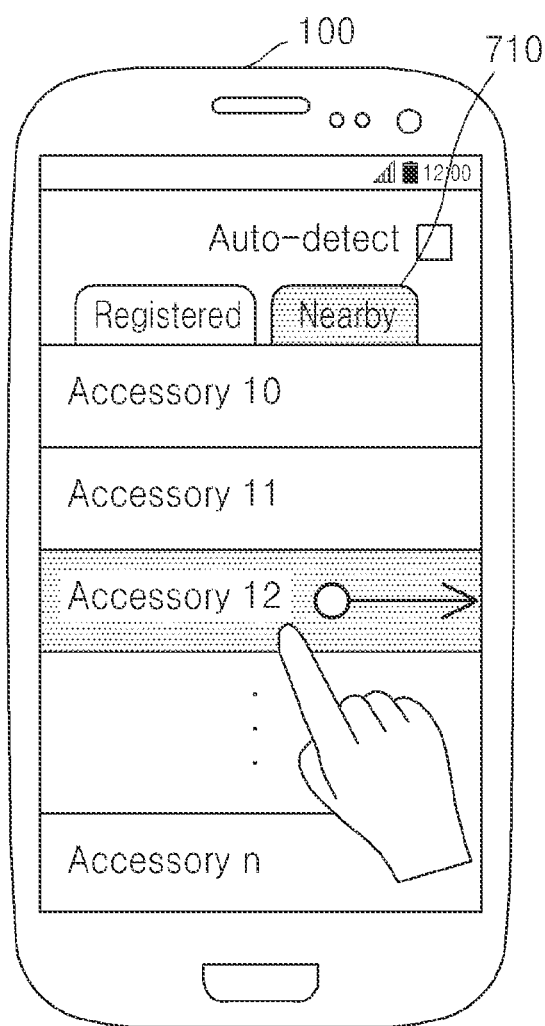
FIGS. 7A through 7D are diagrams of a UI for providing information about an external device, according to an exemplary embodiment.

As shown in FIG. 7A, when a user gesture requesting a list 710 of external devices found nearby is detected, the host device 100 may provide the list 710. Here, the user may select an external device, such as Accessory 12, from the list 710.

Figure 7B:
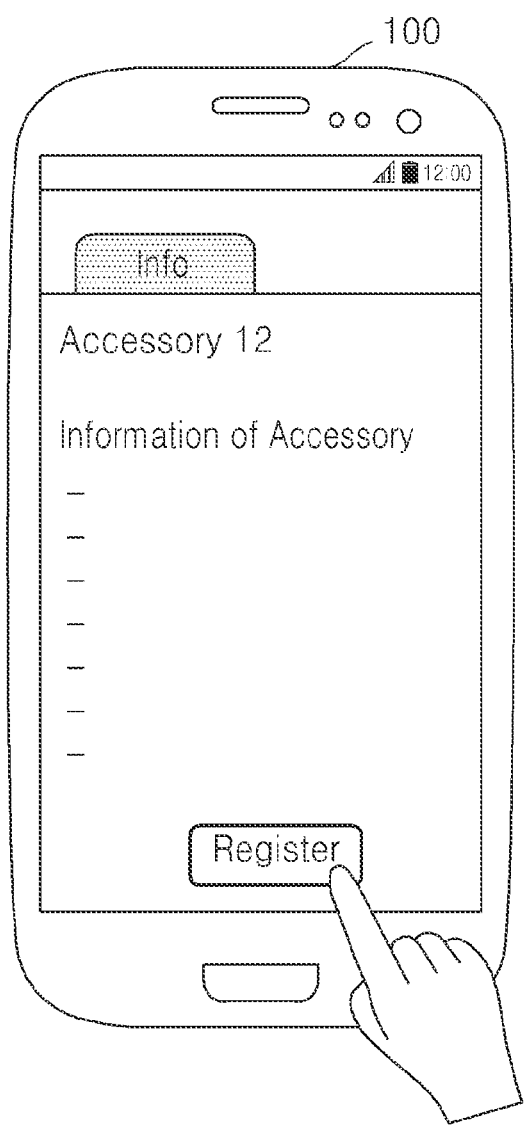

As shown in FIG. 7B, when a selection (for example, a swipe gesture) of the user on the Accessory 12 is detected from the list 710, the host device 100 may provide detailed information about the Accessory 12. For example, the host device 100 may provide ID information of a selected external device, a type of a selected external device, capability provided by a selected external device, and information about a category. Here, the user may check the detailed information about the Accessory 12, and determine whether to register Accessory 12 in the management server 300.

Figure 7C:
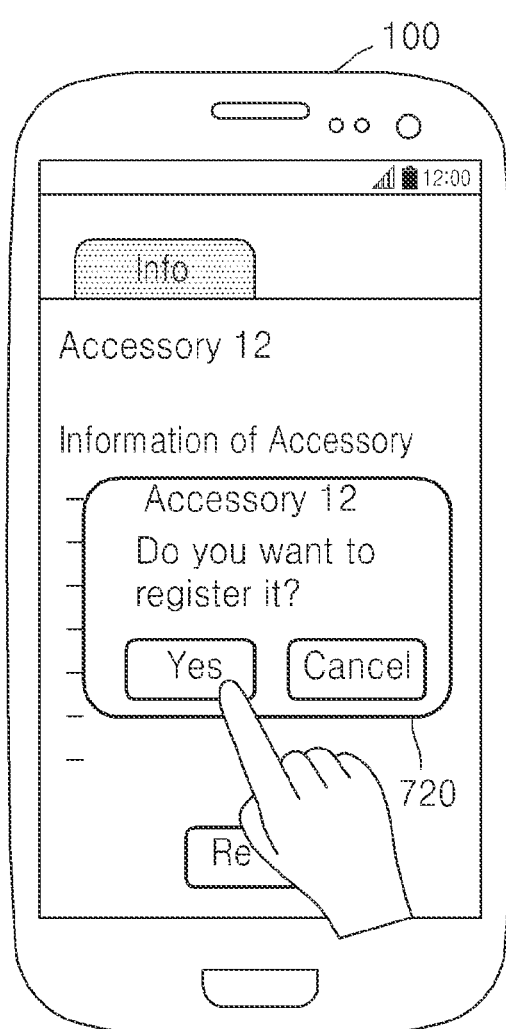

As shown in FIG. 7C, the host device 100 may output a window 720 inquiring whether to register the Accessory 12 in the management server 300. Also, the host device 100 may receive a registration request of the user on the Accessory 12.

Figure 7D:
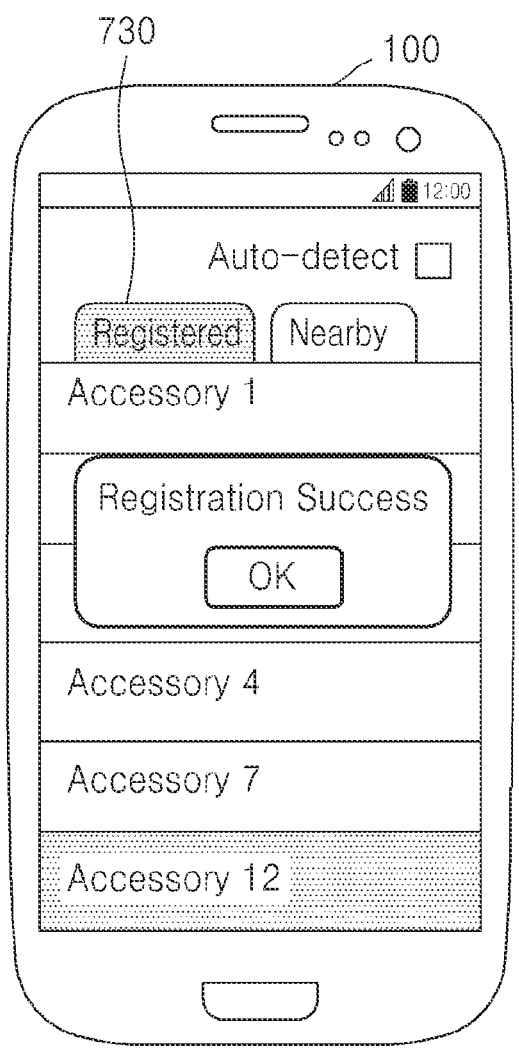

As shown in FIG. 7D, when the Accessory 12 is registered in the management server 300, the host device 100 may display a list 730 of registered external devices to which ID information (for example, 'Accessory 12') of the newly registered external device is added.

Figure 8A:
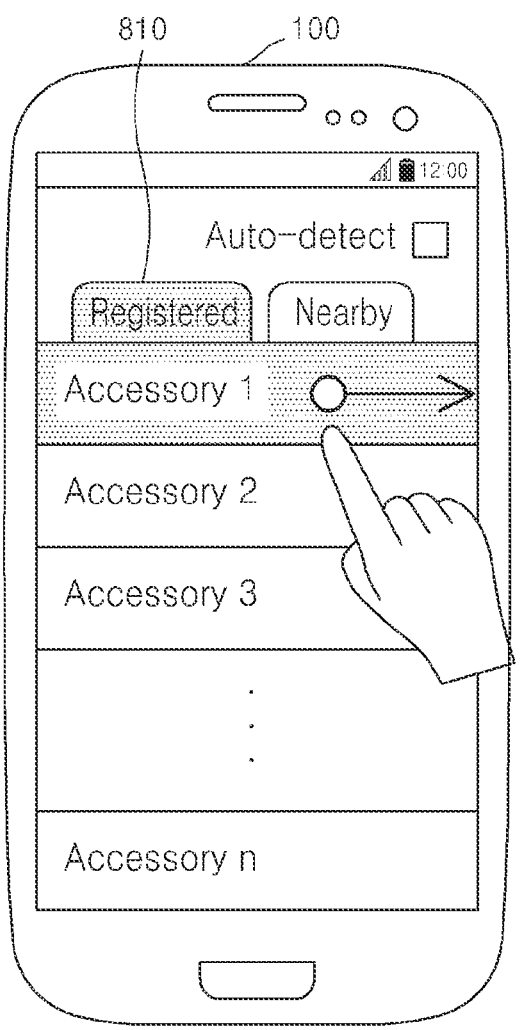
FIGS. 8A through 8C are diagrams of a UI for releasing registration of an external device, according to an exemplary embodiment.
Figure 8B:
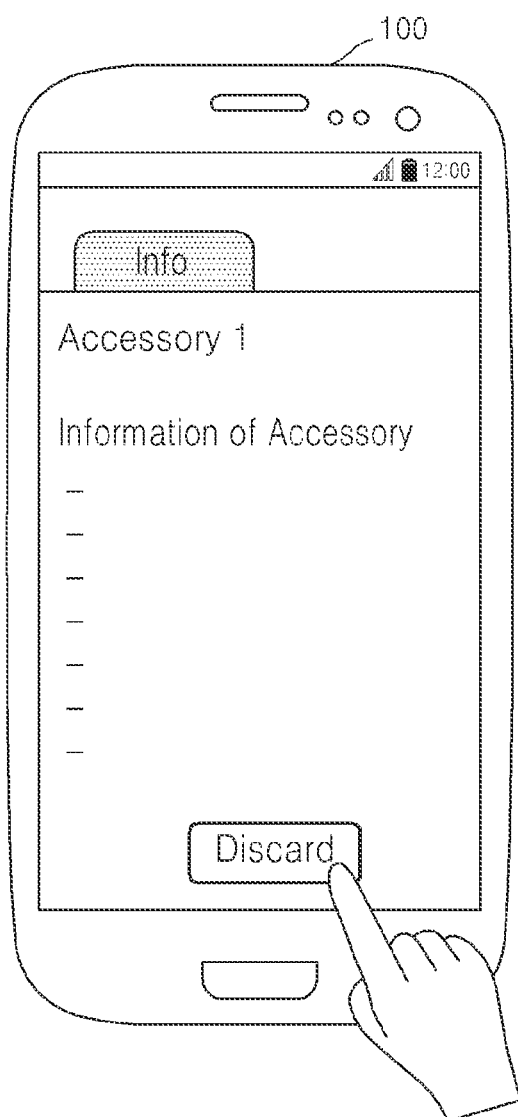
Figure 8C:
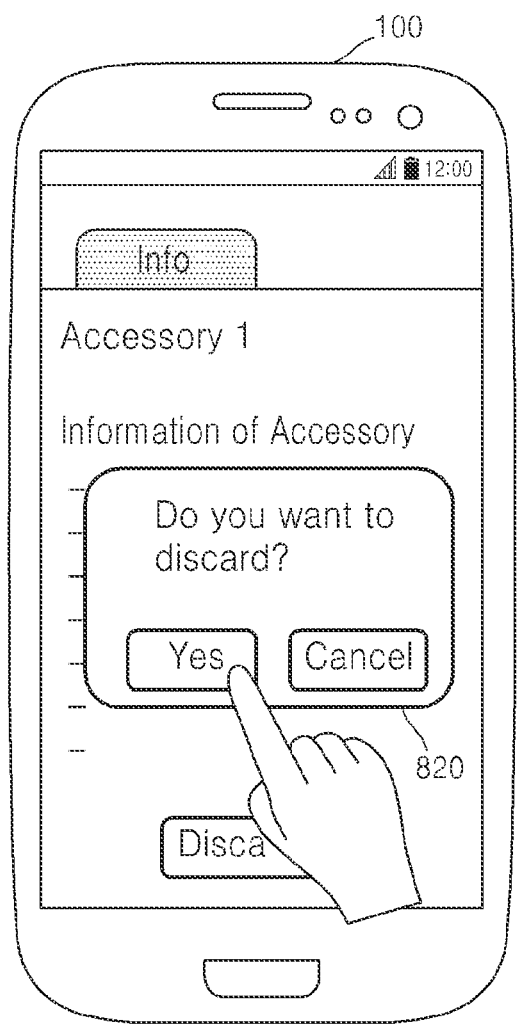

FIG. 8A through 8C are diagrams of a UI for releasing registration of the external device 200, according to an exemplary embodiment.

As shown in FIG. 8A, the host device 100 may provide a list 810 of external devices registered in the management server 300 to a user. Here, the host device 100 may detect a user input (for example, a swipe gesture) for selecting an external device, such as Accessory 1, from the list 810.

As shown in FIG. 8B, the host device 100 may provide detailed information about the Accessory 1. For example, the host device 100 may provide ID information of a selected external device, a type of a selected external device, capability provided by a selected external device, and information about a category. Here, the user may check the detailed information and determine whether to release the registration of the Accessory 1.

As shown in FIG. 8C, the host device 100 may output a window 820 inquiring whether to release the registration of the Accessory 1. Also, the host device 100 may receive a registration release request of the user on the Accessory 1. Here, the host device 100 may transmit the registration release request to the management server 300, and delete the Accessory 1 from the list 810.

Figure 9B:
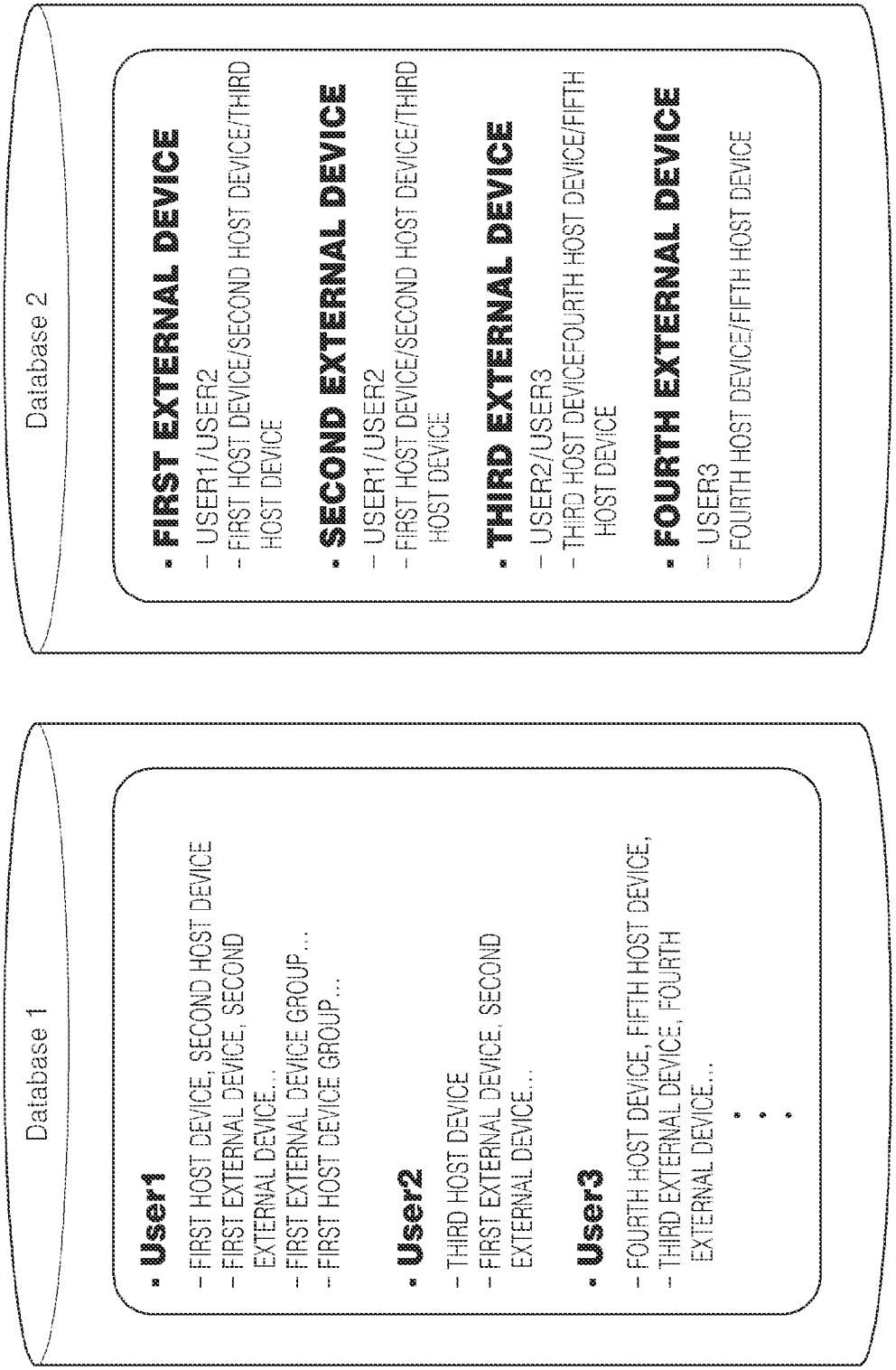

FIGS. 9A through 9C are diagrams of a database (DB) of the management server 300, according to exemplary embodiments.

As shown in FIG. 9A, according to an embodiment, the management server 300 may hierarchically manage the external devices 200 by mapping the external devices 200 to account information and ID information of the host device 100. A plurality of host devices may be connected to one account or a plurality of external devices may be connected to one host device. Alternatively, one external device may be connected to a plurality of host devices or a plurality of accounts. For example, a scale that is the external device 200 may be connected to each of a mother's device (or a mother's account) or a father's device (or a father's account). Thus, a family may commonly use the external device 200, i.e., the scale. Here, measurement information measured by the external device 200, i.e., the scale, may be managed according to accounts.

As shown in FIG. 9B, according to another embodiment, the management server 300 may classify and manage the host device 100 or the external device 200 according to accounts (refer to Database 1), or may classify and manage the host device 100 or accounts according to external devices (refer to Database 2).

Also, the management server 300 may set and manage a plurality of external devices as one external device group, or set and manage a plurality of host devices as one host device group.

Alternatively, the management server 300 may manage information about the registered external device 200 by using an inner storage unit or an external server.

As shown in FIG. 9C, according to another embodiment, the management server 300 may add a flag 910 to an external device 200 that transmitted measurement information to the management server 300, from among the registered external devices 200. Here, the management server 300 may manage the measurement information measured by the external device 200. The measurement information may include at least one of physical information, administration information, environment information, meal information, exercise information, and state information of consumables used in an external device. A method of the management server 300 collecting measurement information measured by the external device 200 will now be described in detail.

Figure 10:
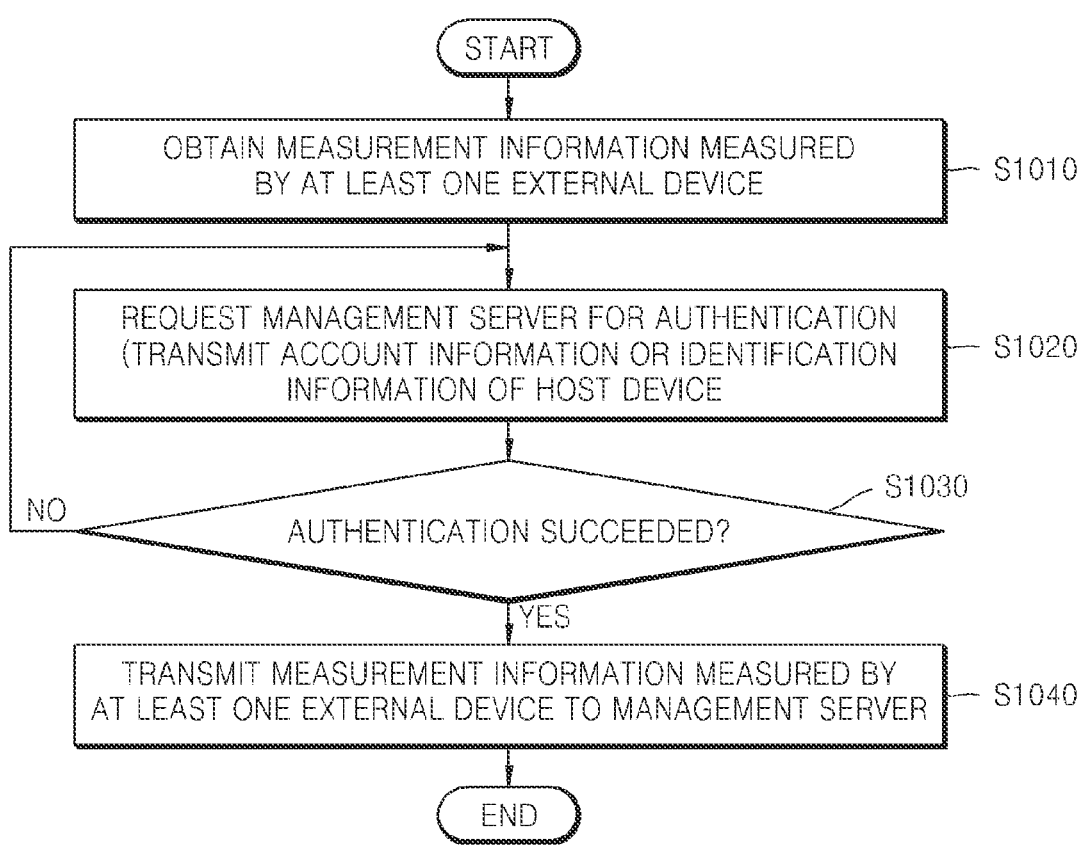
FIG. 10 is a flowchart illustrating a method of a host device transmitting measurement information to a management server, according to an exemplary embodiment.

FIG. 10 is a flowchart illustrating a method of the host device 100 transmitting measurement information to the management server 300, according to an exemplary embodiment.

In operation S1010, the host device 100 may obtain measurement information measured by the at least one external device 200. According to an embodiment, the host device 100 may receive the measurement information from the external device 200 through a wired communication, a wireless communication, or a short-range communication (for example, Bluetooth or WLAN).

In operation S1020, the host device 100 may request authentication from the management server 300. For example, the host device 100 may request authentication any may transmit at least one of account information and ID information of the host device 100 to the management server 300.

In operation S1030, the host device 100 may determine whether the authentication succeeds based on a response of the management server 300 regarding the request. If the authentication failed, the host device 100 may request authentication again by transmitting the account information and/or the ID information of the host device 100 to the management server 300.

In operation S1040, if the authentication succeeded, the host device 100 may transmit the measurement information measured by the at least one external device 200 to the management server 300. Here, the host device 100 may transmit only a part of the obtained measurement information to the management server 300.

In other words, according to an embodiment, the management server 300 may collect the measurement information measured by the external device 200 only through the authenticated host device 100. For example, since it is important secure health information, such as personal medical information or personal physical information, only the authenticated host device 100 is able to transmit the measurement information to the management server 300, as will be described in detail with reference to FIG. 11.

Figure 11:
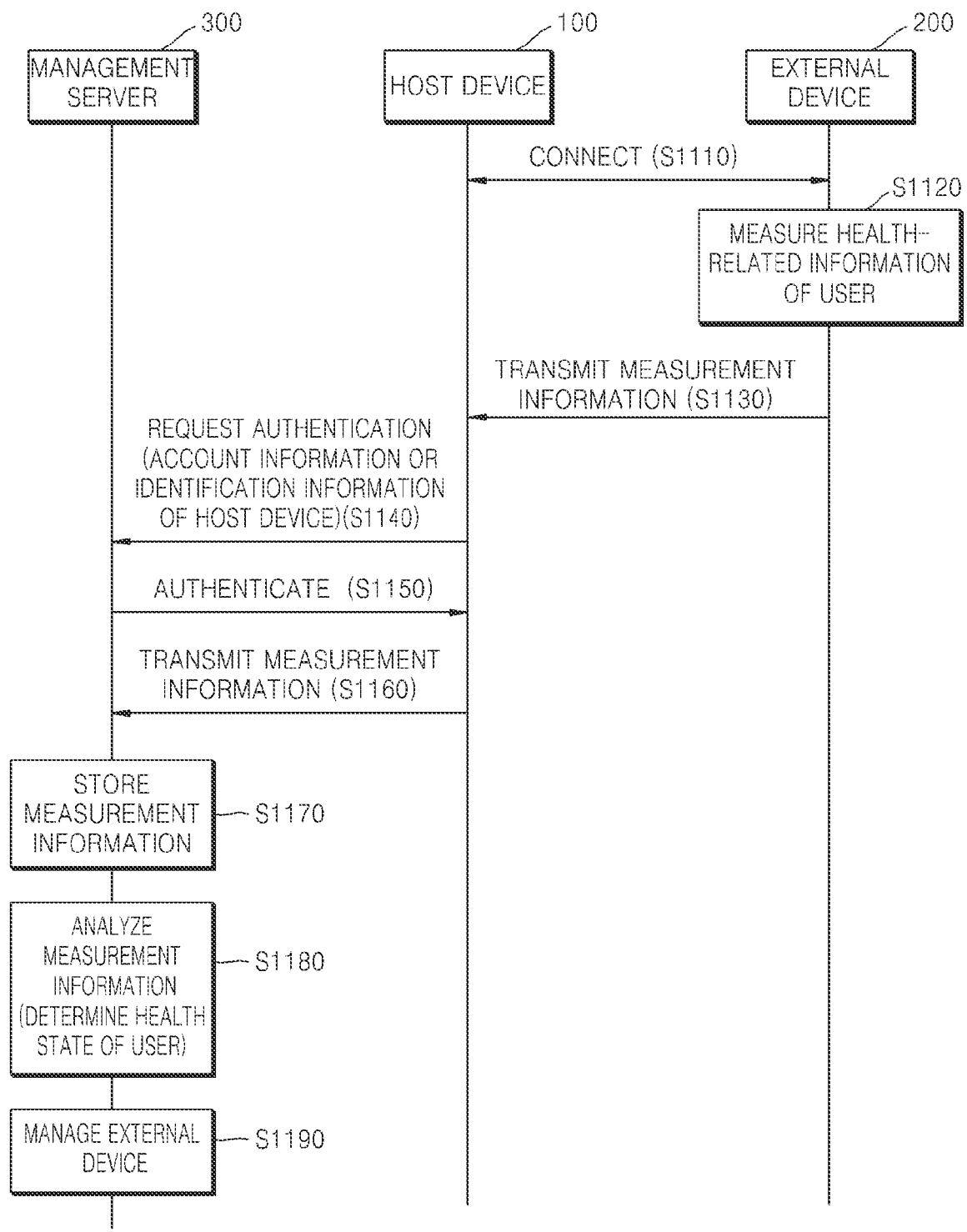
FIG. 11 is a flowchart illustrating a method of a management server receiving measurement information of an external device through an authenticated host device, according to an exemplary embodiment.

FIG. 11 is a flowchart illustrating a method of the management server 300 receiving measurement information of the external device 200 through the authenticated host device 100, according to an exemplary embodiment.

In operation S1110, the host device 100 may be connected to the external device 200 through second short-range communication (for example, Bluetooth or WLAN). Then, in operation S1120, the external device 200 may measure health-related information of a user. Here, the measuring may include collecting surrounding environment information or receiving information from the user. According to an embodiment, an order of operations S1110 and S1120 may be changed.

In operation S1130, the external device 200 may transmit the measurement information to the host device 100. The host device 100 may transmit the measurement information periodically or when a certain event is generated. Examples of the certain event include an input event from the user and an event generated when a measured value exceeds a predetermined range.

The external device 200 may encode and transmit the measurement information to the host device 100.

In operation S1140, when the measurement information is received from the external device 200, the host device 100 may request to be authenticated by the management server 300. For example, the host device 100 may request authentication while transmitting at least one of account information (ID and password) and ID information of the host device 100 to the management server 300.

In operation S1150, the management server 300 may perform authentication based on at least one of the account information and the ID information of the host device 100, in response to the authentication request of the host device 100. For example, the management server 300 may compare the account information or ID information received from the host device 100 with pre-registered information, and perform authentication of the host device 100.

In operation S1160, if the authentication succeeds, the host device 100 may transmit the measurement information obtained from the external device 200 to the management server 300. According to an embodiment, whenever the measurement information is transmitted to the management server 300, the host device 100 may request to be authenticated by the management server 300. Also, the host device 100 may transmit the measurement information to the management server 300 several times based on having been authenticated once if the connection to the management server 300 is maintained.

In operation S1170, the management server 300 may store the measurement information. Here, the management server 300 may classify and store the measurement information according to the external devices 200, according to account information, or according to the host devices 100.

In operation S1180, the management server 300 may analyze the measurement information. In operation S1190, the management server 300 may manage the at least one external device 200 based on the measurement information. Here, the management server 300 may determine a health state of the user by using the measurement information, or may generate food recommendation information, exercise recommendation information, a warning, or an alarm for the user, as will be described in detail below.

Figure 12:
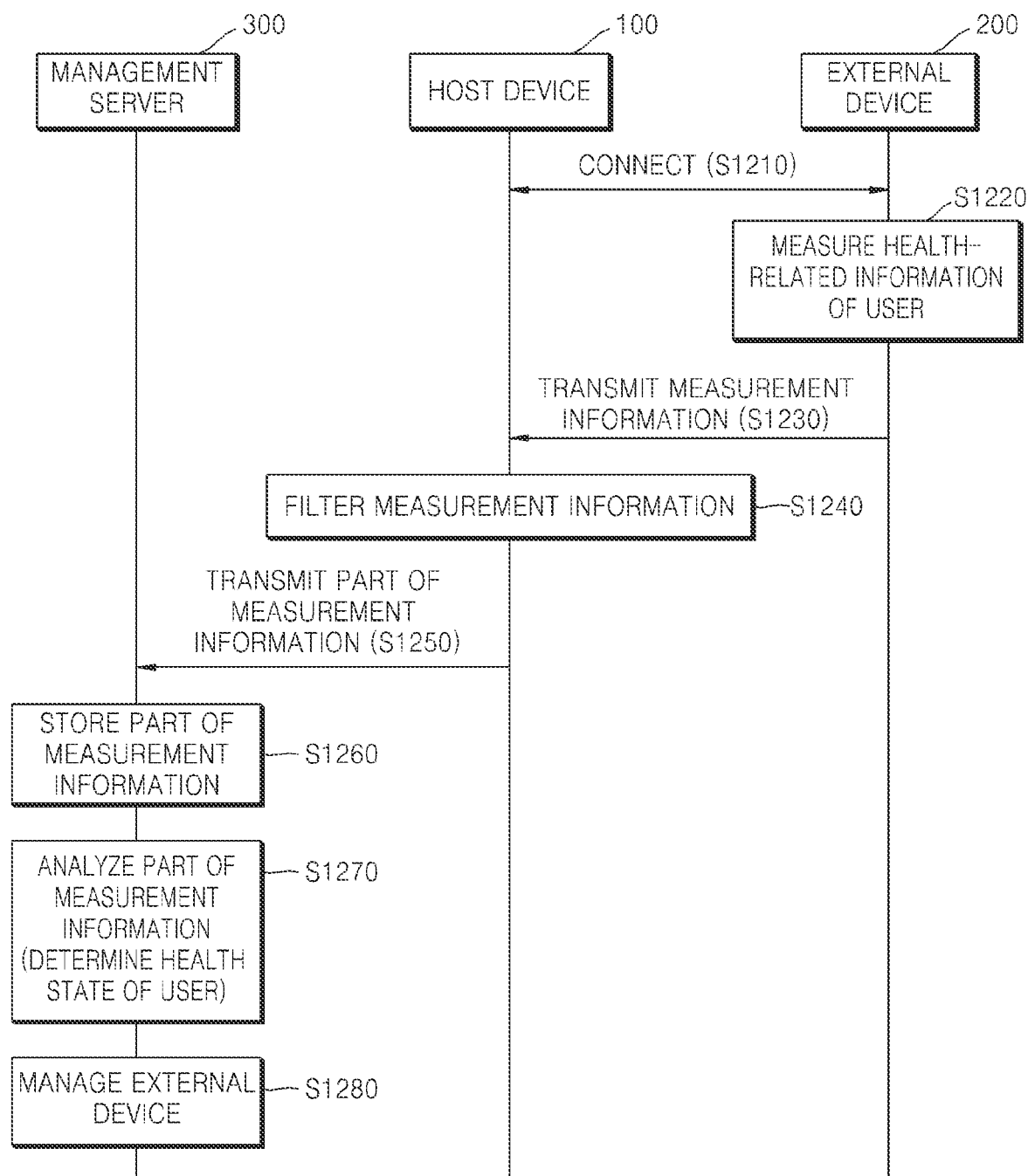
FIG. 12 is a flowchart illustrating a method of a host device filtering measurement information to be transmitted to a management server, according to an exemplary embodiment.

FIG. 12 is a flowchart illustrating a method of the host device 100 filtering measurement information to be transmitted to the management server 300, according to an exemplary embodiment.

In operation S1210, the host device 100 may be connected to the external device 200 via a wired or wireless communication. In operation S1220, the external device 200 measures health-related information of a user, and in operation S1230, the host device 100 may receive measurement information measured by the external device 200. Since operations S1210 through S1230 correspond to operations S1110 through S1130 of FIG. 11, details thereof will not be repeated here.

In operation S1240, the host device 100 may filter the obtained measurement information according to a predetermined standard. According to an embodiment, the host device 100 may extract a part of the measurement information based on whether the at least one external device 200 that transmitted the measurement information is a medical device. For example, the host device 100 may classify the measurement information measured by the external device 200 defined to be a medical device not to be transmitted to the management server 300. In other words, since measurement information measured by the medical device is very private information, the host device 100 may block the measurement information from being transmitted to the management server 300 to prevent the measurement information from being exposed.

Alternatively, the host device 100 may filter the measurement information based on whether a route for transmitting the measurement information is a secure network. For example, the host device 100 may extract only measurement information obtained through a secure network as the part of measurement information to be transmitted to the management server 300.

According to another embodiment, the host device 100 may extract a part of the measurement information based on a pre-set type of measurement information. For example, the host device 100 may pre-receive a selection of the user with respect to a type of measurement information to be transmitted to the management server 300. Also, the host device 100 may compare the type of the obtained measurement information and the type of the pre-selected measurement information to filter the obtained measurement information.

In operation S1250, the host device 100 may transmit the part of measurement information to the management server 300. In operation S1260, the management server 300 may store the part of measurement information in a DB. Also, in operation S1270, the management server 300 may analyze the part of measurement information to determine a health state of the user. In operation S1280, the management server 300 may manage the at least one external device 200 based on the part of the measurement information.

Figure 13:
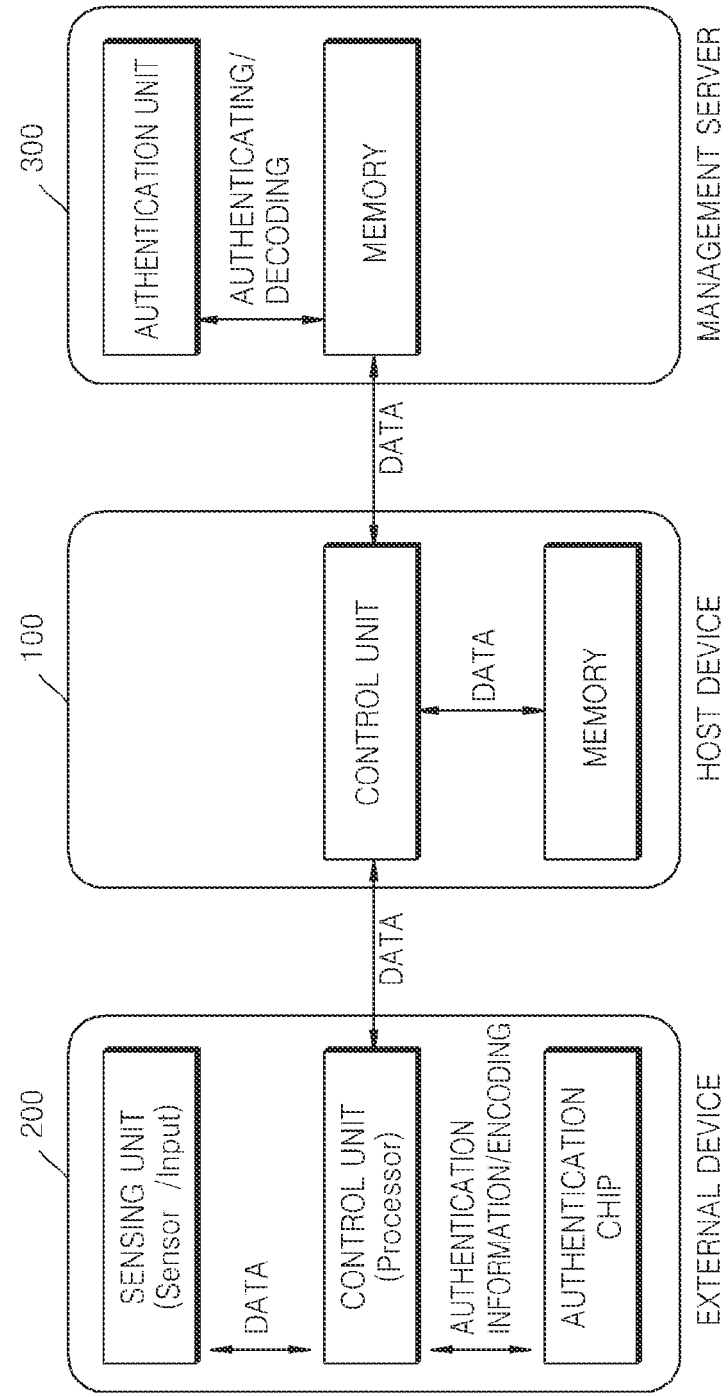
FIG. 13 is a diagram for describing a method of filtering measurement information based on whether an external device is a medical device, according to an exemplary embodiment.

FIG. 13 is a diagram for describing a method of filtering measurement information based on whether the external device 200 is a medical device, according to an exemplary embodiment.

As shown in FIG. 13, the external device 200 may include a sensing unit, a control unit, and an authentication chip. The sensing unit may measure a surrounding environment or a health state of a user by using various sensors, or may detect information input from the user.

The control unit may transmit measurement information sensed by the sensing unit to the host device 100, together with authentication information stored in the authentication chip. Here, the authentication information stored in the authentication chip may include identification code indicating that the external device 200 is a medical device.

Accordingly, the host device 100 may check the authentication information received from the external device 200, and determine that the external device 200 that transmitted the measurement information is a medical device. When the external device 200 that transmitted the measurement information is determined to be a medical device, the host device 100 may not transmit the measurement information to the management server 300.

Meanwhile, in order to secure the measurement information, the external device 200 may encode the measurement information by using an encoding code pre-negotiated with the management server 300 or the medical device (for example, a doctor's device, a pharmacist's terminal, or a medical institute server), and transmit the encoded measurement information to the host device 100. Here, the pre-negotiated encoding code may be stored in the authentication chip.

When the encoded measurement information is received from the external device 200 through the host device 100, the management server 300 may decode the encoded measurement information through an authentication module and store the decoded measurement information in a storage unit. The external device 200 may directly transmit the encoded measurement information to the management server 300.

Also, when the measurement information is medical data, the external device 200 may encode the measurement information according to a medical information standard (for example, HL7, DICOM, or IEEE11073), and transmit the encoded measurement information to the host device 100. When the host device 100 transmits the encoded measurement information to the management server 300, the management server 300 may decode the encoded measurement information.

Figure 14B:
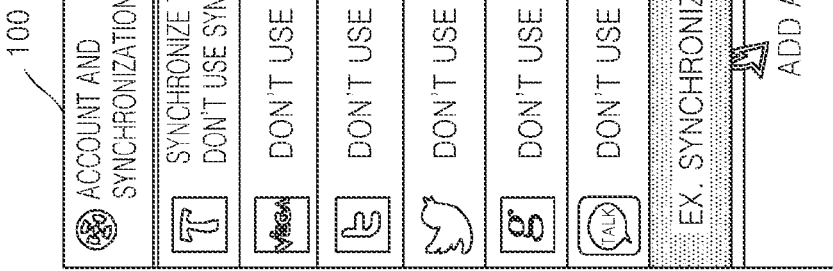
FIGS. 14A through 14C are diagrams of a UI of a host device for receiving a selection from a user with respect to a type of measurement information to be transmitted to a management server, according to an exemplary embodiment.
Figure 14A:
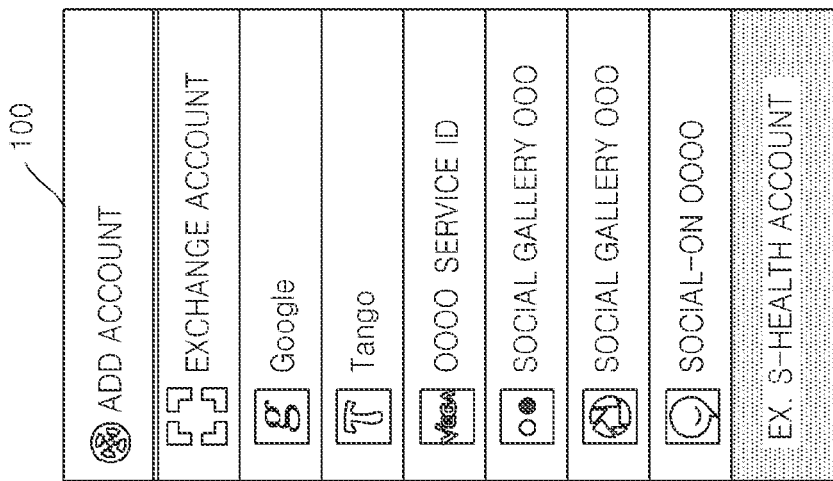
Figure 14C:
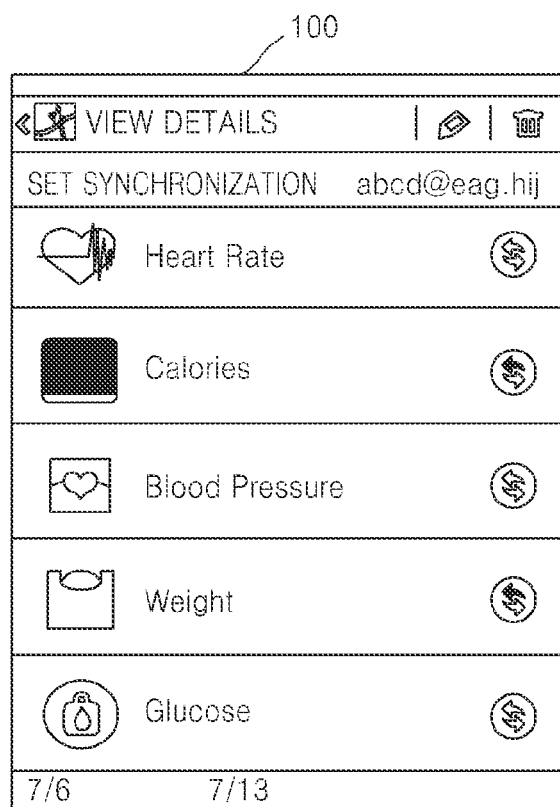

FIG. 14A through 14C are diagrams of a UI of the host device 100 for receiving a selection from a user with respect to a type of measurement information to be transmitted to the management server 300, according to an exemplary embodiment.

As shown in FIG. 14A, the host device 100 may add a management server account according to a user request. Then, as shown in FIG. 14B, the host device 100 may determine whether to synchronize the management server account. In other words, the host device 100 may automatically transmit the measurement information of the external device 200 to the management server 300 by using the management server account. The host device 100 may upload the measurement information at regular cycles, or may upload the measurement information to the management server 300 when the measurement information is obtained.

As shown in FIG. 14C, the host device 100 may provide a setting window for setting a type of measurement information to be transmitted to the management server 300 through a predetermined application. Here, the user may select a synchronization parameter to be transmitted to the management server 300 through the setting window. For example, the user may select blood pressure and a weight as synchronization parameters to be transmitted to the management server 300. Here, from among the measurement information, the host device 100 may transmit blood pressure and a weight to the management server 300 and may not transmit a heart rate to the management server 300.

Figure 15:
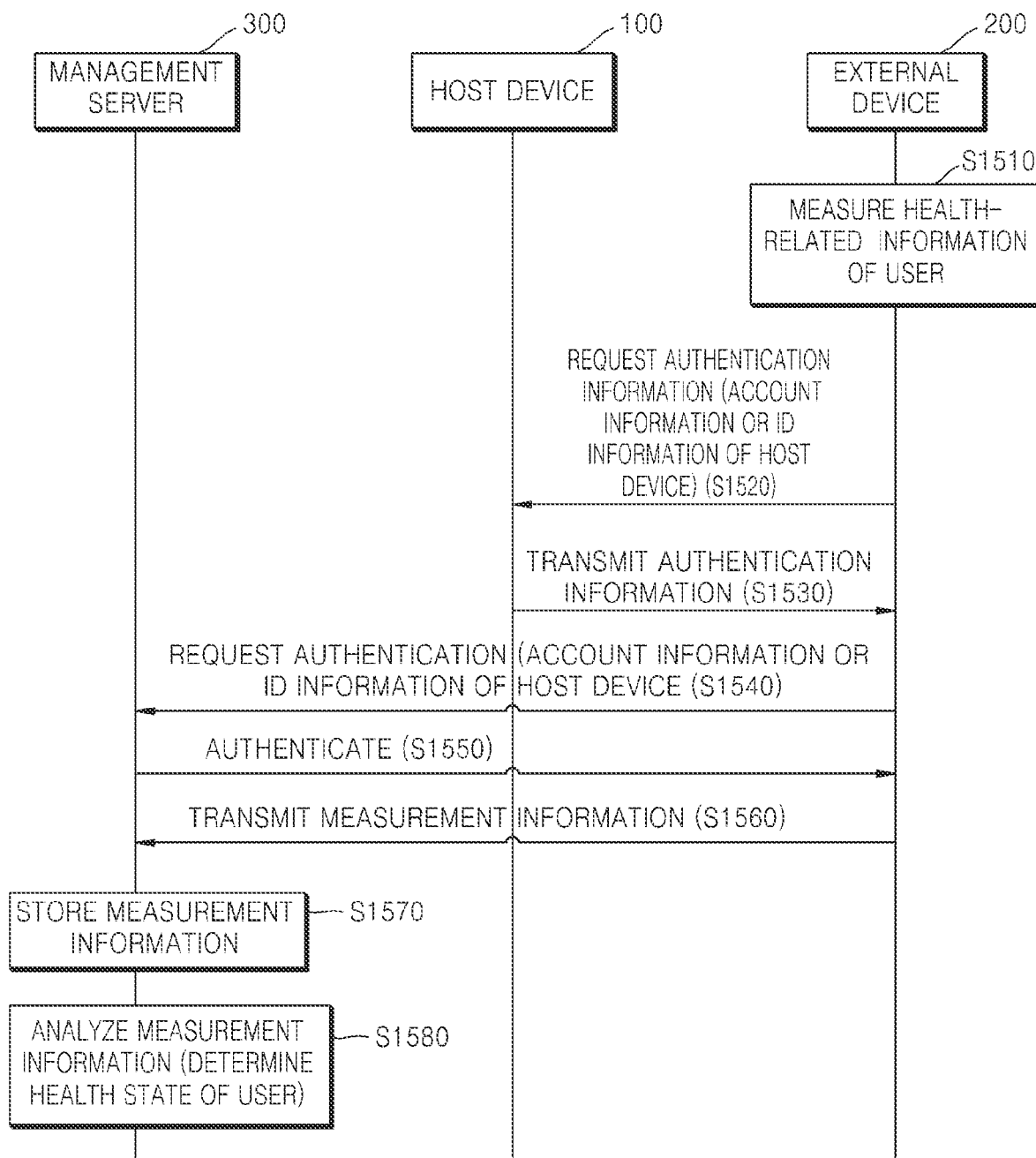
FIG. 15 is a flowchart illustrating a method of an external device directly transmitting measurement information to a management server, according to an exemplary embodiment.

FIG. 15 is a flowchart illustrating a method of the external device 200 directly transmitting measurement information to the management server 300, according to an exemplary embodiment.

In operation S1510, the external device 200 may measure health-related information of a user. Also, the external device 200 may measure surrounding environment information or remaining state information of consumables (such as a blood sugar strips) or medicines (such as insulin).

In operation S1520, the external device 200 may request authentication information from the host device 100 so as to directly communicate with the management server 300. In response to the request, the host device 100 may transmit the authentication information to the external device 200 in operation S1530. For example, the host device 100 may transmit at least one of account information (for example, an ID and a password) and ID information (for example, a device ID) of the host device 100 to the external device 200, as the authentication information.

In operation S1540, the external device 200 may request that the host device be authenticated by the management server 300 while transmitting the authentication information (for example, the account information or the ID information of the host device 100) obtained from the host device 100 to the management server 300.

In operation S1550, in response to the request for authentication, the management server 300 may perform authentication on at least one of the account information and the ID information of the host device 100. For example, the management server 300 may compare the account information or the ID information received from the external device 200 with pre-registered information to perform the authentication.

In operation S1560, when the authentication succeeds, the external device 200 may transmit the measurement information to the management server 300. According to an embodiment, the external device 200 may request that the host device be authenticated by the management server 300 whenever the measurement information is transmitted to the management server 300. Alternatively, the external device 200 may transmit the measurement information to the management server 300 several times based on a single authentication while the external device 200 and the management server 300 are maintained to be connected to each other.

In operation S1570, the management server 300 may store the measurement information. Here, the measurement server 300 may classify and store the measurement information according to the external devices 200, according to account information, or according to the host device 100 to which the external device 200 is connected.

In operation S1580, the management server 300 may analyze the measurement information and determine a health state of the user.

Figure 16:
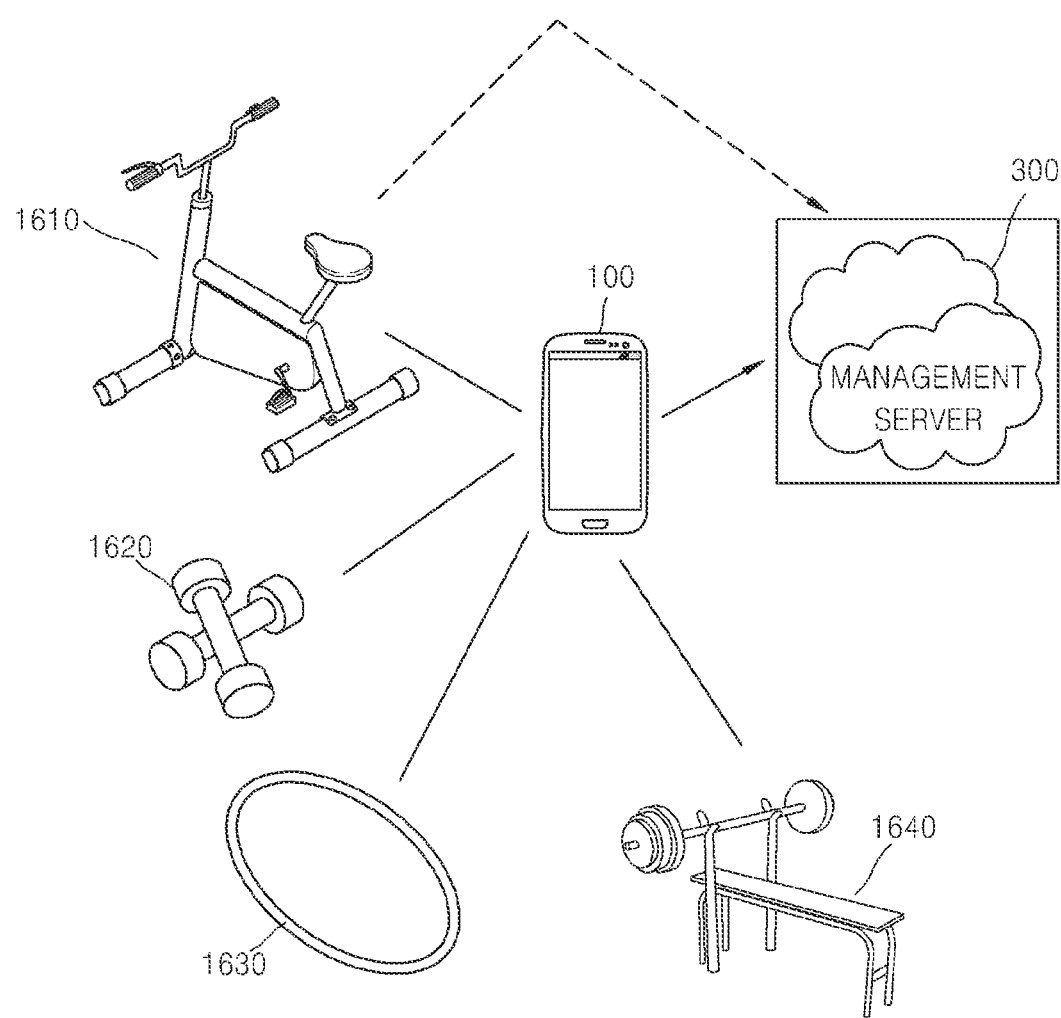
FIG. 16 is a diagram for describing a management server collecting exercise information of a user, according to an exemplary embodiment.

FIG. 16 is a diagram for describing the management server 300 collecting exercise information of a user, according to an exemplary embodiment.

As shown in FIG. 16, exercise information measured in a bicycle 1610, a dumb-bell 1620, a hula hoop 1630, and a bench press 1640 may be transmitted to the management server 300 through the host device 100, or directly to the management server 300. The bicycle 1610, the dumb-bell 1620, the hula hoop 1630, and the bench press 1640 may each include a sensing unit for measuring exercise information and a communication unit for communicating with the host device 100 or the management server 300. For example, the bicycle 1610, the dumb-bell 1620, the hula hoop 1630, and the bench press 1640 may each include a motion sensor, an acceleration sensor, an NFC tag, or a BLE tag, but are not limited thereto.

FIGS. 17A through 17C are diagrams for describing the management server 300 collecting meal information of a user, according to an exemplary embodiment.

As shown in FIG. 17A, when the user tags a personal device 1720 (for example, an employee ID, a student ID, or a mobile phone) to a kiosk 1710 in a restaurant, the personal device 1720 may obtain diet information from the kiosk 1710, and transmit the obtained diet information to the management server 300. Here, the personal device 1720 may transmit the diet information to the management server 300 directly or through the host device 100. The personal device 1720 may transmit the diet information to the management server 300, together with account information. The management server 300 manages a diet and a meal portion of the user through the account information.

As shown in FIG. 17B, the host device 100 obtains the diet information from the personal device 1720 or the management server 300, and may output the obtained diet information on a screen. Alternatively, the management server 300 may obtain the diet information directly from the kiosk 1710.

Figure 18:
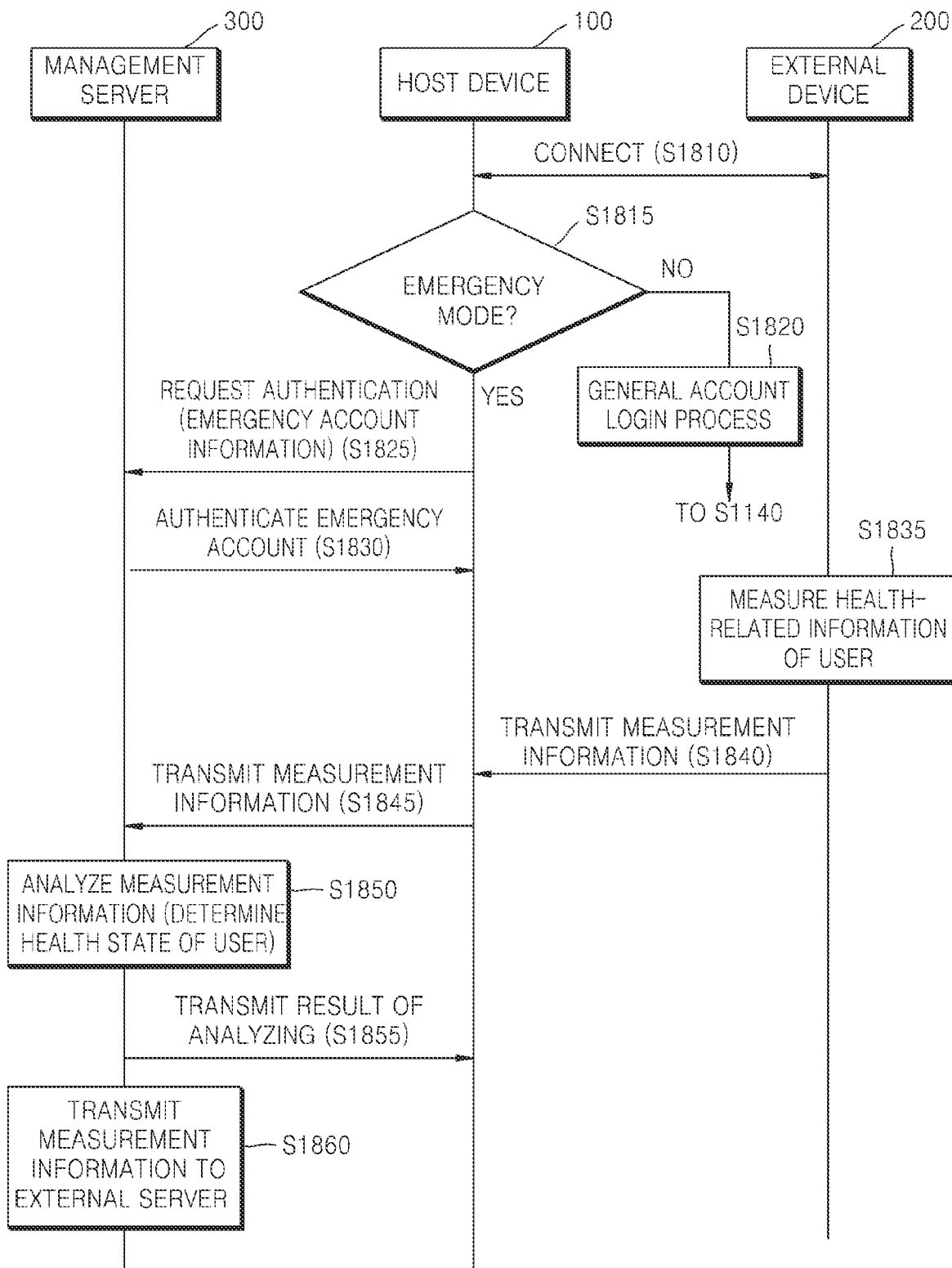
FIG. 18 is a flowchart illustrating a method of a host device transmitting measurement information to a management server in an emergency, according to an exemplary embodiment.

FIG. 18 is a flowchart illustrating a method of the host device 100 transmitting measurement information to the management server 300 in an emergency, according to an exemplary embodiment.

In operation S1810, the host device 100 may detect a physical connection to the external device 200. Here, in operation S1815, the host device 100 may determine whether a current mode is an emergency mode. According to an embodiment, the emergency mode may be activated via an input of a user of the external device 200 or via remote control.

In operation S1820, when the current mode is not an emergency mode, the host device 100 may perform a general account login process. In operation S1825, when the current mode is an emergency mode, the host device 100 may request to be authenticated by the management server 300 by using emergency account information. An emergency account may be operated separately from a personal account. In operation S1830, the management server 300 may perform authentication on the emergency account information.

In operation S1835, the external device 200 may measure health-related information of the user. Then, in operation S1840, the external device 200 may transmit measurement information to the host device 100.

In operation S1845, the host device 100 may transmit the measurement information obtained from the external device 200 to the management server 300 through the emergency account. The management server 300 may analyze the measurement information in operation S1850, and the management server 300 may transmit a result of the analyzing to the host device 100 in operation S1855. Then, the host device may display the result on a screen. Examples of the result may include current state information of the user, information for dealing with an emergency, and a type of measurement information that is additionally required.

In operation S1860, the management server 300 may transmit the measurement information to an external server, for example, a medical institute server, and obtain diagnosis/prescription information from the external server. Then, the management server 300 may transmit the diagnosis/prescription information to the host device 100. In an emergency, the host device 100 may transmit health information measured by another user using the external device 200 to the management server 300 or a medical institute server by using emergency account information, and receive suitable feedback from the management server 300 or the medical institute server.

According to an embodiment, an order of operations S1810 through S1860 may be changed, or some operations may be omitted.

Figure 19:
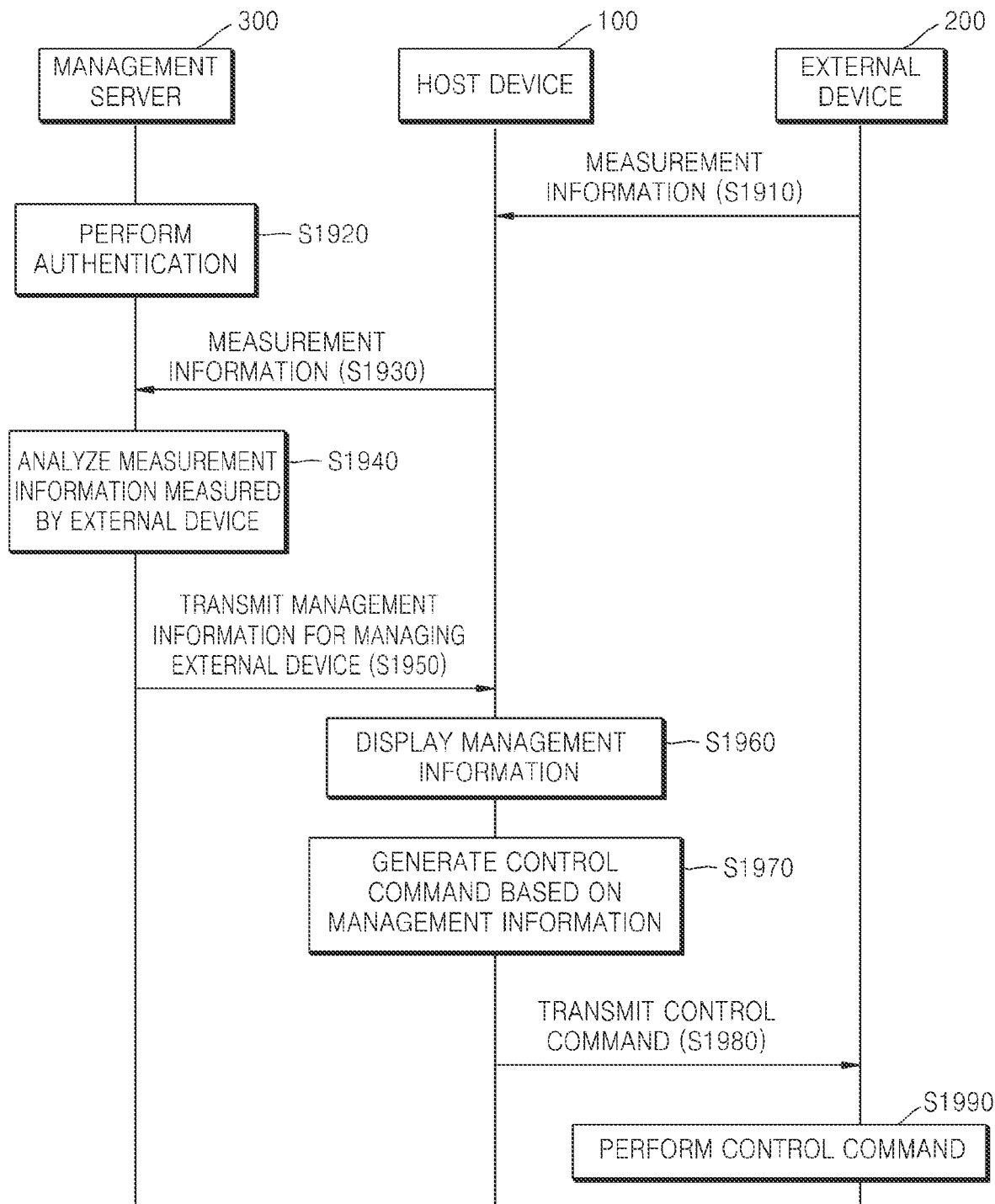
FIG. 19 is a flowchart illustrating a method of a host device generating a control command for controlling an external device, according to an exemplary embodiment.

FIG. 19 is a flowchart illustrating a method of the host device 100 generating a control command for controlling the external device 200, according to an exemplary embodiment.

In operation S1910, the host device 100 may obtain measurement information from the external device 200. In operation S1920, the management server 300 may authenticate the host device 100. If the authentication succeeds, the host device 100 may transmit the measurement information obtained from the external device 200 to the management server 300 in operation S1930. Since operations S1910 through S1930 correspond to operations S1110 through S1130 of FIG. 11, details thereof will not be repeated here.

In operation S1940, the management server 300 may analyze the measurement information measured by the external device 200. According to an embodiment, the management server 300 may analyze a current health state of the user by comparing the measurement information measured by the external device 200 and pre-stored health information, such as a PHR.

Alternatively, the management server 300 may determine a health state of the user by comparing measurement information of other users having a similar disease and the measurement information measured by the external device 200.

The management server 300 may transmit the measurement information to an external server, such as a medical institute server, and receive diagnosis/prescription information corresponding to the measurement information to analyze the health state of the user.

For example, the management server 300 may determine the health state of the user by analyzing measurement information, such as blood pressure or blood sugar, obtained through the external device 200, such as a blood pressure gauge or a blood sugar meter. Alternatively, the management server 300 may calculate a suitable exercise amount for the user in association with an EMR, and compare the calculated suitable exercise amount with an actual exercise amount measured by a sporting apparatus. Here, the management server 300 may analyze whether the actual exercise amount is insufficient or excessive based on a result of the comparison.

The management server 300 may analyze environment information (for example, a temperature or humidity) measured by the external device 200 including an environment sensor, or may determine a replace cycle of a strip of a blood sugar meter or medical consumables like insulin. Also, the management server 300 may analyze and manage administration information of the user, or analyze program version information of the external device 200. Meanwhile, the management server 300 may search for exercise recommendation information or food recommendation information from an external server, by using the measurement information.

In operation S1950, the management server 300 may transmit management information for managing the external device 200 to the host device 100. For example, the management server 300 may transmit at least one of diagnosis information, prescription information, food recommendation information, exercise recommendation information, environment setting information, alarm information, and update information for updating the at least one external device 200, which are generated based on the measurement information, to the host device 100.

In operation S1960, the host device 100 may display the management information received from the management server 300 on a screen. For example, the host device 100 may display diagnosis information, prescription information, food recommendation information, exercise recommendation information, environment setting information, consumables replacement information, or firmware update information on the screen. Alternatively, the host device 100 may output a warning or an alarm about medicine administration.

The host device 100 may manage the at least one external device 200 based on the management information.

For example, in operation S1970, the host device 100 may generate a control command for controlling the external device 200 based on the management information. Here, the host device 100 may convert the control command according to a control protocol of the at least one external device 200.

In operation S1980, the host device 100 may transmit the control command to the external device 200. For example, the host device 100 may transmit a control command enabling the at least one external device 200 to output at least one of an alarm, a warning, and recommendation information. Alternatively, the host device 100 may transmit a control command enabling the at least one external device 200 to change a setting value, or enabling the at least one external device 200 to update a program installed therein.

In operation S1990, the external device 200 may perform the control command received from the host device 100.

Figure 20:
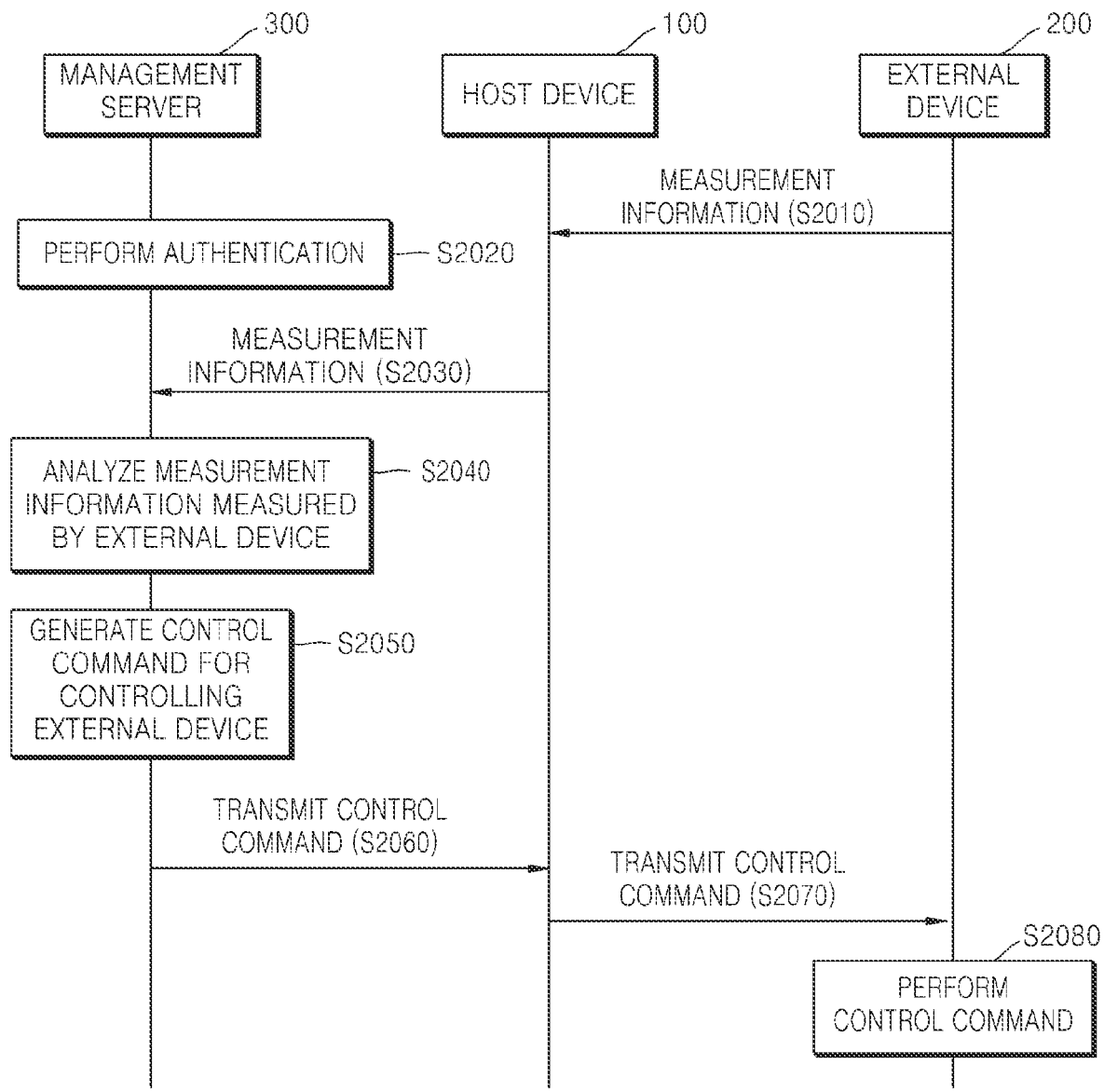
FIG. 20 is a flowchart illustrating a method of a management server transmitting a control command for controlling an external device to the external device through a host device, according to an exemplary embodiment.

FIG. 20 is a flowchart illustrating a method of the management server 300 transmitting a control command for controlling the external device 200 to the external device 200 through the host device 100, according to an exemplary embodiment. Unlike the method of FIG. 19, the management server 300 may directly generate a control command for controlling the external device 200 in the method of FIG. 20.

In operation S2010, the host device 100 may receive measurement information from the external device 200. In operation S2020, the measurement server 300 may authenticate the host device 100. In operation S2030, the measurement server 300 may receive the measurement information measured by the external device 200 from the authenticated host device 100. In operation S2040, the host device 100 may analyze the measurement information measured by the external device 200. Since operations S2010 through S2040 correspond to operations S1910 through S1920 of FIG. 19, details thereof will not be repeated here.

In operation S2050, the management server 300 may directly generate a control command for controlling the external device 200 based on the measurement information measured by the external device 200.

For example, if blood sugar or blood pressure that is usually periodically measured is not measured, the management server 300 may generate a control command for the external device 200 or the host device 100 to output an alarm. Alternatively, if the user eats food that generates an allergic reaction, the management server 300 may generate a control command for the external device 200 or the host device 100 to output a warning message. Alternatively, the management server 300 may generate a control command for the external device 200 or the host device 100 to output exercise recommendation information or a diet menu based on daily exercise information or daily meal information of the user.

According to an embodiment, the management server 300 may generate a control command for the at least one external device 200 to change a setting value or to update a program installed in the at least one external device 200.

If consumables used by the external device 200 are insufficient, the management server 300 may automatically order consumables from a sales server selling the consumables, or may generate a control command for the external device 200 to output a warning message about the insufficiency of consumables.

In operation S2060, the management server 300 may transmit the control command to the host device 100. Here, the management server 300 may change the control command according to a control protocol of the at least one external device 200, and transmit the changed control command to the host device 100.

In operation S2070, the host device 100 may transmit the control command received from the management server 300 to the external device 200. Here, the host device 100 may change the received control command according to the control protocol of the at least one external device 200, and transmit the changed control command to the external device 200.

In operation S2080, the external device 200 may perform the control command received from the host device 100.

Figure 21:
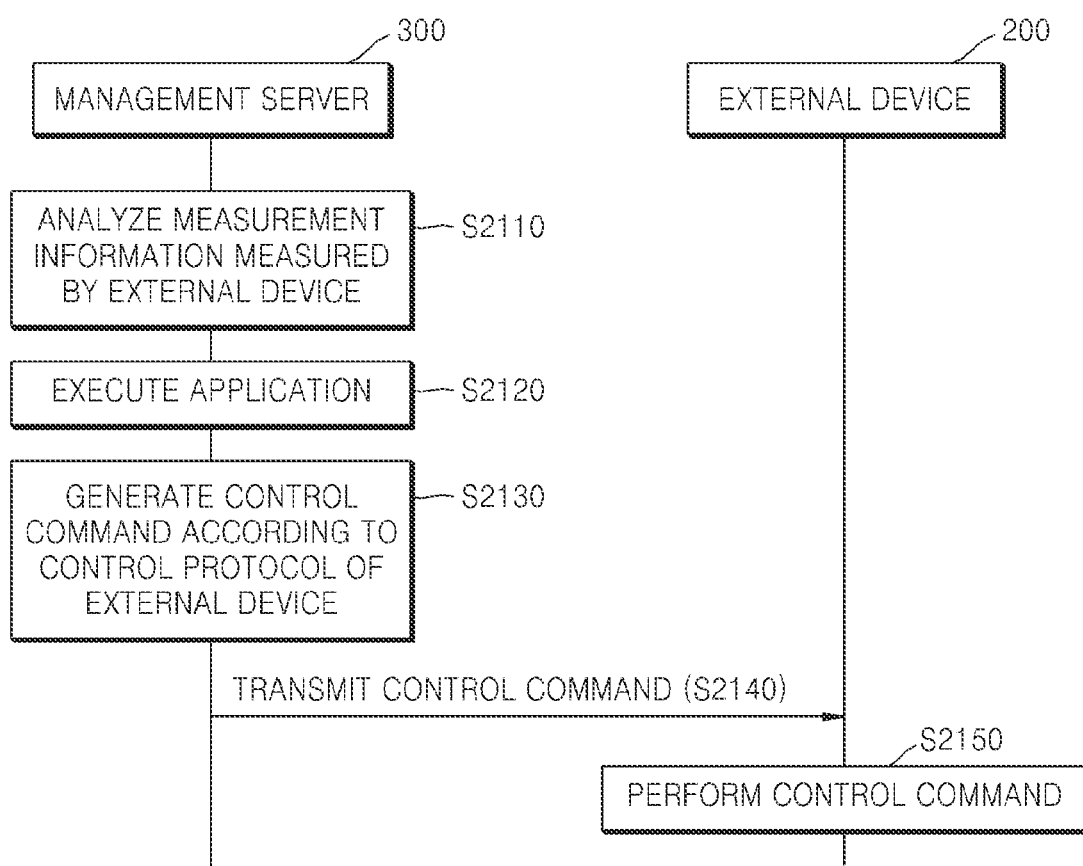
FIG. 21 is a flowchart illustrating a method of a management server directly controlling an external device, according to an exemplary embodiment.

FIG. 21 is a flowchart illustrating a method of the management server 300 directly controlling the external device 200, according to an exemplary embodiment.

In operation S2110, the management server 300 may analyze measurement information measured by the external device 200. Since operation S2110 corresponds to operation S1940 of FIG. 19, details thereof will not be repeated here.

In operation S2120, the management server 300 may execute an application related to the external device 200. By executing the application related to the external device 200, the management server 300 may form a communication session capable of directly communicating with the external device 200 without having to use the host device 100.

In operation S2130, the management server 300 may generate a control command according to a control protocol of the external device 200. In other words, the management server 300 may change the control command generated based on a result of analyzing the measurement information, according to the control protocol of the external device 200.

In operation S2140, the management server 300 may directly transmit the control command to the external device 200 without having to use the host device 100. The management server 300 may transmit the control command to the external device 200 through a wired or wireless network.

In operation S2150, the external device 200 may perform the control command received from the management server 300.

Figure 22:
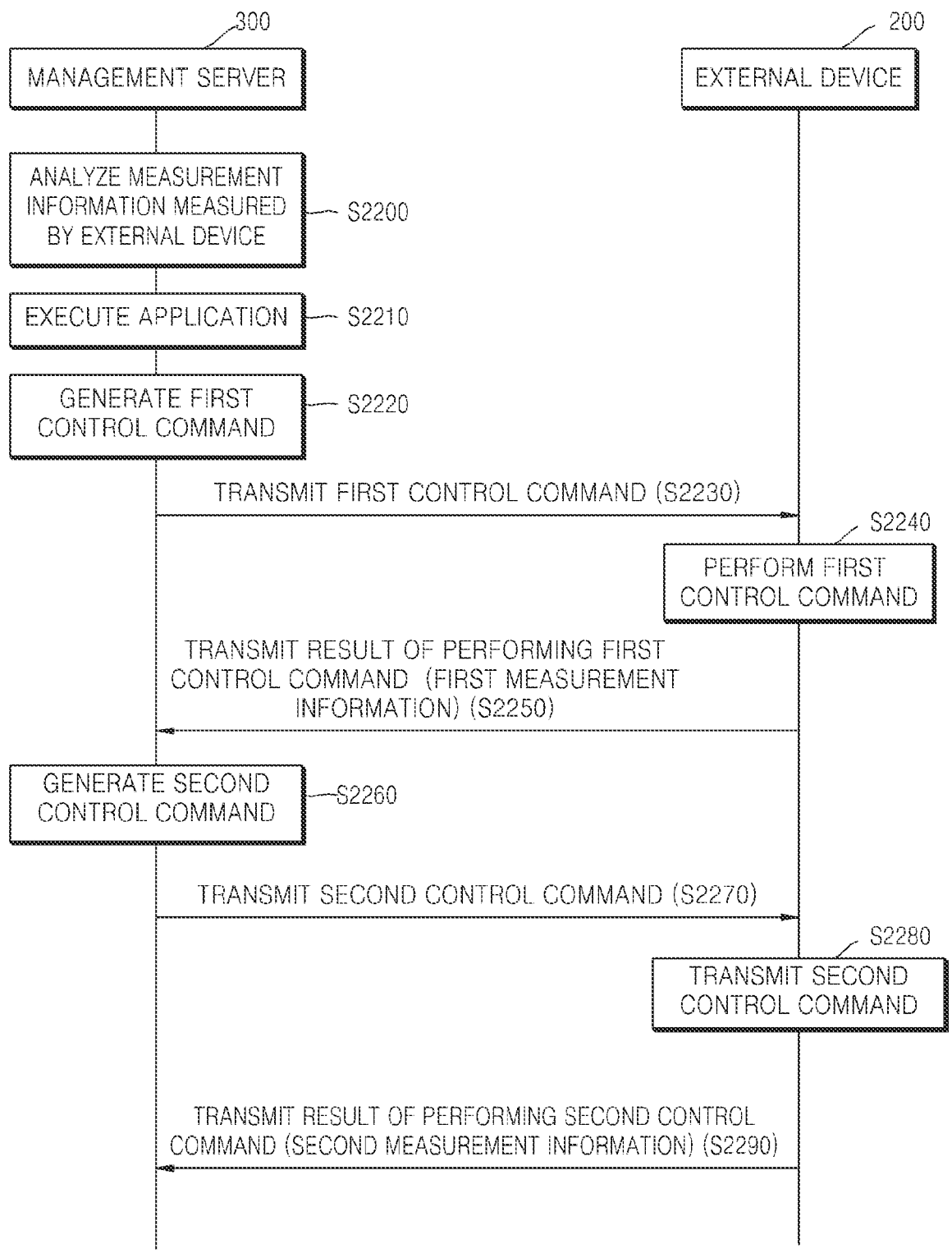
FIG. 22 is a flowchart illustrating a method of transmitting a control command to an external device by stages, according to an exemplary embodiment.

FIG. 22 is a flowchart illustrating a method of transmitting a control command to the external device 200 by stages, according to an exemplary embodiment.

In operation S2200, the management server 300 may analyze measurement information measured by the external device 200. Then, in operation S2210, the management server 300 may execute an application related to the external device 200 to form a communication session capable of communicating with the external device 200.

In operation S2220, the management server 300 may generate a first control command based on a result of analyzing the measurement information. In operation S2230, the management server 300 may transmit the first control command. For example, if the external device 200 does not transmit weight measurement information at certain intervals, the management server 300 may transmit the first control command to the external device 200 to transmit the weight measurement information.

In operation S2240, the external device 200 may perform the first control command. Then, in operation S2250, the external device 200 may transmit a result of performing the first control command, for example first measurement information. For example, if the weight measurement information of the user is stored, the external device 200 may transmit the weight measurement information to the management server 300. Alternatively, if the user has not yet measured the weight, the external device 200 may output an alarm for the user to measure the weight. Here, if the user measures the weight by using an external device, such as a scale, the scale may transmit the weight measurement information (first measurement information) to the management server 300.

In operation S2260, the management server 300 may generate a second control command based on the result of performing the first control command received from the external device 200. For example, if the current weight of the user is remarkably increased compared to the weight measured a week before based on analyzing the result of performing the first control command, the management server 300 may generate the second control command requesting the external device 200 to analyze body composition, such as a body fat percentage, a body mass index, an abdominal fat percentage, muscle distribution, or basic metabolic rate).

Alternatively, when the current weight of the user is similar to the weight measured a week before based on analyzing the result of performing the first control command, the management server 300 may not generate the second control command.

In operation S2270, the management server 300 may transmit the second control command to the external device 200. In operation S2280, the external device 200 may additionally perform the second control command. In operation S2290, the external device 200 may transmit a result of performing the second control command to the management server 300. For example, the external device 200 may transmit a result of analyzing the body composition (second measurement information) to the management server 300.

Figure 23:
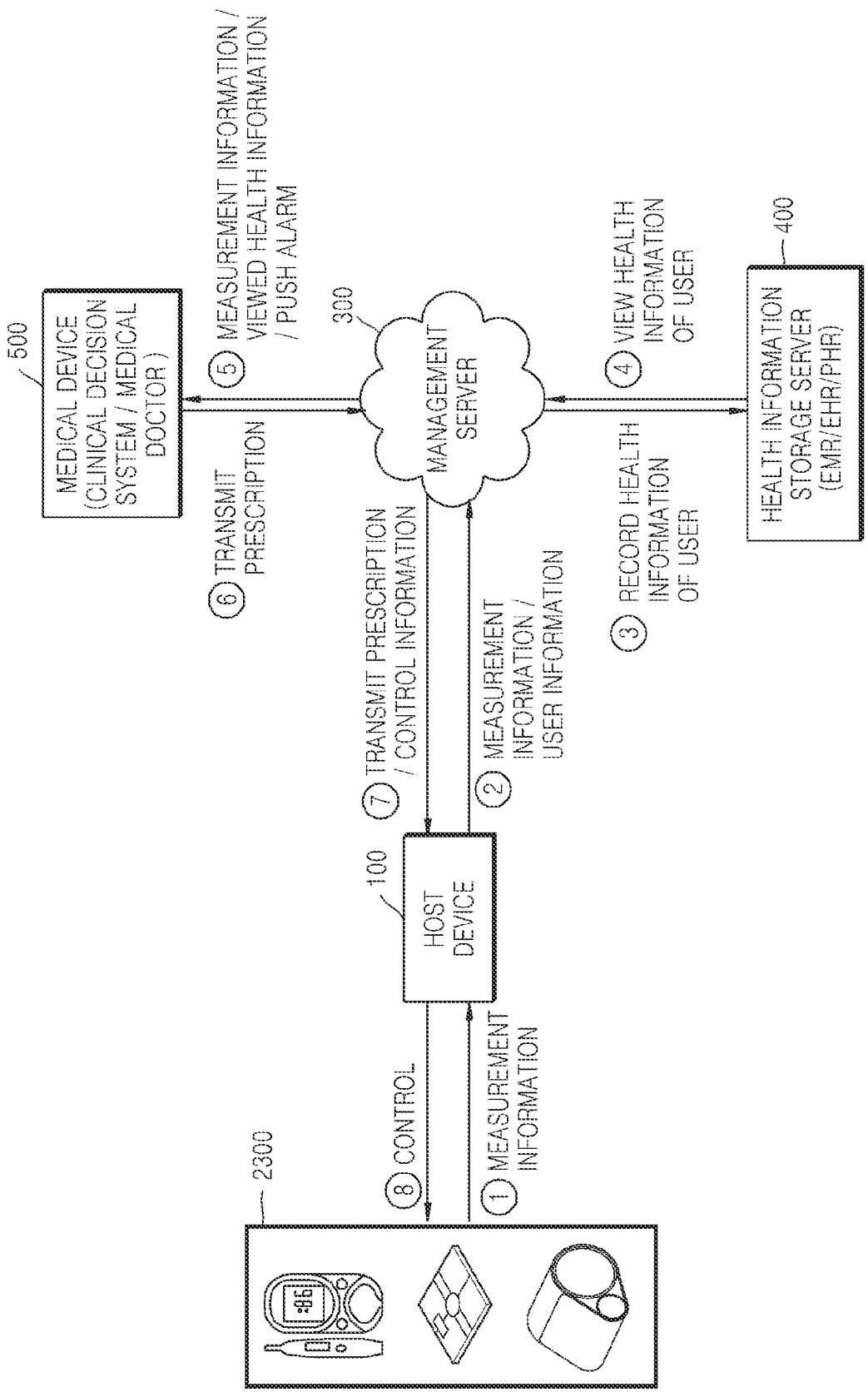
FIG. 23 is a diagram for describing a method of a management server providing prescription or diagnosis information about a user by using measurement information, according to an exemplary embodiment.

FIG. 23 is a diagram for describing a method of the management server 300 providing prescription or diagnosis information about a user by using measurement information, according to an exemplary embodiment. The host device 100 mentioned hereinafter may be a device authenticated by the management server 300.

As shown in FIG. 3, an external device 2300 for measuring health information, such as a blood sugar meter, a blood pressure gauge, or a scale, may transmit measurement information, such as blood sugar, blood pressure, or a weight, to the host device 100 in operation ①. Here, the host device 100 may transmit the received measurement information to the management server 300 in operation ②.

The management server 300 may store the measurement information in a health information storage server 400 in operation ③. The health information storage server 400 may be a storage unit of the management server 300, or as a separate server. Examples of the health information storage server 400 include an EMR server, an EHR server, or a PHR server.

The management server 300 may view health information of the user stored in the health information storage server 400 in operation ④. The health information storage server 400 may classify and store the measurement information according to accounts, according to external devices 200, or according to host devices 100.

The management server 300 may transmit the measurement information measured by the external device 2300 and/or health information obtained from the health information storage server 400 to a medical device 500 in operation ⑤. Also, if it is determined that the user has a health problem based on analyzing the measurement obtained from the external device 2300, the management server 300 may transmit a push alarm to the medical device 500.

The medical device 500 may include at least one of a medical institute server, a doctor's device, and a pharmacist's device, but is not limited thereto. The medical device 500 may analyze the received measurement information and the health information of the user, and transmit prescription information corresponding to the measurement information to the management server 300 in operation ⑥.

The management server 300 may transmit the prescription information to the host device 100 in operation ⑦. Here, the host device 100 may output the prescription information on a screen. The user may check the prescription information through the host device 100.

Also, the management server 300 may transmit control information for controlling the external device 2300 to the host device 100, based on the prescription information. Here, the host device 100 may generate a control command based on the control information, and transmit the generated control command to the external device 2300 in operation ⑧.

According to an embodiment, the medical device 500 connected to the management server 300 may remotely prescribe a medicine or diagnose a patient. Also, the user is able to check a feedback of the medical device 500 about the measurement information measured by the external device 2300 through the external device 2300 or the host device 100.

Figure 24:
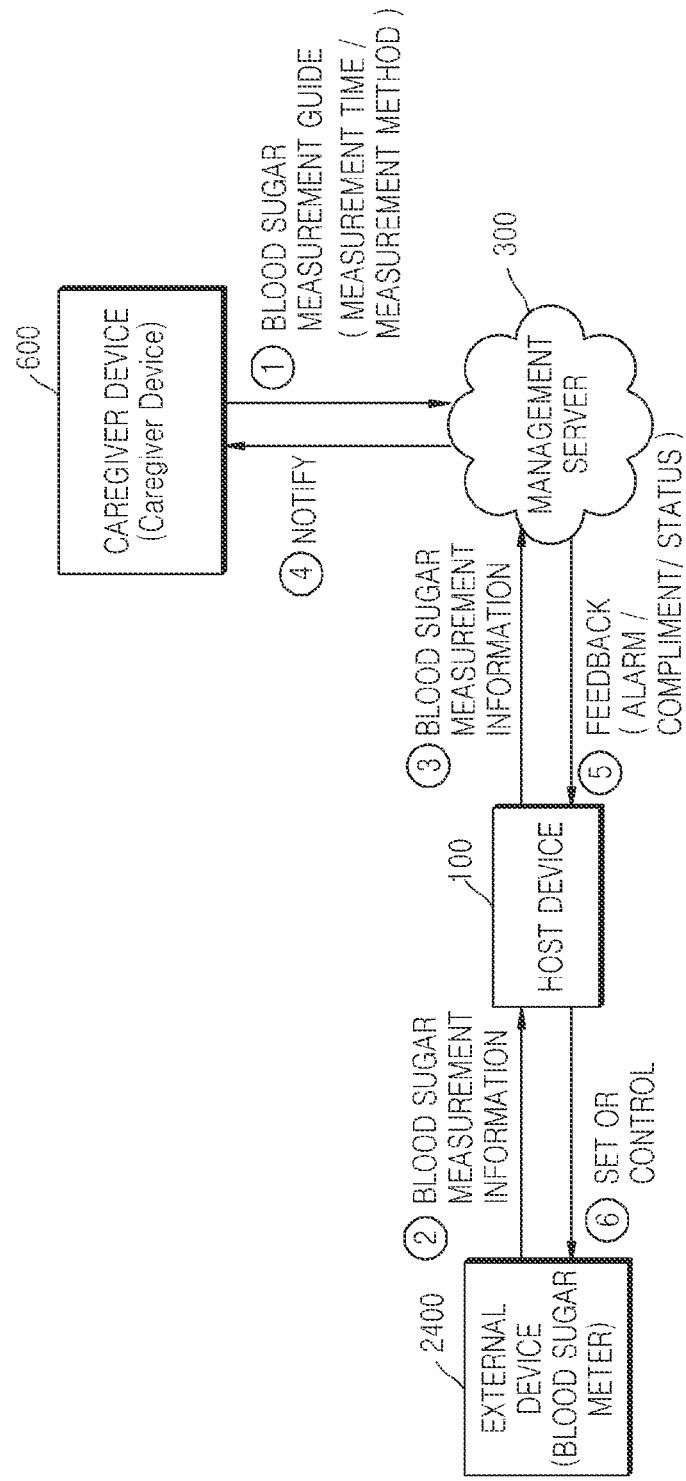
FIG. 24 is a diagram for describing a method of a management server controlling an external device (a blood sugar meter) by using blood sugar measurement information, according to an exemplary embodiment.

FIG. 24 is a diagram for describing a method of the management server 300 controlling an external device 2400 (a blood sugar meter) by using blood sugar measurement information, according to an exemplary embodiment.

The management server 300 may receive blood sugar measurement guide information from a caregiver device 600. For example, the management server 300 may receive information recommending to measure blood sugar three times a day from the caregiver device 600.

The management server 300 may receive blood sugar measurement information measured by the external device 2400 through the host device 100. Here, the blood sugar measurement information may include a blood sugar level and a blood sugar measurement time. The management server 300 may compare actual blood sugar measurement information (for example, once a day) and the blood sugar measurement guide information (for example, three times a day). If measurement schedules do not match, the management server 300 may provide an alarm to the caregiver device 600 or the host device 100 about a blood sugar measurement schedule. At this time, a caregiver may call the user to describe his or her blood sugar measurement cycles.

Also, the host device 100 may output alarm information received from the management server 300 or control the external device 2400 based on the alarm information. For example, the host device 100 may control the external device 2400 to output a warning message related to a measurement schedule.

If a setting value of the external device 2400 is wrongly set, the management server 300 may change the setting value through the host device 100.

According to another embodiment, the management server 300 may transmit the blood sugar measurement guide information to the host device 100, and the host device 100 may compare the blood sugar measurement guide information with the measurement information measured by the external device 2400. According to an embodiment, the host device 100 may transmit information about a certain event to the management server 300 when the certain event occurs, for example, when a blood sugar level is a critical level or an actual measurement period does not match a measurement period in measurement guide information. Here, the management server 300 may transmit the information about the certain event to the caregiver device 600, and receive feedback on the certain event from the caregiver device 600. The management server 300 may control the host device 100 or the external device 2400 based on the feedback on the certain event.

Figure 25:
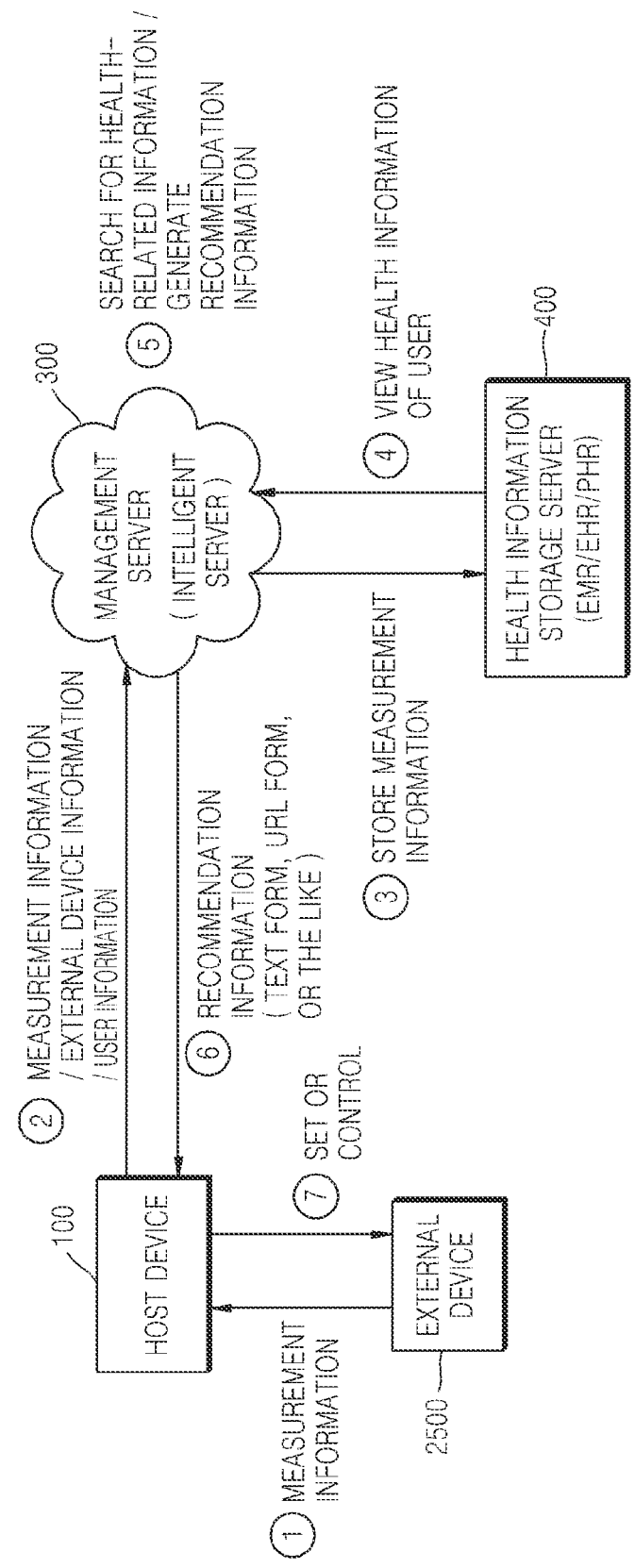
FIG. 25 is a diagram for describing a method of a management server providing recommendation information, according to an exemplary embodiment.

FIG. 25 is a diagram for describing a method of the management server 300 providing recommendation information, according to an exemplary embodiment.

The management server 300 may receive measurement information measured by an external device 2500 through the host device 100 that is authenticated, and then store the received measurement information in the health information storage server 400. Meanwhile, the management server 300 may view health information of a user stored in the health information storage server 400.

The management server 300 may search for health-related information from an external server based on the measurement information measured by the external device 2500 and the health information viewed from the health information storage server 400. Also, the management server 300 may generate recommendation information, for example, food recommendation information, exercise recommendation information, temperature recommendation information, or humidity recommendation information, based on a result of the searching.

Here, the management server 300 may transmit the recommendation information to the host device 100. The recommendation information transmitted by the management server 300 may be realized in a text form, an image form, or a uniform resource locator (URL) form. The host device 100 may display the received recommendation information on a screen.

The host device 100 may generate a control command for controlling the external device 2500 based on the received recommendation information. For example, a room temperature and humidity suitable for a health state of the user may be respectively 25° C. and 50%, but if a current temperature and current humidity are respectively 28° C. and 30%, the host device 100 may generate a control command to change setting values of a humidifier and air conditioner.

FIG. 26 is a diagram for describing a method of a management server providing exercise recommendation information, according to an exemplary embodiment.

The management server 300 may collect measurement information such as a weight, a height, a body fat percentage, a heart rate, blood pressure, blood sugar, an exercise amount, and sleep information from first through n-th external devices 2600-1 through 2600-*n*. Here, the management server 300 may receive the measurement information through the host device 100 or directly from the first through n-th external devices 2600-1 through 2600-*n*.

The management server 300 may record the measurement information on the health information storage server 400, and view everyday exercise information or health state information of a user from the health information storage server 400.

The management server 300 may compare the measurement information measured by the first through n-th external devices 2600-1 through 2600-*n* with the everyday exercise information and health state information of the user, and generate suitable (recommended) exercise information, such as an exercise type, an exercise time, a distance, and a course. The management server 300 may transmit the suitable (recommended) exercise information to the host device 100 or the first through n-th external devices 2600-1 through 2600-*n*. Also, if an exercise amount of the user exceeds a suitable level, the management server 300 may transmit a notification message about the exercise amount to the host device 100 or the first through n-th external devices 2600-1 through 2600-*n*.

Hereinafter, it is assumed that a suitable exercise amount is 1400 kcal and a user X wants to gain 3 kg, wherein the user X having cardiac arrhythmia is riding a cycle while wearing a heart rate monitor.

When a current one-day exercise amount of the user X is 1300 kcal, an exercise time is 1 hour, and an average heart rate is 120 bpm upon analyzing measurement information obtained from an external device, such as the cycle or the heart rate monitor, the management server 300 may control the host device 100 or the external device, such as the cycle or the heart rate monitor, to output a notification message notifying the user X that he or she has nearly reached a recommended exercise amount. Also, the management server 300 may provide weight loss information expected if the user X exercises at a current pace to the host device 100 or one of the first through n-th external devices 2600-1 through 2600-*n*.

If a one-day exercise amount of the user X exceeds the recommended exercise amount, the management server 300 may transmit a message notifying the user X that a recommended heart rate, a recommended exercise time, and the recommended exercise amount have been exceeded to the host device 100 or the external device, such as the cycle or the heart rate monitor.

According to another embodiment, when sleep efficiency of a user Y is low, for example, when the user Y did not sleep well, upon analyzing sleep measurement information of the user Y, the management server 300 may recommend the user Y an exercise amount lower than an average suitable exercise amount as a current suitable exercise amount. Also, the management server 300 may provide a suitable exercise type, a time, a distance, a course, and an interval to the host device 100 or the external device 200 before the user Y starts to exercise.

Figure 27B:
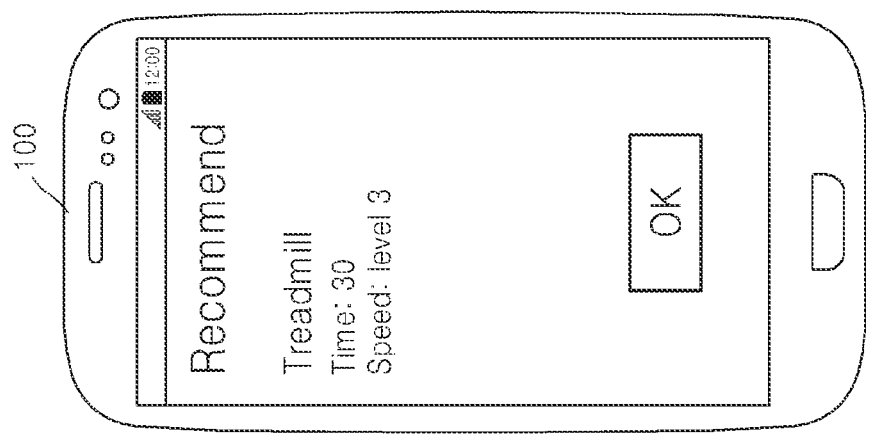
FIGS. 27A and 27B illustrate diagrams of screens of an external device and host device, which display recommendation information, according to an exemplary embodiment.
Figure 27A:
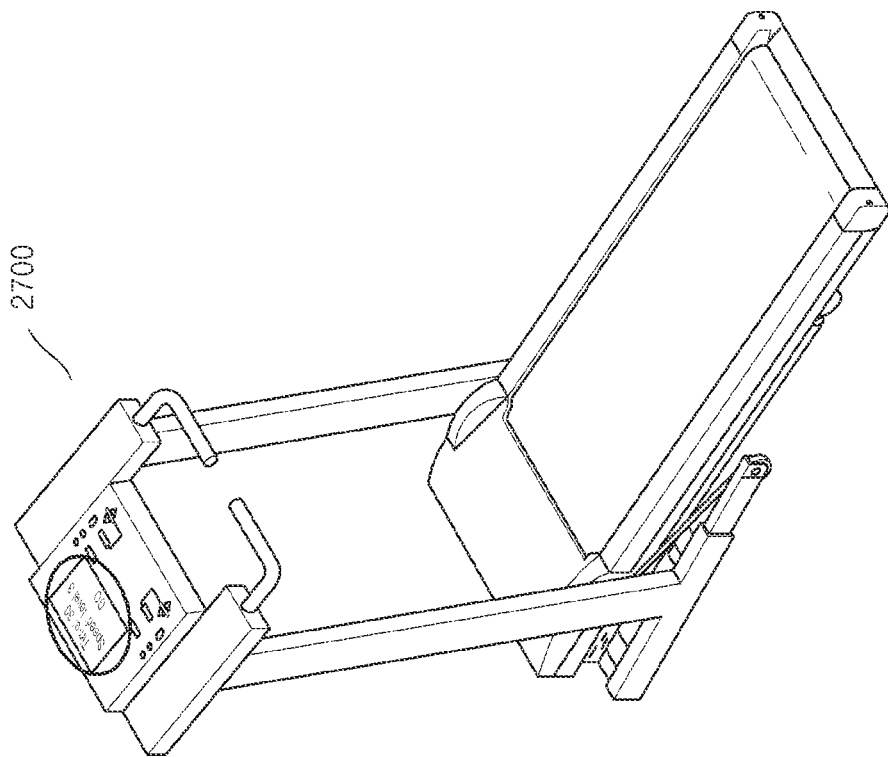

FIGS. 27A and 27B illustrate diagrams of screens of the external device 200 and the host device 100, which display recommendation information, according to an exemplary embodiment. In FIG. 27, the external device 200 is a treadmill 2700.

As shown in FIG. 27A, the treadmill 2700 may display exercise recommendation information according to a control command received from the host device 100 or the management server 300. For example, the treadmill 2700 may display a recommended exercise time to be 30 minutes and a recommended exercise level to be level 3.

The treadmill 2700 may change a pre-set value according to the control command received from the host device 100 or the management server 300. For example, when a user presses a start button in the treadmill 2700, the treadmill 2700 is basically set to start from level 1, but the treadmill 2700 may change a setting value to start from level 3 when the user presses the start button according to the control command received from the host device 100 or the management server 300.

As shown in FIG. 27B, the host device 100 may display exercise recommendation information according to a control command received from the management server 300. For example, the host device 100 may display a recommended exercise type to be a treadmill, a recommended exercise time to be 30 minutes, and a recommended exercise level to be level 3.

Meanwhile, the host device 100 may transmit the control command received from the management server 300 to the treadmill 2700. The host device 100 may control the treadmill 2700 based on the exercise recommendation information received from the management server 300. Here, the host device 100 may control the treadmill 2700 by executing an application related to the treadmill 2700.

Figure 28:
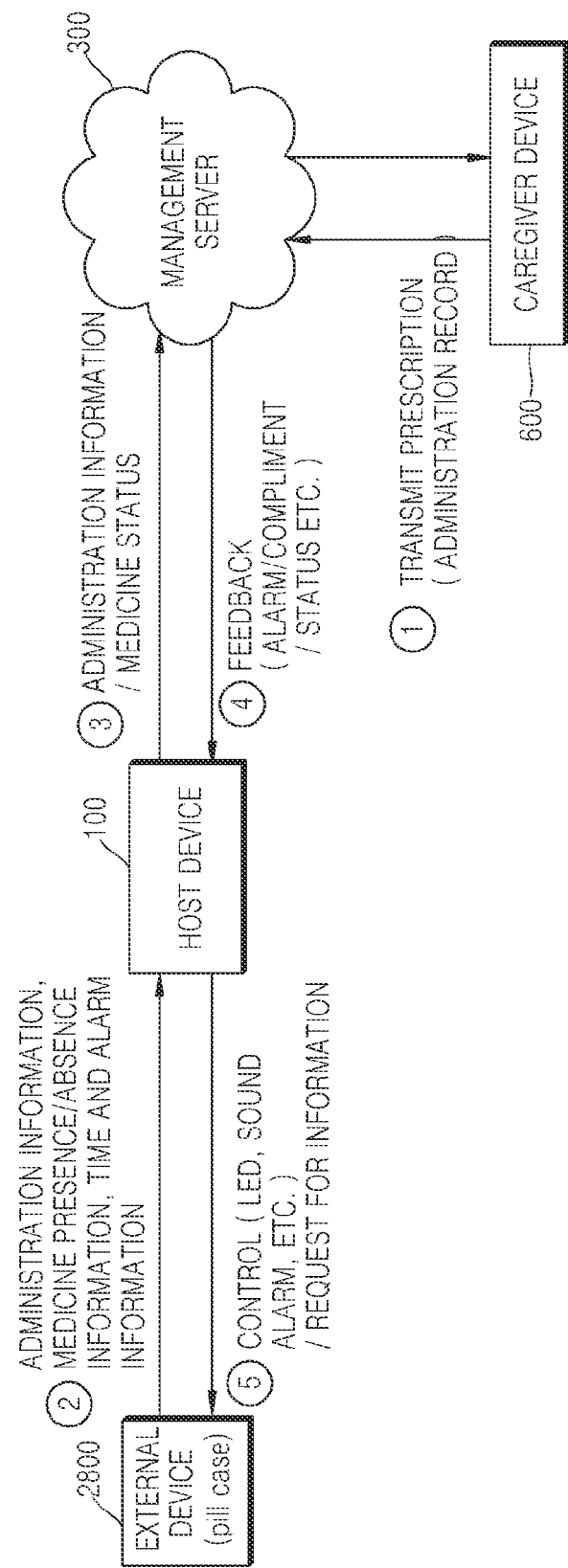
FIG. 28 is a diagram for describing a method of a management server controlling an external device (a pill case) based on administration information, according to an exemplary embodiment.

FIG. 28 is a diagram for describing a method of the management server 300 controlling an external device (a pill case) 2800 based on administration information, according to an exemplary embodiment. In FIG. 28, the external device 200 is the pill case 2800.

The pill case 2800 may measure administration information, such as an administration time and an administered medicine type, and medicine presence/absence information. For example, when the pill case 2800 is divided into spaces corresponding to a week and morning/noon/evening, and a medicine to be administered by a user is disposed in each space, the pill case 2800 may check whether the user administered the medicine and an administered time, based on the medicine presence/absence information of each space.

The pill case 2800 may receive alarm information. For example, when the user has to administer a medicine at 7:00, 13:00, and 19:00, the user may set the pill case 2800 to generate an alarm at the corresponding time.

The pill case 2800 may transmit the administration information, the medicine presence/absence information, and the alarm information to the host device 100, and the host device 100 may transmit the received administration information, the received medicine presence/absence information, and the received alarm information to the management server 300. According to another embodiment, the user may input alarm information to the host device 100 so that the pill case 2800 generates an alarm.

The management server 300 may compare prescription information obtained from the caregiver device 600 and the administration information measured by the pill case 2800. Also, the management server 300 may transmit feedback, such as an alarm, a compliment, a warning, or an administration status, to the host device 100, according to a result of the comparing.

The host device 100 may control the pill case 2800 based on the feedback from the management server 300. For example, the host device 100 may control an output unit, such as a light-emitting diode (LED), a sound output unit, or a display unit, of the pill case 2800.

The management server 300 may provide information about a prescribed medicine, a medicine that should not be administered together, food which the user is to be cautious about, and drugstores where the user may buy a medicine (a drugstore name, location, and business hours), to the host device 100 or the pill case 2800, based on the prescription information.

Also, the management server 300 may adjust an administration time in connection with meal information of the user, such as a meal time or a meal portion, and notify the adjusted administration time to the host device 100 or the pill case 2800. If a time zone of the pill case 2800 is changed as the user travels, the management server 300 may adjust a pre-set administration time by recognizing a situation.

Figure 29A:
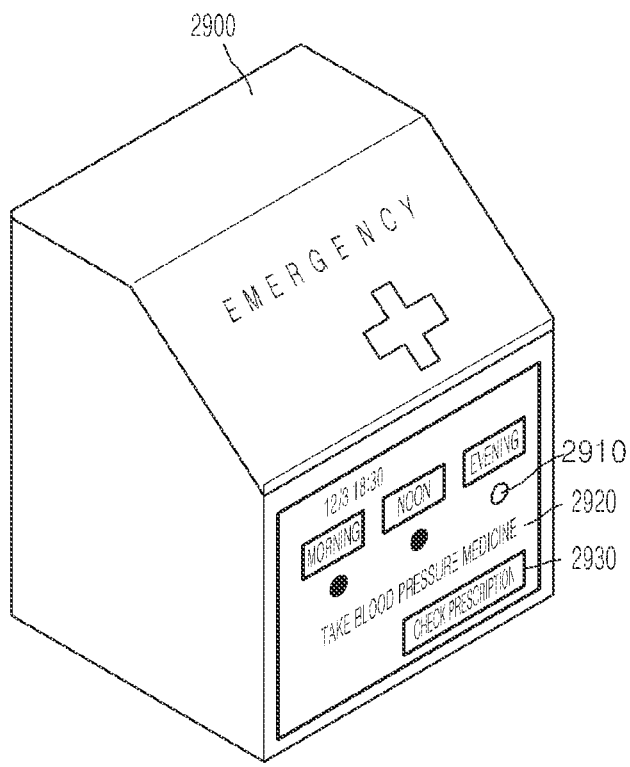
FIGS. 29A and 29B are diagrams of screens of an external device (a pill case) and host device, respectively, which display alarm information, according to an exemplary embodiment.
Figure 29B:
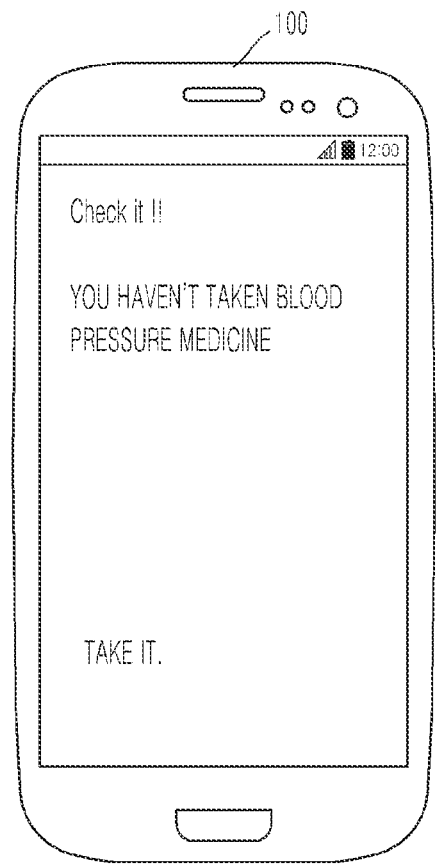

FIGS. 29A and 29B are diagrams of screens of an external device (a pill case) 2900 and the host device 100, respectively, which display alarm information, according to an exemplary embodiment.

As shown in FIG. 29A, the pill case 2900 may display administration notification information according to a control command received from the host device 100 or the management server 300. For example, the pill case 2900 may turn on an LED 2910 or include a graphic user interface (GUI) to provide information about whether a user administered a medicine. If the user is supposed to take blood pressure medicine at 18:00 but it is determines that the blood pressure medicine has not yet been administered at 18:30 upon analyzing measurement information measured by the pill case 2900, the management server 300 or the host device 100 may control the pill case 2900 to output a notification message 2920, "Take blood pressure medicine", on a display unit of the pill case 2900.

Alternatively, the management server 300 may provide prescription information to the pill case 2900. Here, when the user selects "CHECK PRESCRIPTION" 2930, the pill case 2900 may display the prescription on the display unit.

As shown in FIG. 29B, the host device 100 may display an administration notification message. For example, when the user has not taken blood pressure medicine at a certain period, the host device 100 may output a notification message, for example, "YOU HAVEN'T TAKEN BLOOD PRESSURE MEDICINE. TAKE IT", based on the administration notification information received from the management server 300.

The host device 100 may control the pill case 2900 based on the administration notification information received from the management server 300. Here, the host device 100 may control the pill case 2900 by executing an application related to the pill case 2900.

Figure 30:
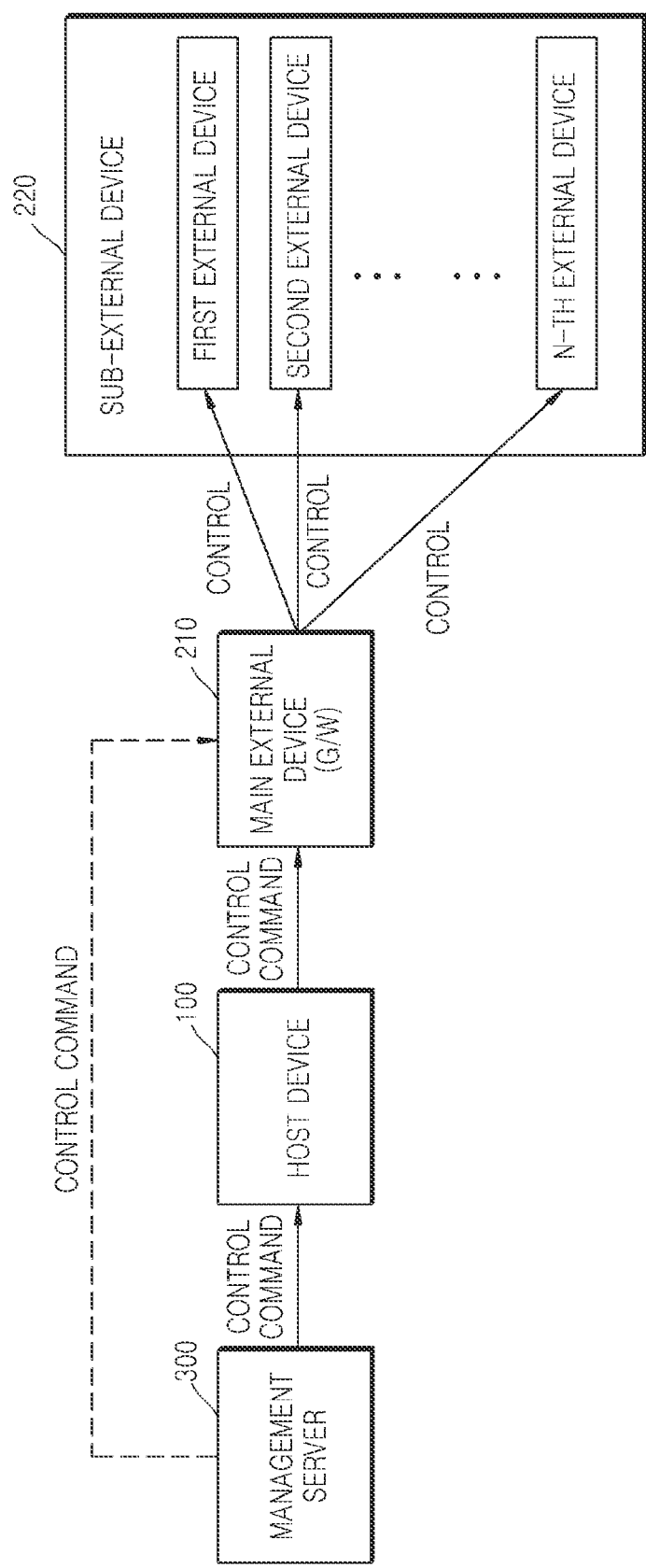
FIG. 30 is a block diagram of a system for managing a sub-external device, according to an exemplary embodiment.

FIG. 30 is a block diagram of a system for managing a sub-external device 220, according to an exemplary embodiment.

As shown in FIG. 30, the system may include the host device 100, a main external device 210, the sub-external device 200, and the management server 300. Since details about the host device 100 and the management server 300 overlap with those of FIG. 1, only the main external device 210 and the sub-external device 220 will be described in detail.

The main external device 210 may be connected to and controlled by the host device 100 through a first application installed in the host device 100. The sub-external device 220 may be connected to and controlled by the main external device 210 through a second application installed in the main external device 210.

The main external device 210 may obtain measurement information measured by the sub-external device 220 through wired communication, wireless communication, or short-range communication. Also, the main external device 210 may transmit the measurement information to the management server 300 through the host device 100 or directly.

The main external device 210 may receive a control command for controlling the sub-external device 220 from the management server 300 directly or through the host device 100.

Meanwhile, the main external device 210 may change the control command received from the management server 300 or the host device 100 according to a control protocol of the sub-external device 220. In other words, the main external device 210 may control the sub-external device 220 based on the control command received from the management server 300 or the host device 100.

The main external device 210 may be a gateway. The gateway may be a wireless relay base station. For example, the main external device 210 may be a wired/wireless internet router having internet sharing capability. Alternatively, the main external device 210 may be an AP having capability of interlocking wired communication and wireless communication, or a wireless router having capability of sharing the Internet with an AP.

The sub-external device 220 may be a device measuring health-related information of a user. Examples of the sub-external device 220 include a medical device, such as a blood sugar meter or a blood pressure gauge, a sporting apparatus, such as a bicycle, a treadmill, a hula hoop, a dumb-bell, a jump rope, or a smith machine, and a CE device, such as an air conditioner, an oven, a refrigerator, or a fan, but are not limited thereto.

Figure 31:
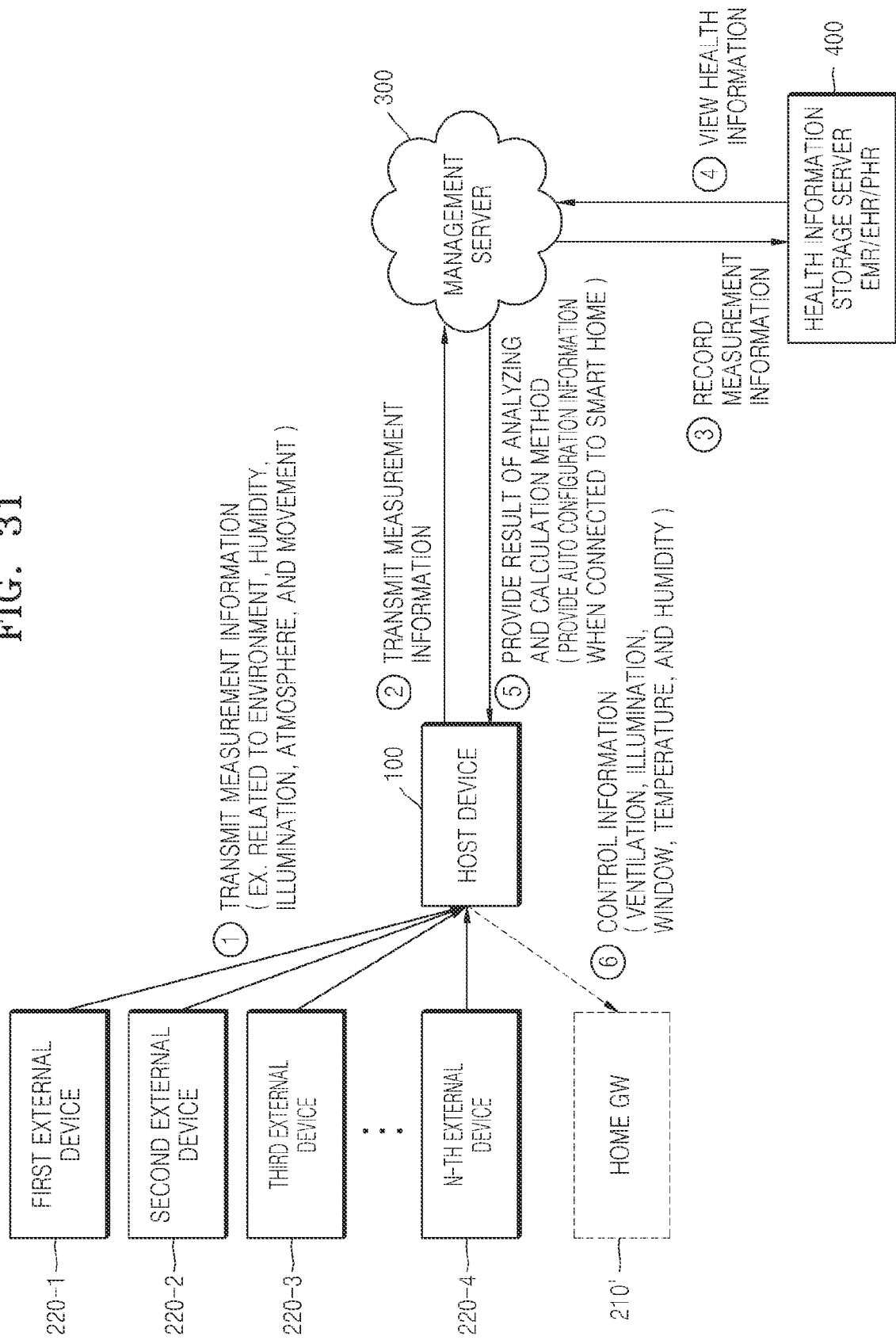
FIG. 31 is a diagram for describing a method of a management server managing an external device through a home gateway, according to an exemplary embodiment.

FIG. 31 is a diagram for describing a method of the management server 300 managing first through n-th external devices 220-1 through 220-*n*, through a home gateway 210', according to an exemplary embodiment As shown in FIG. 31, the host device 100 may obtain environment-related information, such as humidity, illumination, atmosphere, and movement, measured by the first through n-th external devices 220-1 through 220-*n*. Here, the host device 100 may transmit the obtained environment-related information to the management server 300.

The management server 300 may record the environment-related information in the health information storage server 400. Also, the management server 300 may extract health-related information of a user from the health information storage server 400.

The management server 300 may analyze a surrounding environment of the user based on the environment-related information, such as humidity, illumination, atmosphere, and movement, measured by the first through n-th external devices 220-1 through 220-n, and the health-related information extracted from the health information storage server 400. For example, the management server 300 may analyze whether a current environment is suitable or harmful to a user with asthma.

The management server 300 may transmit a result of the analyzing and/or recommended environment setting information to the host device 100. The host device 100 may generate control information for controlling the first through n-th external devices 220-1 through 220-n based on the result of analyzing and/or the recommended environment setting information. The control information may include ventilation necessity, an illumination setting value, window adjusting information, a temperature setting value, or a humidity setting value, but is not limited thereto.

The host device 100 may transmit the generated control information to the home gateway 210' that is a main external device. The home gateway 210' may control the first through n-th external devices 220-1 through 220-n connected to the home gateway 210', based on the control information received from the host device 100. For example, the home gateway 210' may close or open a window, change illumination, or control a humidifier or air conditioner.

Figure 32:
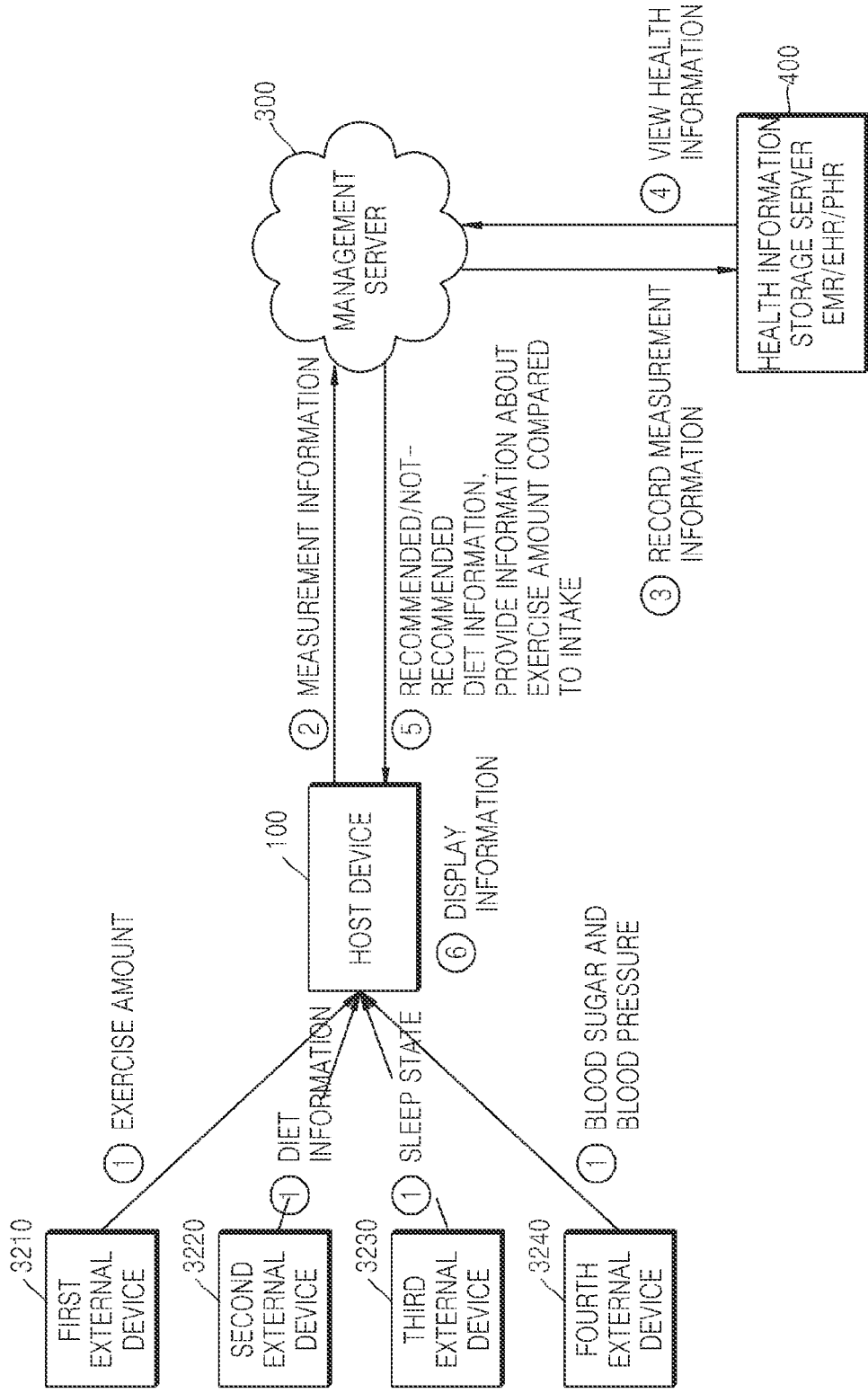
FIG. 32 is a diagram for describing a method of a management server providing recommended/not-recommended diet information, according to an exemplary embodiment.

FIG. 32 is a diagram for describing a method of the management server 300 providing recommended/not-recommended diet information, according to an exemplary embodiment.

The host device 100 may receive health-related information of a user, such as exercise amount information, diet information, sleep state information, and blood sugar and blood pressure information, respectively, from first through fourth external devices 3210, 3220, 3230, and 3240. The host device 100 may transmit the health-related information to the management server 300. The management server 300 may record the health-related information in the health information storage server 400, and view health information of the user recorded in the health information storage server 400.

The management server 300 may generate recommended/not-recommended diet information based on the health-related information (for example, an exercise amount, administration, blood pressure, blood sugar, and a sleep state) and the viewed health information (for example, a disease). Alternatively, the management server 300 may generate recommended diet information based on recent diet information and exercise amount information of the user.

The management server 300 may transmit the recommended/not-recommended diet information to the host device 100. Here, the host device 100 may display the received recommended/not-recommended diet information on a screen. According to another embodiment, the management server 300 may transmit information about an exercise amount compared to a caloric intake, and information about a salt intake to the host device 100.

Figure 33:
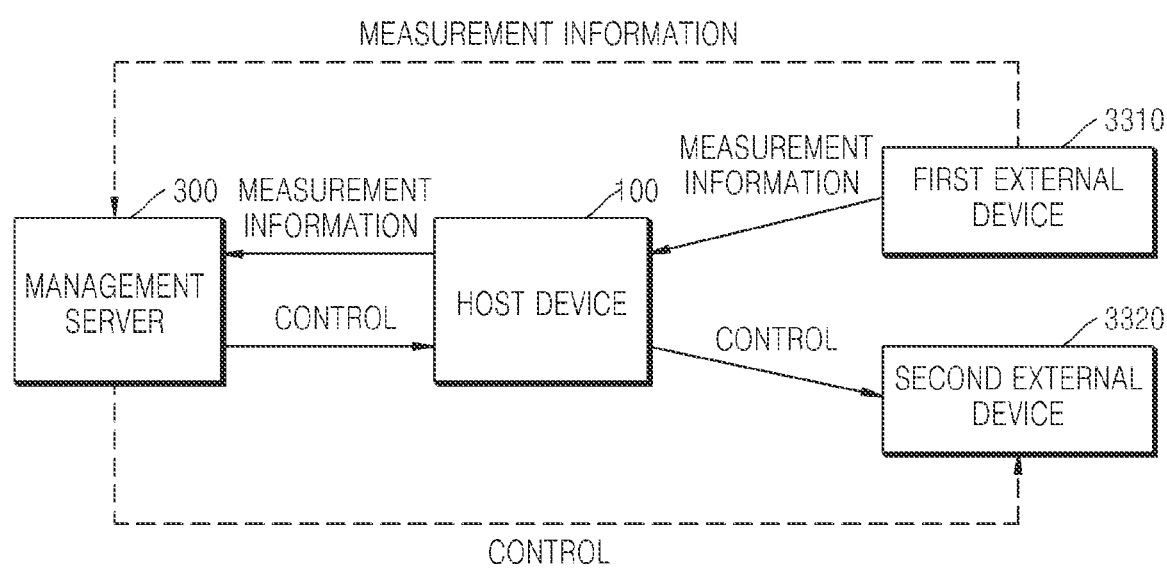
FIG. 33 is a block diagram of a system for a management server to control a second external device by using measurement information obtained by a first external device, according to an exemplary embodiment.

FIG. 33 is a block diagram of a system for the management server 300 to control a second external device 3320 by using measurement information obtained by a first external device 3310, according to an exemplary embodiment.

As shown in FIG. 33, the host device 100 may obtain measurement information measured by the first external device 3310 from the first external device 3310. Then, the host device 100 may transmit the obtained measurement information to the management server 300. Here, the management server 300 may analyze the measurement information measured by the first external device 3310, and generate control information for controlling the second external device 3320 based on a result of the analyzing.

The management server 300 may transmit the generated control information to the host device 100. The host device 100 may control the second external device 3320 according to the received control information. Alternatively, the management server 300 may obtain the measurement information directly from the first external device 3310, and directly control the second external device 3320.

According to an embodiment, an external device providing measurement information to the management server 300 or the host device 100 may be different from an external device being controlled by the management server 300 or the host device 100.

Figure 34A:
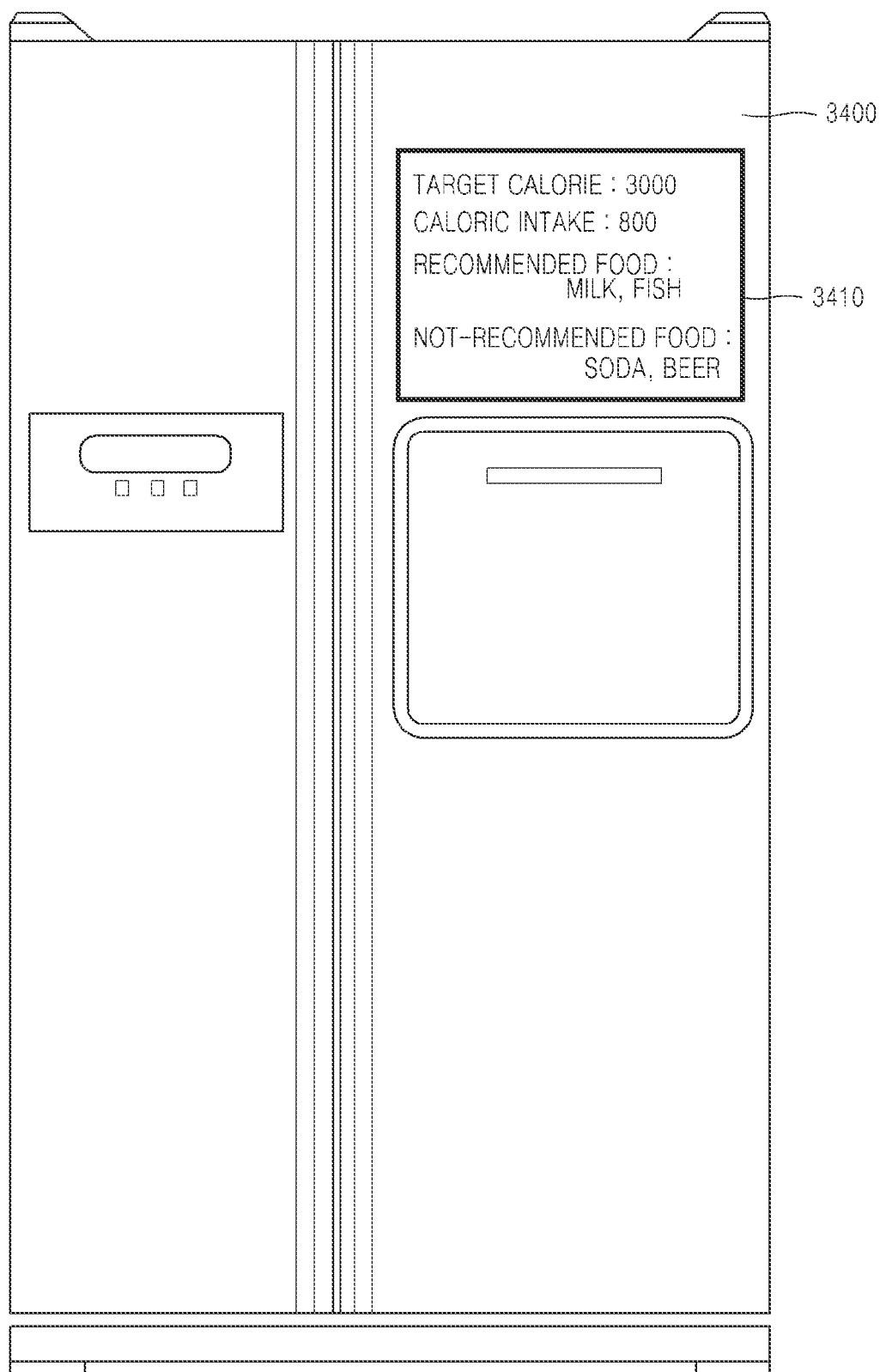
FIGS. 34A and 34B are diagrams for describing a system for a management server to control a second external device by using measurement information obtained by a first external device, according to an exemplary embodiment.
Figure 34B:

FIGS. 34A and 34B are diagrams for describing a system for the management server 300 to control a second external device by using measurement information obtained by a first external device, according to an exemplary embodiment.

As described above with reference to FIG. 32, the management server 300 may generate recommended/not-recommended food information based on health-related information, such as an exercise amount, administration, a sleep state, blood sugar, and blood pressure, obtained from each of the first through fourth external devices 3210 through 3240, and disease information of the user.

Here, the management server 300 may generate a control command for controlling a refrigerator 3400 such that the recommended/not-recommended food information is displayed on a display unit 3410 of the refrigerator 3400. Also, the management server 300 may transmit the control command to the refrigerator 3400 directly or through the host device 100 or the home gateway 210'. In other words, the management server 300 may control the refrigerator 3400 that is an external device different from a medical device, a blood sugar meter, a blood pressure gauge, or a pill case, which provided measurement information.

As shown in FIG. 34 (*a*), the refrigerator 3400 may display a daily target caloric intake, calorie left until target calorie, recommended food, and not-recommended food on the display unit 3410 according to the control command.

Meanwhile, as shown in FIG. 34 (*b*), the host device 100 may also display target calorie, caloric intake, left calorie, and recommended food on a screen based on the control command of the management server 300.

FIG. 35 is a diagram for describing a method of the management server 300 updating an external device 3500, according to an exemplary embodiment.

As shown in FIG. 35, the host device 100 may request the external device 3500 to perform a test. In response to the request, the external device 3500 may perform the test and transmit a test result to the host device 100. The host device 100 may analyze the received test result. If it is determined that a system error occurred in the external device 3500 based on the analyzing, the host device 100 may report the system error to the management server 300.

The management server 300 may request and receive revision/update data to deal with the system error from an external device provider server 700. The management server 300 may transmit revision/update information and state analysis information to the host device 100.

Here, the host device 100 may update the external device 3500 or perform calibration on the external device 3500 based on the revision/update information and the state analysis information received from the management server 300.

Figure 36:
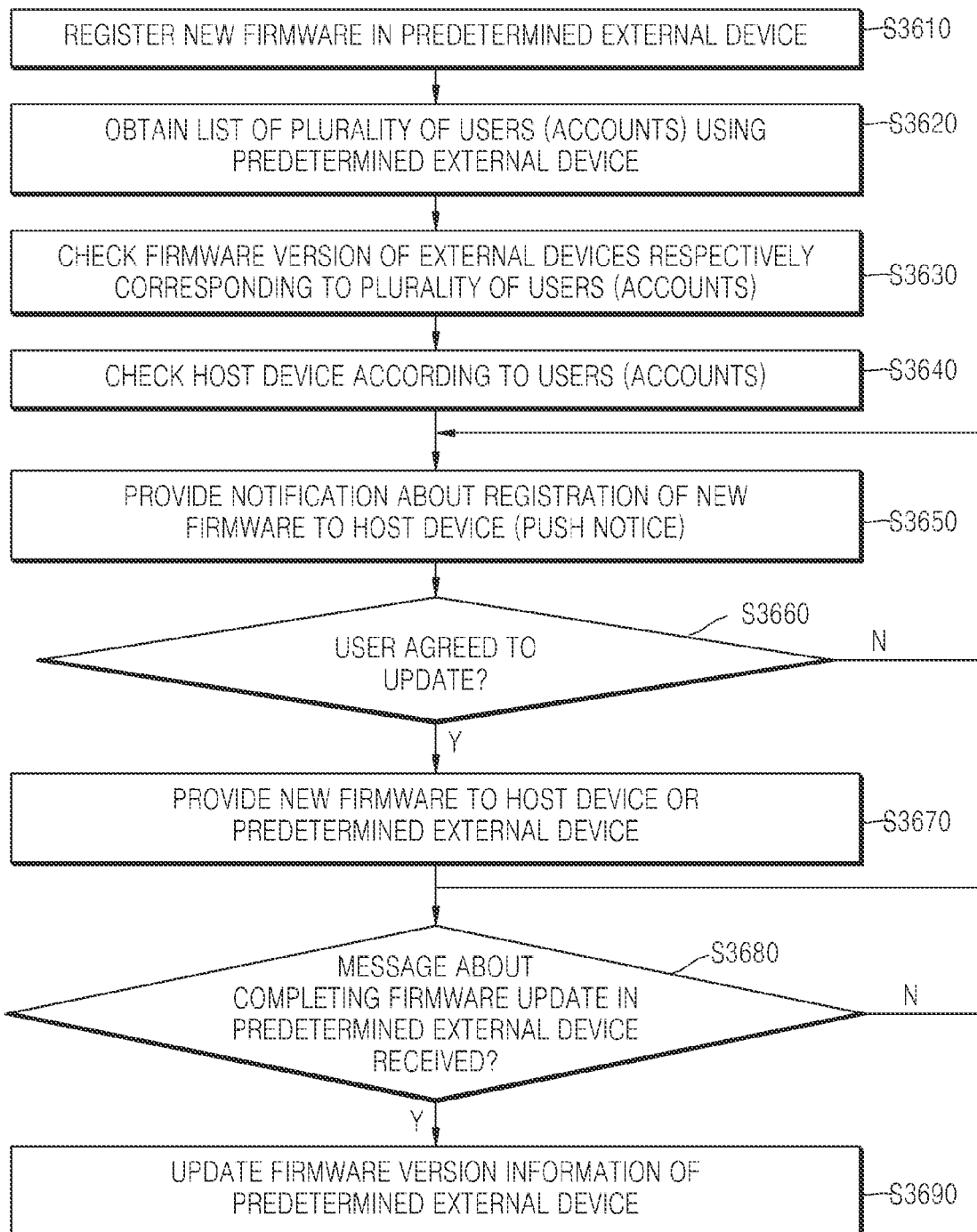
FIG. 36 is a flowchart illustrating a method of updating firmware of a plurality of external devices, according to an exemplary embodiment.

FIG. 36 is a flowchart illustrating a method of updating firmware of a plurality of external devices, according to an exemplary embodiment.

In operation S3610, new firmware may be registered in a predetermined external device. According to an embodiment, the new firmware may be registered in the external device provider server 700 or an application providing server. The external device provider server 700 may provide information about the registration of the new firmware to the management server 300.

In operation S3620, the management server 300 may obtain a list of a plurality of users (accounts) using the predetermined external device. In operation S3630, the management server 300 may check a firmware version of an external device corresponding to each of the plurality of users (accounts). When the checked firmware version is lower than a new firmware version, the management server 300 may check the host device 100 according to the users (accounts) in operation S3640. Then, the management server 300 may provide a notification about the registration of the new firmware to the host device 100 in operation S3650.

If it is determined that an update agreement message of the user is not received through the host device 100 in operation S3660, the management server 300 may again provide the notification about the registration of the new firmware to the host device 100.

If it is determined that the update agreement message of the user is received through the host device 100 in operation S3660, the management server 300 may provide the new firmware to the host device 100 or the predetermined external device in operation S3670.

It is determined whether the management server 300 received a message about completing the firmware update in the predetermined external device from the host device 100 or the predetermined external device in operation S3680. If the message is received, the management server 300 may update firmware version information of the predetermined external device in operation S3690.

If the new firmware is registered in the external device provider server 700 and the external device provider server 700 obtains the list of plurality of users (accounts) from the management server 300, operations S3630 through S3690 may be performed by the external device provider server 700.

Figure 37:
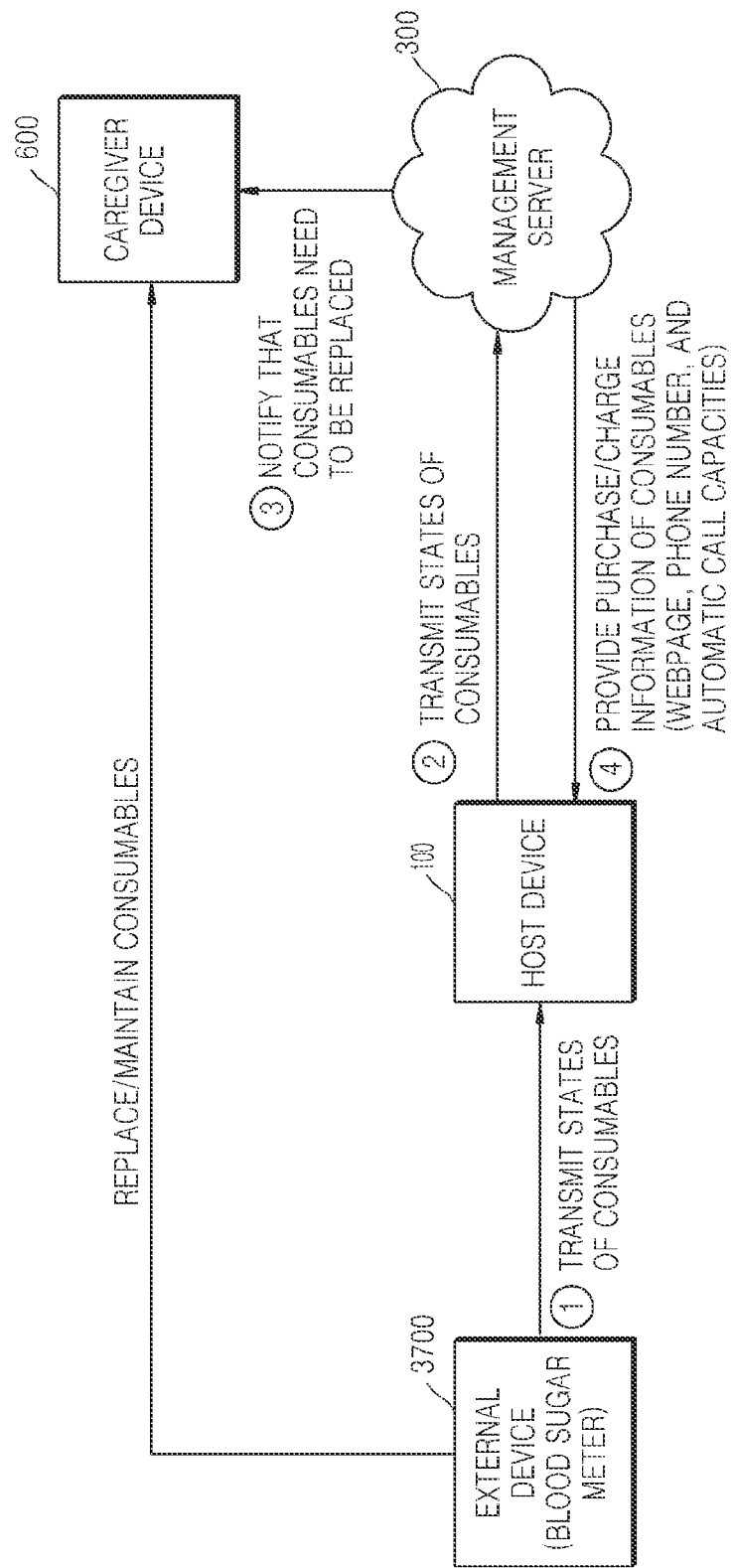
FIG. 37 is a diagram for describing a method of a management server managing consumables of an external device, according to an exemplary embodiment.

FIG. 37 is a diagram for describing a method of the management server 300 managing consumables of an external device 3700, according to an exemplary embodiment. In FIG. 37, the external device 3700 is a blood sugar meter.

The host device 100 may obtain state information (presence/absence or a remaining amount) of consumables, such as strips, measured by the external device 3700. The host device 100 may transmit the obtained state information to the management server 300. The management server 300 may analyze the state information. If it is determined that the consumables need to be replaced/added based on a result of the analyzing, the management server 300 may provide a notification to the caregiver device 600 so that a caregiver may replace/add the consumables.

Also, the management server 300 may provide purchase/charge information of consumables to the host device 100. For example, the management server 300 may provide webpage information or seller contact information for purchasing the consumables to the host device 100.

Figure 38:
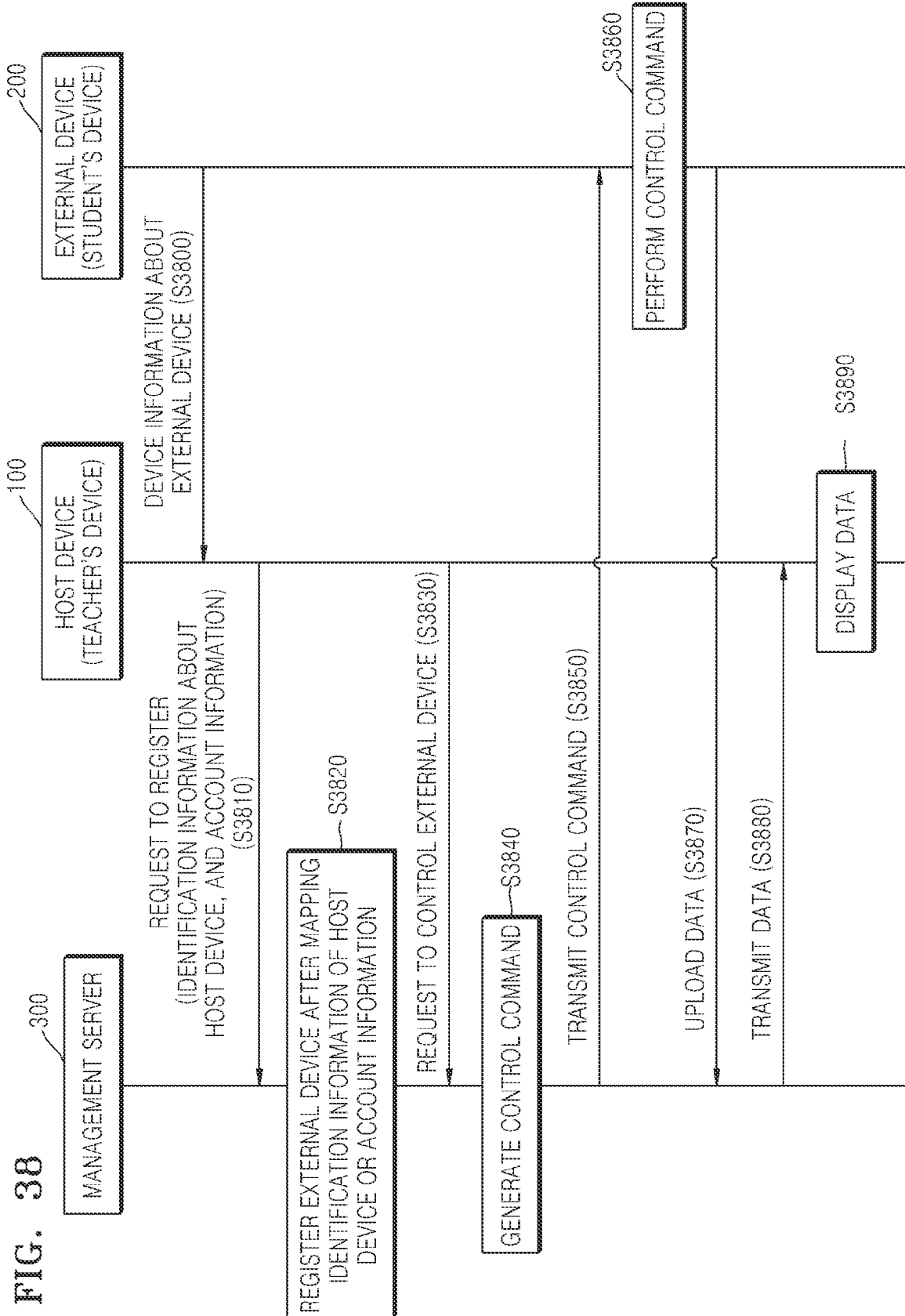
FIG. 38 is a flowchart illustrating a method of a host device (a teacher's device) managing an external device (a student's device) through a management server, according to an exemplary embodiment.

FIG. 38 is a flowchart illustrating a method of the host device 100 (a teacher's device) managing the external device 200 (a student's device) through the management server 300, according to an exemplary embodiment In operation S3800, the host device 100 may receive device information about the external device 200 from the external device 200. The device information about the external device 200 may include identification information of the external device 200, connection information for connection with the external device 200, application information related to the external device 200, and control protocol information of the external device 200. Since operation S3800 corresponds to operation S220 of FIG. 2, details thereof will not be repeated here.

In operation S3810, the host device 100 may transmit the device information about the external device 200 to the management server 300 while requesting that the management server 300 register the external device 200. Here, the host device 100 may transmit at least one of account information and identification information about the host device 100 to the management server 300.

In operation S3820, the management server 300 may store the device information about the external device 200 in a list of registered external devices. Here, according to an embodiment, the management server 300 may map and manage the identification information of the external device 200 and at least one of the account information and the identification information of the host device 100.

In operation S3830, the management server 300 may receive a request from the host device 100 to control the external device 200. In operation S3840, the management server 300 may generate a control command for controlling the external device 200, based on the request from the host device 100. In operation S3850, the management server 300 may transmit the control command to the external device 200. In operation S3860, the management server 300 may perform the control command.

For example, the management server 300 may connect to the external device 200 and register an account (or a group of accounts) of the external device 200, i.e., a student's device, to an account of the host device 100, i.e., a teacher's device, according to a request of the host device 100. Here, the management server 300 may receive, from the host device 100, a control request for controlling the external device 200 to open a textbook, reproduce certain content, automatically download homework, or close a test application when a test is over. According to the request, the management server 300 may control the external device 200 to open a textbook, reproduce certain content, download an assignment, or close a test application when the test is over.

In operation S3870, the external device 200 may upload data to the management server 300. Here, in operation S3880, the management server 300 may transmit the uploaded data to the host device 100. In operation S3890, the host device 100 may display the received data on a screen.

For example, the external device 200 may upload assignment result data to the management server 300. Here, the management server 300 may check the host device 100 connected to the external device 200, and provide the assignment result data to the host device 100. A teacher may check the assignment result data displayed on the host device 100. Meanwhile, the management server 300 may transmit information about an application executed in the external device 200 to the host device 100.

According to an embodiment, an order of operations S3800 through S3890 may be changed, or some operations may be skipped.

Figure 39:
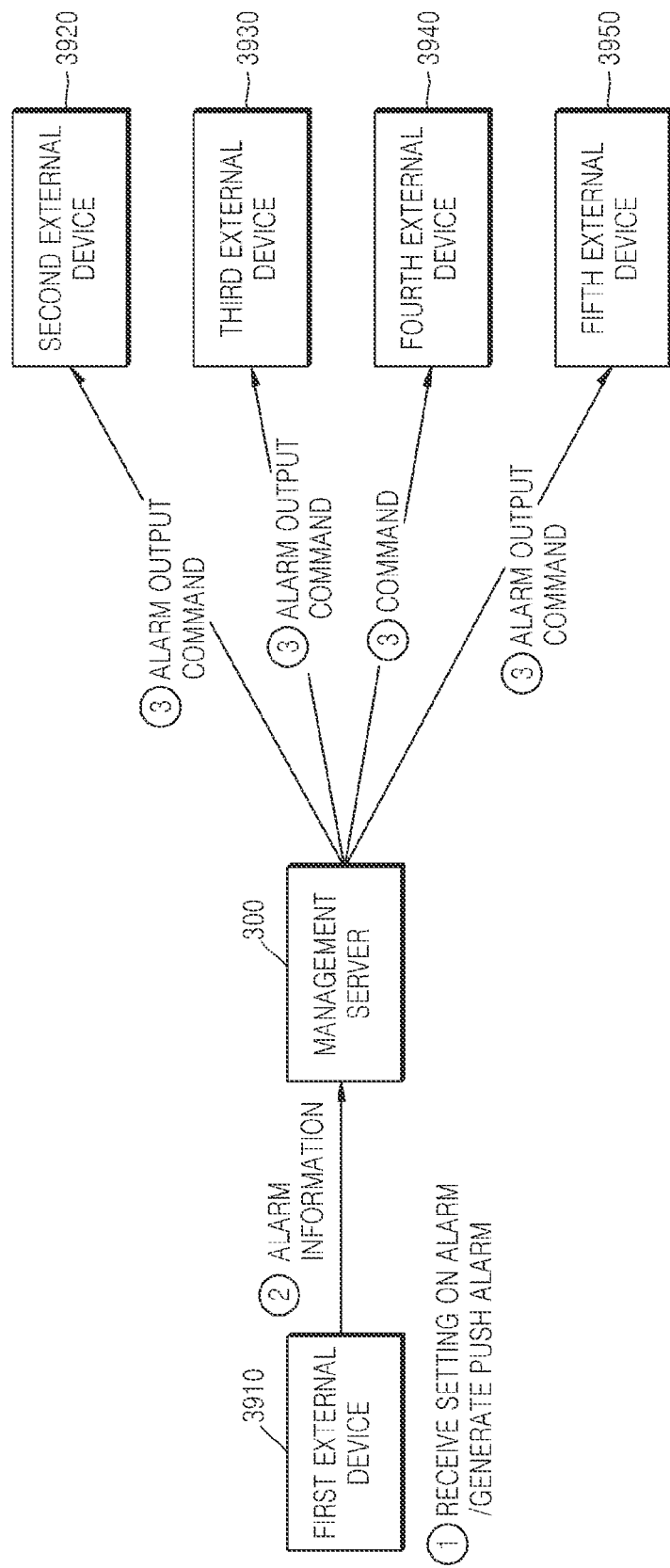
FIG. 39 is a diagram for describing a method of outputting an alarm generated/set in an external device to a plurality of external devices, according to an exemplary embodiment.

FIG. 39 is a diagram for describing a method of outputting an alarm generated/set in a first external device 3910 to second through fifth external devices 3920 through 3950, according to an exemplary embodiment.

A user may set an alarm in the first external device 3910. Here, the first external device 3910 may transmit alarm information to the management server 300. The management server 300 may transmit an alarm output command to the second through fifth external devices 3920 through 3950 that are pre-set to share the alarm information with the first external device 3910, based on the received alarm information. Here, the second through fifth external devices 3920 through 3950 output the alarm.

For example, when the user sets an alarm in a mobile phone to output vibration and/or music at 7:00, the mobile phone may transmit alarm information to the management server 300. Then, the management server 300 may transmit a control command to a watch, glasses, a PC, and a blood sugar meter so that the watch, the glasses, the PC, and the blood sugar meter generate the alarm at 7:00, as well as the mobile phone. Accordingly, the user is able to check the alarm in external devices (for example, the watch, the glasses, the PC, and the blood sugar meter) other than the mobile phone in which the alarm is set.

According to another embodiment, when a push alarm is generated in the first external device 3910, the first external device 3910 may transmit push alarm generation information to the management server 300. Here, the management server 300 may transmit an alarm output command to the second through fifth external devices 3920 through 3950 that are pre-set to share alarm information with the first external device 3910, based on the push alarm generation information. Here, the second through fifth external devices 3920 through 3950 output the push alarm.

The user may set a plurality of external devices to share an alarm output. For example, the user may set the first through fifth external devices 3910 through 3950 as a first external device group to share an alarm. Here, when an alarm is set or a push alarm is generated in one of the first through fifth external devices 3910 through 3950, the management server 300 may control the first through fifth external devices 3910 through 3950 to simultaneously output the alarm or the push alarm.

The host device 100 may connect to the management server 300 to remotely control at least one of the first through fifth external devices 3910 through 3950.

Figure 40:
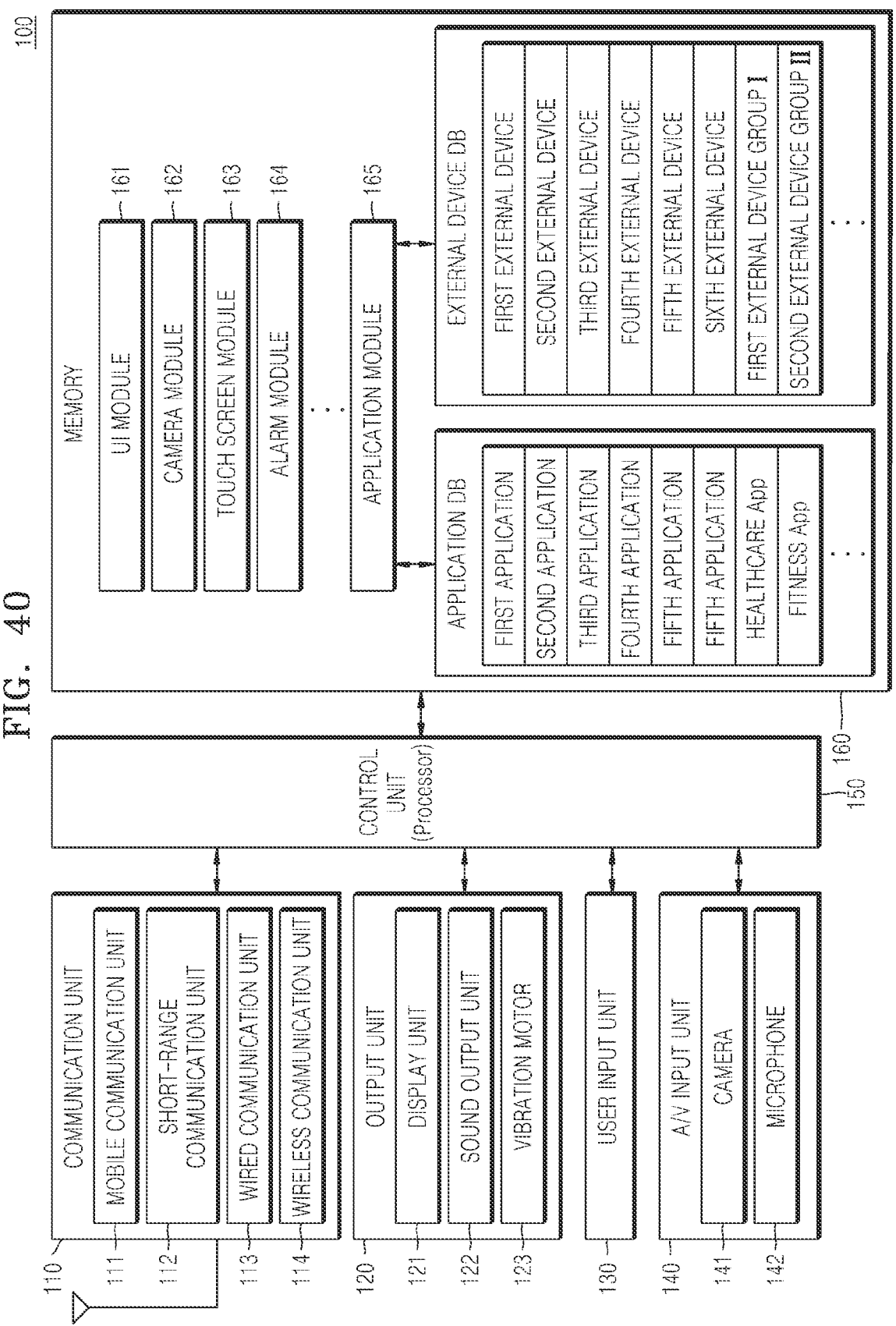
FIG. 40 is a block diagram of a host device according to an e exemplary embodiment.

FIG. 40 is a block diagram of the host device 100 according to an exemplary embodiment.

As shown in FIG. 40, the host device 100 may include a communication unit 110, an output unit 120, a user input unit 130, an audio/video (A/V) input unit 140, a control unit 150, and a memory 160. However, the components shown in FIG. 40 are not all essential. In other words, the host device 100 may include more or fewer components than shown in FIG. 40.

The above components will now be sequentially described.

The communication unit 110 may include at least one component enabling communication between the host device 100 and the at least one external device 200 or between the host device 100 and the management server 300. For example, the communication unit 110 may include a mobile communication unit 111, a short-range communication unit 112, a wired communication unit 113, and a wireless communication unit 114.

Examples of a short-range communication technology include WLAN such as Wi-Fi, Bluetooth, ZigBee, WFD, UWB, infrared data association (IrDA), and BLE, but are not limited thereto.

The output unit 120 is used to output an audio signal, a video signal, or a vibration signal, and may include a display unit 121, a sound output unit 122, and a vibration motor 123.

The display unit 121 displays information processed by the host device 100. For example, the display unit 121 may display management information for managing the external device 200 received from the management server 300.

When the display unit 121 has a touch screen structure in which the display unit 121 forms a layered structure with a touch pad, the display unit 121 may serve both as an output device and an input device. The display unit 141 may include at least one of a liquid crystal display (LCD), a thin film transistor-liquid crystal display (TFT-LCD), an organic light-emitting diode (OLED) display, a flexible display, a 3D display, and an electrophoretic display. The host device 100 may include at least two display units 121 depending on an implemented structure of the host device 100. The at least two display units 121 may be disposed opposite to each other with a hinge therebetween.

The sound output unit 122 may output audio data received from the communication unit 110 or stored in the memory 160. The sound output unit 122 may output a sound signal (for example, a call signal reception sound or a message reception sound) related to a function performed by the host device 100. The sound output unit 122 may include at least one of a speaker and a buzzer.

The vibration motor 123 may output a vibration signal. For example, the vibration motor 123 may output a vibration signal corresponding to an output of audio data or video data, such as a call signal reception sound or a message reception sound. The vibration motor 123 may also output a vibration signal when there is a touch input on a touch screen.

The user input unit 130 is a unit via which a user inputs data for controlling the host device 100. For example, the user input unit 130 may be a keypad, a dome switch, a touch pad (that is, a contact-type electrostatic capacity touch pad, a pressure-type resistive touch screen, an infrared ray detection-type touch pad, a surface ultrasonic wave conduction-type touch pad, an integrated tension measurement-type touch pad, a piezoelectric effect-type touch pad, or the like), a jog wheel, or a jog switch, but is not limited thereto.

The A/V input unit 140 is a unit for receiving an audio signal or a video signal, and may include a camera 141 and a microphone 142. The camera 141 may obtain an image frame of a still image or a moving picture in a video call mode or a shooting mode via an image sensor. An image captured by the image sensor may be processed by the control unit 150 or a separate image processing unit (not shown). A processed image frame may be displayed on the display unit 121, stored in the memory 160, or externally transmitted through the communication unit 110. Two or more cameras 141 may be included according to an embodiment of the host device 100.

The microphone 142 may receive an external sound signal and process the received external sound signal into electric voice data in a call mode, a recording mode, or a voice recognition mode. The electric voice data may be converted and output in a form transmittable to a mobile communication base station through the mobile communication unit 111 in a call mode.

The control unit 150 controls overall operations of the host device 100. That is, the control unit 150 may control the communication unit 110, the output unit 120, the user input unit 130, the A/V input unit 140, and the memory 160 by executing programs stored in the memory 160.

The control unit 150 may include an application processor and a communication processor. The application processor may control executing of various applications stored in the memory 160, and the communication processor may control various communication functions.

The memory 160 may store programs of processes and controls performed by the control unit 150, and input/output data, such as device information about the external device 200, measurement information measured by the external device 200, an application related to the external device 200, and management information for managing the external device 200.

The memory 160 may include at least one storage medium from among a flash memory, a hard disk, a multimedia card micro, a card-type memory such as a secure digital (SD) or extreme digital (XD) memory, random access memory (RAM), static random access memory (SRAM), read-only memory (ROM), electrically erasable programmable read-only memory (EEPROM), programmable read-only memory (PROM), a magnetic memory, a magnetic disc, and an optical disc. Additionally, the host device 100 may operate a web storage unit for performing a storage function of the memory 160 on the Internet.

The programs stored in the memory 160 may be classified into a plurality of modules according to functions. For example, the programs may be classified into a UI module 161, a camera module 162, a touch screen module 163, an alarm module 164, and an application module 165.

The UI module 161 may provide a specialized UI or GUI for each application that operates with the external device 200. The camera module 162 may capture and process an image of an object. Since functions of the UI module 161 and camera module 162 are intuitively inferred based on their names, details thereof are omitted herein.

The touch screen module 163 may detect a user's touch gesture on a touch screen and transmit information about the touch gesture to the control unit 150. The touch screen module 163 may be implemented as a separate hardware controller.

Various types of sensors may be disposed inside or near the touch screen, in order to detect a touch or a proximity touch on the touch screen. An example of a sensor for detecting a touch on the touch screen may be a tactile sensor. A tactile sensor is a sensor for detecting a contact of a specific object to such a degree that humans may feel it or to a higher degree. The tactile sensor may detect various types of information such as information about a roughness of a contact surface, a hardness of a contact object, or a temperature at a contact point.

Touch gestures of a user may be a tap, a touch and hold, a double-tap, a drag, panning, a flick, a drag-and-drop, and a swipe.

A "tap" is a gesture in which a user touches a screen by using a finger or a touch tool, for example, an electronic pen, and then, immediately lifts it off from the screen without dragging on the screen.

A "touch and hold" is a gesture in which a user touches a screen by using a finger or a touch tool, for example, an electronic pen, and holds the touch for more than a critical period of time, for example, 2 seconds. That is, a difference in time between time points of a touch on and a lift-off from the screen is longer than the critical period of time, for example, 2 seconds. If the touch input is held for more than the critical period of time to make a user recognize whether the touch input is a tap or a touch and hold, a feedback signal may be visually, aurally, or tactually provided. The critical period of time may vary according to exemplary embodiments.

A "double tap" is a gesture in which a user touches a screen twice by using a finger or a touch tool which may be a stylus.

A "drag" is a gesture in which a user touches a screen by using a finger or a touch tool and moves the finger or the touch tool to another location in the screen while holding the touch. When the drag is performed, an object moves, or a panning gesture, which is described below, is performed.

A "panning" gesture is a gesture in which a user performs a drag without selecting an object. As the panning does not select a specific object, an object does not move in a page, and the page moves in the screen or a group of objects moves in the page.

A "flick" is a gesture in which a user performs a drag at a critical speed or at a higher speed, for example, 100 pixels per second, by using a finger or a touch tool. The flick may be distinguished from the drag or the panning based on whether a moving speed of a finger or a touch tool is equal to or higher than the critical speed, for example, 100 pixels/s.

A "drag and drop" is a gesture in which a user drags an object to a predetermined place in a screen by using a finger or a touch tool, and then, lifts the finger or touch tool off the screen.

A "pinch" is a gesture in which a user touches a screen with two fingers and moves the two fingers in different directions. The pinch may be a pinch-open gesture for zooming-in to an object or a page, or a pinch-close gesture for zooming-out from an object or a page. A zoom-in or zoom-out value is determined according to a distance between the two fingers.

A "swipe" is a gesture for touching an object in a screen by using a finger or a touch tool and moving the finger or the touch tool in a horizontal or vertical direction for a certain distance. Moving in a diagonal direction may or may not be recognized as a swipe event.

The memory 160 may include a voice recognition module (not illustrated) for recognizing a voice of a user by using a voice recognition engine and transmitting the recognized voice signal to the control unit 150.

The alarm module 164 may generate a signal for notifying generation of an event in the host device 100. Examples of the event generated in the host device 100 may include call signal reception, message reception, key signal input, and schedule notification.

The alarm module 164 may output an alarm signal in the form of a video signal via the display unit 121 or in the form of an audio signal via the sound output unit 122. The alarm module 164 may also output an alarm signal in the form of a vibration signal via the vibration motor 123.

The alarm module 164 may provide a snooze function. For example, if a user sets the number of alarm repetitions to be, for example, 5 times, or an alarm interval to be, for example, 3 minutes, the alarm module 164 may output an alarm signal by a predetermined number of times, for example, 5 times, or at a predetermined interval, for example, every 3 minutes.

The application module 165 may be connected to an application DB or an external device DB. The application DB may store applications for controlling the external device 200, but is not limited thereto. For example, the application DB may store a healthcare application for managing a medical device, a fitness application for controlling a sporting apparatus, and a reminder application for outputting a notification. The external device DB may store device information about the external device 200 and measurement information measured by the external device 200.

The application module 165 may control the external device 200 by using the application for controlling the external device 200. Also, the application module 165 may provide the application for controlling the external device 200 to the management server 300.

Figure 41:
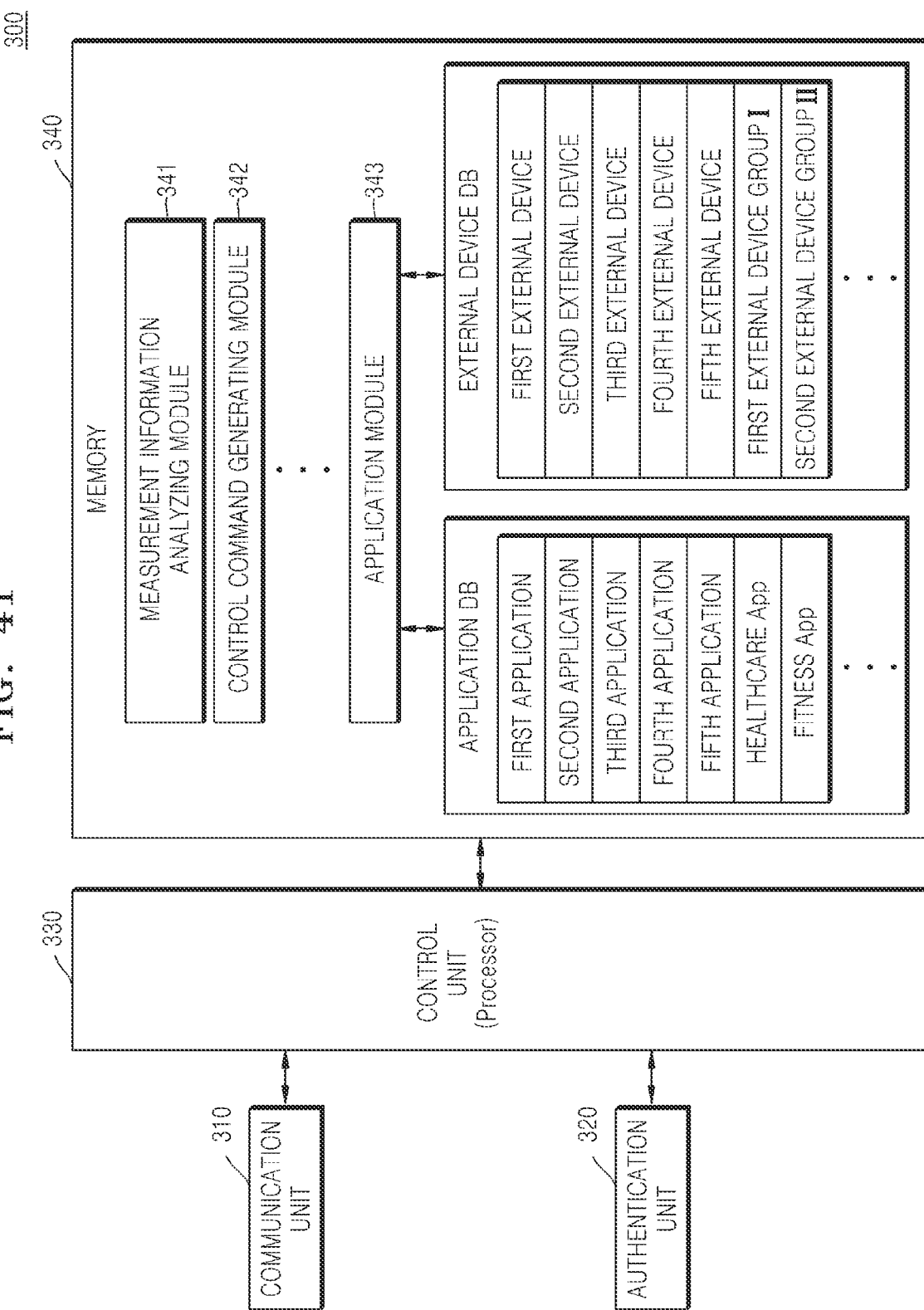
FIG. 41 is a block diagram of a management server according to an exemplary embodiment.

FIG. 41 is a block diagram of the management server 300 according to an exemplary embodiment.

As shown in FIG. 41, the management server 300 may include a communication unit 310, an authentication unit 320, a control unit 330, and a memory 340. However, the components shown in FIG. 41 are not all essential. The management server 300 may be realized by using more or less components than shown in FIG. 41.

The above components will now be sequentially described in detail.

The communication unit 310 may include at least one component enabling communication between the management server 300 and the at least one external device 200, between the management server 300 and the host device 100, or between the management server 300 and an external server. According to an embodiment, the communication unit 310 may receive measurement information measured by the external device 200 from the external device 200 or the host device 100. Also, the communication unit 310 may transmit management information for managing the external device 200 to the host device 100. The communication unit 310 may transmit a control command to the host device 100 or the external device 200.

The authentication unit 320 may authenticate the host device 100. For example, the authentication unit 320 may authenticate account information (for example, an ID and a password) received from the host device 100, or identification information of the host device 100. Also, the authentication unit 320 may check authentication information received from the external device 200. Meanwhile, the authentication unit 320 may decode encoded measurement information by using a pre-defined decoding key.

The control unit 330 controls overall operations of the management server 300. For example, the control unit 330 may control the communication unit 310, the authentication unit 320, and the memory 340, or control the external device 200 and the host device 100, by using programs stored in the memory 340.

The memory 340 may store programs of processes and controls performed by the control unit 330, or store input/output data, such as device information about the external device 200, measurement information measured by the external device 200, an application related to the external device 200, information about the host device 100 interworking with the external device 200, and management information for managing the external device 200.

The programs stored in the memory 340 may be classified into a plurality of modules according to functions. For example, the programs may be classified as a measurement information analyzing module 341, a control command generating module 342, and an application module 343.

The measurement information analyzing module 341 may determine a health state of a user by analyzing received measurement information. Also, the measurement information analyzing module 341 may analyze the measurement information to determine a replacement cycle of consumables and whether firmware is required to be updated. Meanwhile, the measurement information analyzing module 341 may generate recommended/not-recommended food information or exercise recommendation information.

The control command generating module 342 may generate a control command for managing the host device 100 or the at least one external device 200. Here, the control command generating module 342 may convert the control command according to a control protocol of the host device 100 or the at least one external device 200.

The application module 343 may be connected to an application DB and an external device DB by using an application for controlling the external device 200. The application DB may store applications for controlling the external device 200, but is not limited thereto. For example, the application DB may store a healthcare application for controlling a medical device, a fitness application for controlling a sporting apparatus, and a remainder application for outputting a notification. The external device DB may store device information about the external device 200, measurement information measured by the external device 200, information about the host device 100 connected to the external device 200, and account information.

The application module 343 may control the external device 200 by using the application for controlling the external device 200.

The methods described above may be recorded on a computer readable recording medium by being realized in computer programs executed by using various computers. The computer readable recording medium may include at least one of a program command, a data file, and a data structure. The program commands recorded in the computer readable recording medium may be specially designed or well known to one of ordinary skill in the computer software field. Examples of the computer readable recording medium include read-only memory (ROM), random-access memory (RAM), CD-ROMs, magnetic tapes, floppy disks, optical data storage devices, etc. Examples of the computer command include mechanical codes prepared by a compiler, and high-level languages executable by a computer by using an interpreter.

While one or more embodiments have been described with reference to the figures, it will be understood by those of ordinary skill in the art that various changes in form and details may be made therein without departing from the spirit and scope of the inventive concept as defined by the following claims.

What is claimed is:

1. An electronic device for managing a wearable device, the electronic device comprising:
    a touch screen;
    a first communication interface configured to communicate with a server;
    a second communication interface configured to communicate with the wearable device, the wearable device being registered in the server via the electronic device;
    a memory configured to store a healthcare application for managing health-related information received from the wearable device; and
    a processor configured to:
        execute the healthcare application in the electronic device,
        receive, from the wearable device via the second communication interface of the electronic device, the health-related information during the execution of the healthcare application for managing the health-related information in the electronic device, wherein the health-related information is obtained by the wearable device, wherein a firmware is installed in the wearable device,
display the received health-related information on the touch screen of the electronic device,
receive, from the server via the first communication interface of the electronic device, firmware update information for updating the firmware installed in the wearable device,
display, on the touch screen of the electronic device, a notification information indicating that an update of the firmware installed in the wearable device is available, and
transmit, to the server via the first communication interface of the electronic device, an update agreement message responding to the firmware update information to cause, during the execution of the healthcare application for managing the health-related information in the electronic device, the wearable device to update the firmware installed in the wearable device in response to receiving the firmware update information through the electronic device.

2. The electronic device of claim 1, wherein the health-related information comprises at least one of blood sugar, blood pressure, a heart rate, a weight, or exercise information.

3. The electronic device of claim 1, wherein the firmware update information comprises information about a registration of new firmware to the server.

4. The electronic device of claim 1, wherein the processor is further configured to transmit, to the server via the first communication interface, account information for authentication.

5. The electronic device of claim 1, wherein the processor is further configured to receive, from the wearable device via the second communication interface, device information with respect to the wearable device.

6. The electronic device of claim 5, wherein the processor is further configured to transmit, to the server via the first communication interface, the received device information with respect to the wearable device to register the wearable device with account information in the server based on a successful authentication.

7. The electronic device of claim 1, wherein the processor is further configured to:
transmit, to the server via the first communication interface of the electronic device, the health-related information,
receive, from the server via the first communication interface of the electronic device, management information corresponding to the health-related information,
generate a control command for controlling the wearable device based on the management information, and
transmit the generated control command to the wearable device via the second communication interface of the electronic device.

8. A method for managing a wearable device by an electronic device, the method comprising:
executing, in the electronic device, a healthcare application for managing health-related information received from the wearable device;
receiving, from the wearable device via a second communication interface of the electronic device, the health-related information during the execution of the healthcare application for managing the health-related information in the electronic device, wherein the health-related information is obtained by the wearable device, wherein a firmware is installed in the wearable device;
displaying the received health-related information on a touch screen of the electronic device;
receiving, from a server via a first communication interface of the electronic device, firmware update information for updating the firmware installed in the wearable device, the wearable device being registered in the server via the electronic device;
displaying, on the touch screen of the electronic device, a notification information indicating that an update of the firmware installed in the wearable device is available; and
transmitting, to the server via the first communication interface of the electronic device, an update agreement message responding to the firmware update information to cause, during the execution of the healthcare application for managing the heath-related information in the electronic device, the wearable device to update the firmware installed in the wearable device in response to receiving the firmware update information through the electronic device.

9. The method of claim 8, wherein the health-related information comprises at least one of blood sugar, blood pressure, a heart rate, a weight, or exercise information.

10. The method of claim 8, wherein the firmware update information comprises information about a registration of new firmware to the server.

11. The method of claim 8, further comprising:
transmitting, to the server via the first communication interface, account information for authentication.

12. The method of claim 8, further comprising:
receiving, from the wearable device via the second communication interface, device information with respect to the wearable device.

13. The method of claim 12, further comprising:
transmitting, to the server via the first communication interface, the received device information with respect to the wearable device to register the wearable device with account information in the server based on a successful authentication.

14. The method of claim 8, further comprising:
transmitting, to the server via the first communication interface of the electronic device, the health-related information,
receiving, from the server via the first communication interface of the electronic device, management information corresponding to the health-related information,
generating a control command for controlling the wearable device based on the management information, and
transmitting the generated control command to the wearable device via the second communication interface of the electronic device.

15. A non-transitory computer-readable storage medium having a computer readable program stored therein, wherein the computer readable program, when executed on an electronic device, causes the electronic device to:
execute, in the electronic device, a healthcare application for managing health-related information received from a wearable device,
receive, from the wearable device via a second communication interface of the electronic device, the health-related information during the execution of the healthcare application for managing the health-related information in the electronic device, wherein the health-related information is obtained by the wearable device, wherein a firmware is installed in the wearable device, display the received health-related information on a touch screen of the electronic device;

receive, from a server via a first communication interface of the electronic device, firmware update information for updating the firmware installed in the wearable device, the wearable device being registered in the server via the electronic device, display, on the touch screen of the electronic device, a notification information indicating that an update of the firmware installed in the wearable device is available, and transmit, to the server via the first communication interface of the electronic device, an update agreement message responding to the firmware update information to cause, during the execution of the healthcare application for managing the health-related information in the electronic device, the wearable device to update the firmware installed in the wearable device in response to receiving the firmware update information through the electronic device.

16. The non-transitory computer-readable storage medium of claim 15, wherein the health-related information comprises at least one of blood sugar, blood pressure, a heart rate, a weight, or exercise information.

17. The non-transitory computer-readable storage medium of claim 15, wherein the firmware update information comprises information about a registration of new firmware to the server.

18. The non-transitory computer-readable storage medium of claim 15, wherein the computer readable program, when executed on the electronic device, causes the electronic device to transmit, to the server via the first communication interface, account information for authentication.

19. The non-transitory computer-readable storage medium of claim 15, wherein the computer readable program, when executed on the electronic device, causes the electronic device to receive, from the wearable device via the second communication interface, device information with respect to the wearable device.

20. The non-transitory computer-readable storage medium of claim 15, wherein the computer readable program, when executed on the electronic device, causes the electronic device to transmit, to the server via the first communication interface, the received device information with respect to the wearable device to register the wearable device with account information in the server based on a successful authentication.

21. The non-transitory computer-readable storage medium of claim 15, wherein the computer readable program, when executed on the electronic device, causes the electronic device to:

transmit, to the server via the first communication interface of the electronic device, the health-related information, receive, from the server via the first communication interface of the electronic device, management information corresponding to the health-related information, generate a control command for controlling the wearable device based on the management information, and transmit the generated control command to the wearable device via the second communication interface of the electronic device.

* * * * *